US008039026B1

(12) United States Patent
Niemiec

(10) Patent No.: US 8,039,026 B1
(45) Date of Patent: *Oct. 18, 2011

(54) METHODS FOR TREATING SKIN PIGMENTATION

(75) Inventor: Susan M. Niemiec, Ann Arbor, MI (US)

(73) Assignee: Johnson & Johnson Consumer Companies, Inc, Skillman, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/110,409

(22) Filed: Jul. 6, 1998

Related U.S. Application Data

(60) Provisional application No. 60/080,441, filed on Apr. 2, 1998, provisional application No. 60/053,942, filed on Jul. 28, 1997.

(51) Int. Cl.
A61K 36/48 (2006.01)
A61K 36/00 (2006.01)
A61K 31/445 (2006.01)

(52) U.S. Cl. ......... 424/757; 424/725; 514/317; 514/321
(58) Field of Classification Search .................. 514/317, 514/321; 424/757, 725
See application file for complete search history.

(56) References Cited

U.S. PATENT DOCUMENTS

| 2,924,525 | A | * | 2/1960 | Kruse et al. .................. 514/729 |
|---|---|---|---|---|
| 3,097,947 | A | | 7/1963 | Kemmerer |
| 3,625,976 | A | | 12/1971 | Theimer |
| 3,755,560 | A | | 8/1973 | Dickert |
| 4,007,266 | A | | 2/1977 | Choay |
| 4,056,637 | A | | 11/1977 | Hagiwara et al. |
| 4,151,304 | A | | 4/1979 | Evans |
| 4,190,671 | A | | 2/1980 | Vanstone |
| 4,219,569 | A | | 8/1980 | Glenn |
| 4,223,018 | A | | 9/1980 | Belle |
| 4,254,105 | A | | 3/1981 | Fukuda |
| 4,272,544 | A | | 6/1981 | Cella |
| 4,278,570 | A | | 7/1981 | Flom |
| 4,279,930 | A | | 7/1981 | Hall |
| 4,297,348 | A | | 10/1981 | Frazier |
| 4,331,692 | A | | 5/1982 | Drevici |
| 4,333,927 | A | | 6/1982 | Ofuchi |
| 4,368,187 | A | | 1/1983 | Flom |
| 4,370,315 | A | | 1/1983 | Greff |
| 4,382,960 | A | | 5/1983 | Flom |
| 4,386,067 | A | | 5/1983 | Guillon |
| 4,421,769 | A | | 12/1983 | Dixon |
| 4,427,670 | A | | 1/1984 | Ofuchi |
| 4,434,095 | A | | 2/1984 | Chipens et al. |
| 4,437,895 | A | | 3/1984 | Koulbanis |
| 4,439,418 | A | | 3/1984 | Moller |
| 4,462,981 | A | | 7/1984 | Smith |
| 4,477,434 | A | | 10/1984 | Kosaka |
| 4,486,448 | A | | 12/1984 | Ser |
| 4,488,564 | A | | 12/1984 | Grollier |
| 4,512,973 | A | | 4/1985 | Dennis |
| 4,515,778 | A | | 5/1985 | Kastell |
| 4,524,067 | A | | 6/1985 | Arichi |
| 4,537,782 | A | | 8/1985 | Millet |
| 4,550,035 | A | | 10/1985 | Smith |
| 4,578,267 | A | | 3/1986 | Salamone |
| 4,584,190 | A | | 4/1986 | Tejima |
| 4,603,146 | A | | 7/1986 | Kligman |
| 4,604,281 | A | | 8/1986 | Deckner |
| 4,612,192 | A | | 9/1986 | Scheuffgen |
| 4,690,821 | A | | 9/1987 | Smith |
| 4,707,293 | A | | 11/1987 | Ferro |
| 4,727,088 | A | | 2/1988 | Scott et al. |
| 4,760,096 | A | | 7/1988 | Sakai |
| 4,793,991 | A | | 12/1988 | Slimak |
| 4,824,662 | A | | 4/1989 | Hofmann |
| 4,834,076 | A | | 5/1989 | Millet |
| 4,847,267 | A | | 7/1989 | Deckner |
| 4,851,214 | A | | 7/1989 | Walters |
| 4,859,458 | A | | 8/1989 | Salamone |
| 4,867,964 | A | | 9/1989 | Forestier |
| 4,871,530 | A | | 10/1989 | Grollier |
| 4,885,169 | A | | 12/1989 | Gazzani |
| 4,895,839 | A | | 1/1990 | Bombardelli |
| 4,906,457 | A | | 3/1990 | Ryan |
| 4,915,972 | A | * | 4/1990 | Gupta et al. .................. 426/598 |
| 4,943,462 | A | | 7/1990 | Komerska |
| 4,960,588 | A | | 10/1990 | Hoshowski |
| 4,960,764 | A | | 10/1990 | Figueroa |
| 4,970,216 | A | | 11/1990 | Deckner |
| 4,971,825 | A | | 11/1990 | Kitazume et al. |
| 4,978,528 | A | | 12/1990 | Degre |
| 5,002,761 | A | | 3/1991 | Mueller |
| 5,006,337 | A | | 4/1991 | Motitschke et al. |
| 5,032,382 | A | | 7/1991 | Grollier |
| 5,032,400 | A | | 7/1991 | Wiersum et al. |
| 5,043,323 | A | | 8/1991 | Bombardelli |

(Continued)

FOREIGN PATENT DOCUMENTS

AU 724988 B2 5/1998

(Continued)

OTHER PUBLICATIONS

The Free Dictionay, the defination of "Denatured" 2006.*
JP 10139654, Tanaka et al. enclosed abstract.*
JP 06256156, Ogawa, enclosed abstract.*
Adhesion Molecule Expression in Normal Skin and Melanocytic Lesions. Tronnier, Michael, et al. Journal of Cutaneous Pathology, 1997, pp. 278-285.
Altered Cell Signaling and Mononuclear Phagocyte Deactivation During Interacellular Infection. Reiner, Neil E. Immunology Today. 1994. pp. 374-381.
A Growth-regulated Protease Activity That is Inhibited by the Anticarcinogenic Bowen-Birk Protease Inhibitor, Billings et al., Pro. Natl. Acad. Sd. 89:3120-3124 (1992).
Amino Acid Sequence and Secondary Structural Analysis of the Corn Inhibitor of Trypsin and Activated Hageman Factor, Walter C. Mahoney:: Journal of Biological Chemistry, vol. 259, No. 13 Jul. 10, 1984, 8412-8416.

(Continued)

Primary Examiner — Kevin Weddington

(57) ABSTRACT

This invention relates to methods and compositions for bringing about changes in skin pigmentation. More particularly, this invention relates to compounds which affect melanogenesis and can be used as depigmenting agents or as agents for darkening skin utilizing the PAR-2 pathway.

13 Claims, 25 Drawing Sheets

U.S. PATENT DOCUMENTS

| | | |
|---|---|---|
| 5,057,417 A | 10/1991 | Hammonds et al. |
| 5,077,038 A | 12/1991 | Hofmann |
| 5,077,040 A | 12/1991 | Bergmann |
| 5,104,655 A | 4/1992 | Bombardelli |
| 5,110,603 A | 5/1992 | Rau |
| 5,116,605 A | 5/1992 | Alt |
| 5,118,671 A | 6/1992 | Bombardelli |
| 5,130,142 A | 7/1992 | Wong et al. |
| 5,147,859 A | 9/1992 | Bombardelli |
| 5,166,139 A | 11/1992 | Bombardelli |
| 5,171,577 A | 12/1992 | Griat |
| 5,179,091 A | 1/1993 | Lesieur |
| 5,188,823 A | 2/1993 | Shapiro |
| 5,192,332 A | 3/1993 | Lang |
| 5,194,252 A | 3/1993 | Hofmann |
| 5,217,717 A | 6/1993 | Kennedy |
| 5,229,104 A | 7/1993 | Sottery |
| 5,231,090 A | 7/1993 | Hsia |
| 5,248,495 A | 9/1993 | Patterson |
| 5,254,331 A | 10/1993 | Mausner |
| 5,260,065 A | 11/1993 | Mathur |
| 5,270,042 A | 12/1993 | Whitham |
| 5,276,058 A | 1/1994 | Satoh |
| 5,306,444 A | 4/1994 | Kitamura |
| 5,310,734 A | 5/1994 | Losch |
| 5,322,689 A | 6/1994 | Huges et al. |
| 5,322,839 A * | 6/1994 | Voegeli et al. ............... 514/21 |
| 5,352,443 A | 10/1994 | Kubo |
| 5,362,494 A | 11/1994 | Zysman |
| 5,364,886 A | 11/1994 | Loliger |
| 5,393,519 A | 2/1995 | Dowell |
| 5,397,497 A | 3/1995 | Jakobson |
| 5,407,675 A | 4/1995 | Etemad-Moghadam |
| 5,411,742 A | 5/1995 | Sebag |
| 5,427,814 A | 6/1995 | Löliger |
| 5,428,026 A | 6/1995 | Colarow |
| 5,438,044 A | 8/1995 | Losch |
| 5,439,672 A | 8/1995 | Zabotto |
| 5,443,839 A | 8/1995 | Meybeck |
| 5,443,840 A | 8/1995 | Morancais |
| 5,444,092 A | 8/1995 | Collins |
| 5,446,605 A | 8/1995 | Umehara |
| 5,466,452 A | 11/1995 | Whittle |
| 5,468,473 A | 11/1995 | Mullen |
| 5,498,420 A | 3/1996 | Mentrup Edgar |
| 5,503,832 A | 4/1996 | De Stoutz |
| 5,505,946 A | 4/1996 | Kennedy et al. |
| 5,510,391 A | 4/1996 | Elson |
| 5,523,308 A * | 6/1996 | Costanzo et al. ............ 514/317 |
| 5,539,129 A | 7/1996 | Zysman |
| 5,545,399 A | 8/1996 | Lee |
| 5,547,661 A | 8/1996 | Sun |
| 5,554,647 A | 9/1996 | Perricone |
| 5,565,439 A | 10/1996 | Piazza et al. |
| 5,565,493 A | 10/1996 | Nakata et al. |
| 5,567,420 A | 10/1996 | McEleney |
| 5,569,663 A | 10/1996 | Ribier |
| 5,571,503 A | 11/1996 | Mausner |
| 5,578,297 A | 11/1996 | Mellul |
| 5,589,181 A | 12/1996 | Bencsits |
| 5,595,984 A | 1/1997 | Blank |
| 5,597,814 A | 1/1997 | Blank |
| 5,601,833 A | 2/1997 | Roboer |
| 5,603,949 A | 2/1997 | Meybeck |
| 5,605,894 A | 2/1997 | Blank |
| 5,607,666 A | 3/1997 | Masson |
| 5,607,692 A | 3/1997 | Ribier |
| 5,614,180 A | 3/1997 | Chung |
| 5,614,215 A | 3/1997 | Ribier |
| 5,616,572 A | 4/1997 | Blank |
| 5,618,522 A | 4/1997 | Kaleta |
| 5,620,692 A | 4/1997 | Potter |
| 5,622,690 A | 4/1997 | Potter |
| 5,626,868 A | 5/1997 | Morancais |
| 5,629,015 A | 5/1997 | Ribier |
| 5,629,301 A | 5/1997 | Blank |
| 5,631,318 A | 5/1997 | Ito |
| 5,635,165 A | 6/1997 | Panitch |
| 5,637,316 A | 6/1997 | Ribier |
| 5,639,785 A | 6/1997 | Kung |
| 5,641,509 A | 6/1997 | Gross |
| 5,643,583 A | 7/1997 | Voultoury |
| 5,643,587 A | 7/1997 | Scancarella |
| 5,643,601 A | 7/1997 | Gross |
| 5,650,166 A | 7/1997 | Ribier |
| 5,652,230 A | 7/1997 | Blank |
| 5,653,988 A | 8/1997 | Gerber |
| 5,660,853 A | 8/1997 | Hansenne-Richoux |
| 5,665,367 A | 9/1997 | Burger |
| 5,670,547 A | 9/1997 | Milstein et al. |
| 5,674,511 A | 10/1997 | Kacher |
| 5,676,935 A | 10/1997 | Mellul |
| 5,676,956 A | 10/1997 | Duffy |
| 5,679,374 A | 10/1997 | Fanchon |
| 5,681,571 A | 10/1997 | Homgren et al. |
| 5,681,852 A | 10/1997 | Bissett |
| 5,683,683 A | 11/1997 | Scafidi |
| 5,686,102 A | 11/1997 | Gross |
| 5,688,763 A | 11/1997 | Hammonds, Jr. et al. |
| 5,691,327 A | 11/1997 | Blank |
| 5,712,356 A | 1/1998 | Bothe et al. |
| 5,723,148 A | 3/1998 | Love |
| 5,730,972 A | 3/1998 | Simon et al. |
| 5,741,496 A | 4/1998 | Khaiat |
| 5,741,766 A | 4/1998 | Marion et al. |
| 5,753,612 A | 5/1998 | Mitrani |
| 5,755,814 A | 5/1998 | Berg |
| 5,762,916 A | 6/1998 | Ansmann |
| 5,766,628 A | 6/1998 | Nurnberg |
| 5,776,917 A | 7/1998 | Blank |
| 5,780,456 A | 7/1998 | Blank |
| 5,780,457 A | 7/1998 | Blank |
| 5,780,458 A | 7/1998 | Blank |
| 5,780,459 A | 7/1998 | Blank |
| 5,786,345 A | 7/1998 | Blank |
| 5,786,346 A | 7/1998 | Blank |
| 5,789,396 A | 8/1998 | Blank |
| 5,795,879 A | 8/1998 | Blank |
| 5,801,163 A | 9/1998 | Blank |
| 5,804,216 A | 9/1998 | Terren |
| 5,807,545 A | 9/1998 | Coffindaffer |
| 5,824,702 A | 10/1998 | Wei |
| 5,833,965 A | 11/1998 | Sun |
| 5,834,013 A | 11/1998 | Ribier |
| 5,834,513 A | 11/1998 | Ptchelintsev |
| 5,840,717 A | 11/1998 | Blank |
| 5,843,907 A | 12/1998 | Sakai et al. |
| 5,843,926 A | 12/1998 | Blank |
| 5,863,546 A | 1/1999 | Swinehart |
| 5,869,031 A | 2/1999 | Tarroux et al. |
| 5,869,470 A | 2/1999 | Blank |
| 5,871,743 A | 2/1999 | Chajuss |
| 5,871,823 A | 2/1999 | Anders et al. |
| 5,880,314 A | 3/1999 | Shinomiya |
| 5,885,593 A | 3/1999 | Epstein |
| 5,885,596 A | 3/1999 | Parab |
| 5,885,600 A | 3/1999 | Blum |
| 5,885,617 A | 3/1999 | Jordan |
| 5,885,948 A | 3/1999 | Glenn |
| 5,888,522 A | 3/1999 | Pickart |
| 5,908,618 A | 6/1999 | Lorant |
| 5,912,175 A | 6/1999 | Wille, Jr. |
| 5,916,577 A | 6/1999 | Golz |
| 5,928,654 A | 7/1999 | Duranton |
| 5,928,658 A | 7/1999 | Kishida |
| 5,928,889 A | 7/1999 | Bakich |
| 5,936,052 A | 8/1999 | Bothe et al. |
| 5,942,479 A | 8/1999 | Frankenback |
| 5,945,095 A | 8/1999 | Mougin |
| 5,945,109 A | 8/1999 | Schmidt |
| 5,952,373 A | 9/1999 | Lanzendorfer |
| 5,958,387 A | 9/1999 | Bara |
| 5,961,980 A | 10/1999 | Kennedy |
| 5,962,015 A | 10/1999 | Delrieu |
| 5,962,441 A | 10/1999 | Blank |
| 5,965,153 A | 10/1999 | Allen |
| 5,965,750 A | 10/1999 | Oonishi et al. |

| | | | |
|---|---|---|---|
| 5,972,355 A | 10/1999 | Knight et al. | |
| 5,981,450 A | 11/1999 | Fabry | |
| 5,985,338 A | 11/1999 | Suh | |
| 5,985,809 A | 11/1999 | Frankenbach | |
| 5,990,291 A | 11/1999 | Waggle | |
| 6,004,915 A | 12/1999 | Elliott | |
| 6,013,250 A | 1/2000 | Cannell | |
| 6,013,255 A | 1/2000 | Edens | |
| 6,017,549 A | 1/2000 | Knight et al. | |
| 6,017,893 A | 1/2000 | Segelman | |
| 6,018,001 A | 1/2000 | Hiratani et al. | |
| 6,019,962 A | 2/2000 | Rabe | |
| 6,030,931 A | 2/2000 | Vinski | |
| 6,033,680 A | 3/2000 | Dixon | |
| 6,045,779 A | 4/2000 | Mueller | |
| 6,048,520 A | 4/2000 | Hoshowski | |
| 6,051,602 A | 4/2000 | Bissett | |
| 6,054,137 A | 4/2000 | Breton | |
| 6,060,070 A | 5/2000 | Gorbach | |
| 6,063,398 A | 5/2000 | Gueret | |
| 6,093,411 A | 7/2000 | Bissett | |
| 6,096,327 A | 8/2000 | Lezdey et al. | |
| 6,126,933 A | 10/2000 | Warne et al. | |
| 6,180,662 B1 | 1/2001 | Lanzendorfer | |
| 6,183,761 B1 | 2/2001 | Bissett | |
| 6,183,762 B1 | 2/2001 | Deckers et al. | |
| 6,238,678 B1 | 5/2001 | Oblong et al. | |
| 6,248,350 B1 | 6/2001 | Mori et al. | |
| 6,261,603 B1 | 7/2001 | McElwain | |
| 6,323,219 B1 * | 11/2001 | Costanzo | 514/317 |
| 6,399,083 B1 | 6/2002 | Pillai et al. | |
| 6,423,747 B1 | 7/2002 | Lanzendörfer | |
| 6,433,025 B1 | 8/2002 | Lorenz | |
| 6,447,809 B1 | 9/2002 | Krumhar et al. | |
| 6,461,627 B1 | 10/2002 | Ichioka | |
| 6,544,531 B1 | 4/2003 | Cole et al. | |
| 6,555,143 B2 | 4/2003 | Miller et al. | |
| 6,558,656 B2 | 5/2003 | Mann | |
| 6,750,229 B2 * | 6/2004 | Seiberg et al. | 514/317 |
| 2001/0031281 A1 | 10/2001 | Kung et al. | |
| 2002/0034489 A1 | 3/2002 | Wiegland | |
| 2002/0035046 A1 | 3/2002 | Lukenbach | |
| 2002/0042380 A1 | 4/2002 | Casteil et al. | |
| 2002/0064560 A1 | 5/2002 | Kung et al. | |
| 2002/0160061 A1 | 10/2002 | Saliou et al. | |
| 2002/0160062 A1 | 10/2002 | Liu et al. | |
| 2002/0160063 A1 | 10/2002 | Miller et al. | |
| 2002/0182166 A1 | 12/2002 | Martin | |
| 2002/0192313 A1 | 12/2002 | Saliou et al. | |
| 2002/0197244 A1 | 12/2002 | Seiberg et al. | |
| 2003/0064048 A1 | 4/2003 | Seiberg et al. | |
| 2003/0064049 A1 | 4/2003 | Seiberg et al. | |
| 2003/0176366 A1 | 9/2003 | Casteil et al. | |
| 2003/0219392 A1 | 11/2003 | Kung et al. | |
| 2003/0224075 A1 | 12/2003 | Liu et al. | |
| 2004/0009142 A1 | 1/2004 | Zambaux | |
| 2004/0062731 A1 | 4/2004 | Seiberg et al. | |
| 2004/0063593 A1 | 4/2004 | Wu et al. | |
| 2004/0067244 A1 | 4/2004 | Friedman | |
| 2005/0008665 A1 | 1/2005 | Batzer | |
| 2005/0019279 A1 | 1/2005 | Goppel | |
| 2005/0281776 A1 | 12/2005 | Courcoux | |
| 2007/0009459 A1 | 1/2007 | Magnant | |
| 2007/0041931 A1 | 2/2007 | Morelli | |

FOREIGN PATENT DOCUMENTS

| | | | |
|---|---|---|---|
| AU | 695806 B | 8/1998 | |
| CN | 1081899 A | 2/1994 | |
| CN | 1146876 A | 4/1997 | |
| CN | 1166960 A | 12/1997 | |
| DE | 4432947 A | 3/1996 | |
| DE | 19634206 A | 3/1998 | |
| DE | 19818849 A | 10/1998 | |
| EP | 0273202 B1 | 6/1951 | |
| EP | 0421021 | 6/1989 | |
| EP | 0 341 745 A1 | 11/1989 | |
| EP | 0 393 532 A2 | 10/1990 | |
| EP | 0 476 311 A1 | 3/1992 | |
| EP | 0473502 | 3/1992 | |
| EP | 0473502 A1 | 3/1992 |
| EP | 0 508 886 A1 | 10/1992 |
| EP | 0 574 352 A1 | 12/1993 |
| EP | 0 581 624 A1 | 2/1994 |
| EP | 0 581 624 B1 | 2/1994 |
| EP | 0 582 239 A1 | 2/1994 |
| EP | 0 582 239 B1 | 2/1994 |
| EP | 0 643 083 A1 | 3/1995 |
| EP | 0 643 960 A1 | 3/1995 |
| EP | 0 655 470 A1 | 5/1995 |
| EP | 273202 | 6/1995 |
| EP | 0 661 037 A1 | 7/1995 |
| EP | 0707851 | 4/1996 |
| EP | 0707851 A2 | 4/1996 |
| EP | 0707851 A3 | 4/1996 |
| EP | 0 713 106 A1 | 5/1996 |
| EP | 0 758 687 A1 | 2/1997 |
| EP | 0774249 | 5/1997 |
| EP | 0774249 A2 | 5/1997 |
| EP | 0 814 116 A1 | 12/1997 |
| EP | 0811595 | 12/1997 |
| EP | 0811595 A1 | 12/1997 |
| EP | 0 832 647 A1 | 4/1998 |
| EP | 0 852 946 A2 | 7/1998 |
| EP | 0 963 761 A1 | 12/1999 |
| EP | 0 998 914 A1 | 5/2000 |
| EP | 1 072 259 A2 | 1/2001 |
| EP | 1 074 240 A2 | 2/2001 |
| EP | 1077 063 A2 | 2/2001 |
| EP | 1 145 710 A1 | 10/2001 |
| EP | 1 166 763 A1 | 1/2002 |
| EP | 1 192 938 A2 | 4/2002 |
| EP | 1 210 946 A | 6/2002 |
| EP | 1 236 402 A2 | 9/2002 |
| EP | 1 236 465 A2 | 9/2002 |
| EP | 1 348 441 A | 10/2003 |
| EP | 1 352 637 A1 | 10/2003 |
| EP | 1 648 278 A | 4/2006 |
| FR | 2 596 986 A1 | 10/1987 |
| FR | 2 641 696 A2 | 7/1990 |
| FR | 2 685 202 A1 | 6/1993 |
| FR | 2 803 747 | 7/2001 |
| FR | 2 803 747 A1 | 7/2001 |
| FR | 2 811 226 | 1/2002 |
| FR | 2 811 226 A1 | 1/2002 |
| GB | 1098951 A | 1/1968 |
| JP | 6-2036304 A | 2/1967 |
| JP | 58-225003 | 6/1982 |
| JP | 58-225003 | 12/1983 |
| JP | 60061513 A | 4/1985 |
| JP | 63-68512 | 9/1986 |
| JP | 63-316711 | 6/1987 |
| JP | 196106 | 10/1987 |
| JP | 63-68512 | 3/1988 |
| JP | 63-96120 | 4/1988 |
| JP | 63-68512 | 8/1988 |
| JP | 63-227515 | 9/1988 |
| JP | 1093519 A | 4/1989 |
| JP | 1096106 A | 4/1989 |
| JP | 3-127713 | 10/1989 |
| JP | 02-286165 A | 11/1990 |
| JP | 4-169514 | 11/1990 |
| JP | 3-127713 | 5/1991 |
| JP | 5-320061 | 5/1991 |
| JP | 5-320024 | 5/1992 |
| JP | 4-169514 | 6/1992 |
| JP | 04283518 | 10/1992 |
| JP | 5015574 A | 1/1993 |
| JP | 5-114905 | 5/1993 |
| JP | 5114905 A | 5/1993 |
| JP | 5-213729 | 8/1993 |
| JP | 5-246932 | 9/1993 |
| JP | 5-320024 | 12/1993 |
| JP | 899891 | 1/1994 |
| JP | 6145061 A | 5/1994 |
| JP | 7304655 | 5/1994 |
| JP | 812560 | 6/1994 |
| JP | 8-020597 | 7/1994 |
| JP | 8-20597 | 7/1994 |

| | | | |
|---|---|---|---|
| JP | 6192085 A | 7/1994 |
| JP | 6256156 A | 9/1994 |
| JP | 06256156 A * | 9/1994 |
| JP | 7010772 A | 1/1995 |
| JP | 925212 | 7/1995 |
| JP | 925214 | 7/1995 |
| JP | 7196527 A | 8/1995 |
| JP | 7196529 A | 8/1995 |
| JP | 7304655 A | 11/1995 |
| JP | 8012560 A | 1/1996 |
| JP | 8040824 A | 2/1996 |
| JP | 8059450 A | 3/1996 |
| JP | 8-099821 | 4/1996 |
| JP | 8143442 A | 6/1996 |
| JP | 8143442 B | 6/1996 |
| JP | 8333260 A | 12/1996 |
| JP | 9-025214 | 1/1997 |
| JP | 9025212 A | 1/1997 |
| JP | 9025213 A | 1/1997 |
| JP | 9025214 A | 1/1997 |
| JP | 9077638 A | 3/1997 |
| JP | 10-139654 A | 5/1998 |
| JP | 10120542 A | 5/1998 |
| JP | 10120542 H | 5/1998 |
| JP | 10139654 A * | 5/1998 |
| JP | 63135310 A | 6/1998 |
| JP | 410226642 A | 8/1998 |
| JP | 2000-351720 A | 12/2000 |
| JP | 2004-000019 A | 1/2004 |
| KR | 92-8851 | 10/1992 |
| KR | 92-8851 B1 | 10/1992 |
| KR | 92-8853 B | 10/1992 |
| KR | 9176033 A | 7/1997 |
| RU | 2066992 | 9/1996 |
| RU | 2066992 C1 | 9/1996 |
| WO | 59187756 A | 10/1984 |
| WO | 62036304 A | 2/1987 |
| WO | WO 87/07838 A1 | 12/1987 |
| WO | WO 91/04283 A1 | 4/1991 |
| WO | WO 91/07166 | 5/1991 |
| WO | WO 92/09639 A2 | 6/1992 |
| WO | WO 92/09650 A1 | 6/1992 |
| WO | WO 94/06485 A1 | 3/1994 |
| WO | WO 94/07462 A | 4/1994 |
| WO | WO 95/04609 A1 | 2/1995 |
| WO | WO 95/09002 A1 | 4/1995 |
| WO | WO 95/09011 A1 | 4/1995 |
| WO | WO 95/24885 A1 | 9/1995 |
| WO | WO 96/09806 A2 | 4/1996 |
| WO | WO 96/19483 | 6/1996 |
| WO | WO 96/19491 | 6/1996 |
| WO | WO 96/24371 | 8/1996 |
| WO | WO 96/24392 A1 | 8/1996 |
| WO | WO9624371 | 8/1996 |
| WO | WO 96/29050 A | 9/1996 |
| WO | WO 96/30035 | 10/1996 |
| WO | WO 96/30396 | 10/1996 |
| WO | WO96/31194 | 10/1996 |
| WO | WO 96/31194 | 10/1996 |
| WO | WO 96/37497 | 11/1996 |
| WO | WO 96/40121 A1 | 12/1996 |
| WO | WO 96/40199 A1 | 12/1996 |
| WO | PCT/US 97/11033 | 3/1997 |
| WO | WO 97/11033 | 3/1997 |
| WO | WO 97/18904 A1 | 5/1997 |
| WO | 97/35998 * | 10/1997 |
| WO | WO 97/35998 | 10/1997 |
| WO | WO 97/39733 A1 | 10/1997 |
| WO | WO 98/01107 A1 | 1/1998 |
| WO | WO 98/02134 | 1/1998 |
| WO | WO 98/02138 A1 | 1/1998 |
| WO | WO 98/05333 | 2/1998 |
| WO | WO 98/08503 | 3/1998 |
| WO | WO 98/09987 | 3/1998 |
| WO | WO 98/17246 A1 | 4/1998 |
| WO | WO 98/33089 A1 | 7/1998 |
| WO | WO 98/49153 | 11/1998 |
| WO | WO 99/00110 A1 | 1/1999 |
| WO | WO 99/04752 A2 | 2/1999 |
| WO | WO 99/09065 | 2/1999 |
| WO | WO 99/09065 A1 | 2/1999 |
| WO | WO 99/15917 A1 | 4/1999 |
| WO | WO 99/24003 | 5/1999 |
| WO | WO 99/30729 A1 | 6/1999 |
| WO | WO 99/36050 | 7/1999 |
| WO | WO 99/39682 A2 | 8/1999 |
| WO | WO 99/57178 A1 | 11/1999 |
| WO | 11346695 A | 12/1999 |
| WO | WO00/15188 | 3/2000 |
| WO | WO 00/15188 | 3/2000 |
| WO | WO 00/43049 A1 | 7/2000 |
| WO | WO 00/51554 A2 | 9/2000 |
| WO | WO 00/51554 A3 | 9/2000 |
| WO | WO 00/62740 A2 | 10/2000 |
| WO | WO 00/62740 A3 | 10/2000 |
| WO | WO 00/62741 A2 | 10/2000 |
| WO | WO 00/62741 A3 | 10/2000 |
| WO | WO 00/62743 A2 | 10/2000 |
| WO | WO 00/62743 A3 | 10/2000 |
| WO | WO 00/62744 A2 | 10/2000 |
| WO | WO 00/62744 A3 | 10/2000 |
| WO | WO 00/62745 | 10/2000 |
| WO | WO 00/62745 A3 | 10/2000 |
| WO | WO 00/69404 | 11/2000 |
| WO | WO 00/69404 A1 | 11/2000 |
| WO | WO 00/69406 | 11/2000 |
| WO | WO 00/69406 A1 | 11/2000 |
| WO | WO 00/69407 | 11/2000 |
| WO | WO 00/69407 A1 | 11/2000 |
| WO | WO 00/69408 | 11/2000 |
| WO | WO 00/69408 A1 | 11/2000 |
| WO | WO 00/74699 A | 12/2000 |
| WO | WO 01/34909 A1 | 5/2001 |
| WO | WO 01/34909 A | 5/2001 |
| WO | WO 01/35920 A1 | 5/2001 |
| WO | WO 02/07697 A | 1/2002 |
| WO | WO 02/07697 A1 | 1/2002 |
| WO | WO 02/064104 A | 8/2002 |
| WO | WO 02/067988 A2 | 9/2002 |
| WO | WO 02/074280 A | 9/2002 |
| WO | WO 03/032941 A | 4/2003 |
| WO | WO 03/039502 A | 5/2003 |
| WO | WO 2004/022024 A | 3/2004 |
| WO | WO 2005/097216 A | 10/2005 |

OTHER PUBLICATIONS

Amino Acid Sequences of Double-headed Proteinase Inhibitors from the Seeds of *Canavalia lineata*, Shigeyuki Terada: Biosci. Biotech. Biochem. vol. 58, (2) 376-379 (1994).
A Serine Protease From Suspension-Cultured soybean Cells, Ze-Jian Guo: Phytochemistry, vol. 47, No. 4 (1998) 547-553.
Astrocytes Regulate Microglial Phagocytosis of Senile Plaque Cores of Alzheimer's Disease. DeWitt, David A., Institute of Pathology, 1998 pp. 329-340.
Aqueous Ethanol Extraction of Soybean Trypsin Inhibitors and Characterization of a Calcium-Sensitive: Keshun Liu, Journal of Food Biochemistry 15 (1991) 159-168.
Cardiovascular and Renal Small molecule direct thrombin inhibitors, Wiley and Fisher, Ashley Publications, Ltd., 1997, pp. 1265-1282.
Chemistry and Nutritional value of soybean components. In: Soybeans, chemistry, technology and utilization. Liu, K., pp. 32-35 (Aspen publishers, Inc., Gaithersburg, MD, 1999).
Correlation Between Endogenous Glutathione R. M. Tyrrell and M. Pidoux, Photochem. Photobiol. 47:405-412 (1988).
Cosmetics, Science and Technology, 2nd Edition, Sagarin, vol. 1, pp. 32-43 (1972).
Cosmetics, Science and Technology, 2nd Edition, Sagarin, vol. 1, pp. 72-73 (1972).
Common Disorders of Pigmentation. Hacker, Steven M., Postgraduate Medicine. 1996, pp. 177-186.
Cell-Marix Interactions in the Genesis of Arteriosclerosis and Alateroma (Effect of Aging). Robert, L., et al. Laboratorie de Biologie du Tissu Conjonctif 1992, pp. 331-341.
"Chemopreventive Agents: Protease Inhibitors," Ann R. Kennedy, Department of Radiation Oncology, University of PA School of Medicine, Philadelphia, PA 19104, USA Pharmacol. Ther. 78(3):167-209, 1998, Copyright 1998 Elsevier Science Inc.

Current Protocols in Cell Biology, Edited by Juan S. Bonifacino et al. Chapter 6: Electrophoresis and Immunoblotting. Copyright 1999 by John Wiley & Sons, Inc.

Defining Food Components as New Nutrients, Suzanne Hendrick: American Institute of Nutrition (1994) 1789S-1792S.

Depletion of Cutaneous Glutathione by Ultraviolet Radiation M. J. Connor and L. A. Wheeler, Photochem. Photobiol. 46:239-246 (1987).

Differential Regulation of Human Keratinocyte Growth and Differentiation by a Novel Family of Protease-activated Receptors, Claudia Derian; Cell Growth & Differentiation vol. 8, 743-749, Jul. 1997.

Diazepam Inhibits Phagocytosis and Killing Exerted by Polymorphonuclear Cells and Monocytes From Healthy Donors. Abstract. Immunopharmacology and Immunotoxicology (1989) pp. 70I-714.

Do Microglial Cells Phagocyte the B/A4-Amyloid Senile Plaque Core of Alzheimer Diesease? Hachimi, K. et al., Academy of Science, Paris. 1994, pp. 445-451.

Effect of Heat Treatments on Trypsin/Chyomotrypsin Inhibitor Activity of Red Gram (*Cajanus cajan* L.), V.H. Mulimani: Plant Foods for Human Nutrition, vol. 46, No. 2, (1994) 103-107.

Effects of heat treatment and germination on trypsin and chymotrypsin inhibitory activities in Sorghum (*Sorghum bicolor* (L.) Moench) seeds, V.H. Mulimani: Plant Foods for Human Nutrition, vol. 44, No. 3 (1993) 221-226.

Evaluation of the Effects of Hair Re-growth Agents on Lengthening the Anagen Phase Period and Blockade of Anagen phase-Catagen phase Transformation, Kazuto, J. Soc. Cosmet. Chem Japan, vol. 31 No. 4(1997):413-419.

Fluorescence Assay to Monitor Phagocytosis by Blood-Clot Derived Polymorphonuclear Leucocytes Study of Patients With Diabetes and Phagocytosis of Different *Staphyloccoccal* Species. Muxclow, C. Elizabeth et al., Mount Sinai Hospital, 1991, pp. 15-24.

"Evidence for the Presence of a Protease-Activated Receptor Distinct from the Thrombin Receptor in Human Keratinocytes" R.J. Santulli et al. Proceeding of the National Academy of Sciences of USA, vol. 92, Sep. 1995, pp. 9151-9155.

Glutathione, Ascorbate, and Cellular Protection A. Meister, Cancer Res. 54:1969s-1975s (1994).

"Glucocorticoid Effect on Hair Growth Initiation: A Reconsideration," Stenn, et al., 6 Skin Pharmacol. , 125-134 (1993).

Handbook of Non-Invasive Methods and the Skin, eds. J. Serup & G. Jemec, Chapter 14.3 (1995).

High-Performance Liquid Chromatographic Analysis of Phytoestrogens in Soy Protein Preparations with Ultraviolet Electrochemical and Thermospray Mass spectrometric Detection, K.D. R. Setchell: Journal of Chromotography 386 (1987) 315-323.

Immunologic Aspects of Lung Diseases and Cystic Fibrosis. Greenberger, Paul A. Jama, 1997, pp. 1924-1930.

Inflammation in Acne Vulgaris. Webster, Guy F., Jefferson Medical College. 1995, pp. 247-253.

"Interactions of Mast Cell Tryptase with Thrombin Receptors and PAR-2" M. Molino et al. Journal of Biological Chemistry, vol. 272, No. 7, Feb. 14, 1997 pp. 4043-4049.

Isolation and Properties of Anionic Protease Inhibitors from Buckwheat Seeds, Y.E. Dunavsky: Biochemistry and Molecular Biology International, vol. 40, No. 1, (1996) 1999-208.

Intercellular Adhesion Molecule-1. Van de Stope, A., et al. University Hospital Nijmegen, The Netherlands. 1996 pp. 13-33.

Influence of Nonionic Liposomal Composition on Topical Delivery of Peptide Drugs into Pilosebaceous Units:An in Vivo Study Using the Hamster Ear Model; Pharmaceutical Research, vol. 12, No. 8, 1995 p. 1184-1188.

"Inhaled Tryptase Causes Bronchoconstriction in Sheep Via Histamine Release" Jussara F. Molinari, Mario Scuri, William R. Moore, James Clark, Richard Tanaka, and William M. Abraham, Division of Pulmonary Disease, University of Miami at Mount Sinai Medical Center, Miami Beach, Florida and the Arris Pharmaceutical Corporation, South San Francisco, CA, , am J Respir Crit Care Med vol. 154 pp. 649-653, 1996.

Inhibition of Serine Proteases of the Blood Coagulation System by Squash Family Protease Inhibitors, Kaeko Hayaski: J. Biochem. 116, 1013-1018 (1994).

Interaction of Proteases with Legume Seed Inhibitors. Molecular features, Dinah S. deSeidl: Archivos Latinoamericanos de Nutricion, vol. 44 No. 4-S (1994) 21-S-25-S.

Inflammatory and Immune Responses are Impaired in Mice Deficient in Intercellular Adhesion Molecule I. Sligh, James E., et al. Proc. Natl. Acad., Sci. 1993, pp. 8529-8533.

Identification of Potential Activators of Proteinase-Activated Receptor-2. Fox, Mark T., et al. Federation of European Biochemical Societies. 1997. pp. 267-269.

Kunitz-Type Soybean Trypsin Inhibitor Revisited,Song et al., J. Mol. Biol. 275:347-63 (1998).

"Liposomes—A Selective Drug Delivery System for the Topical Route of Administration; Gel Dosage Form", Mezei & Gulasekharam Journal of Pharmaceutics and Pharmacology, vol. 34 (1982), pp. 473-474.

"Liposomes as a Skin Drug Delivery System", Topics in Pharmaceutical Sciences Mezei, M., (D. D. Breimer and P. Speiser, eds.,), Elsevier Science Publishers B. V., New York, N.Y., 1985, pp. 345-358.

Leukocytosis, Monocytosis and Neutrophilla; Hallmarks of Severe Depression. Maes, M., et al. J. Psychiat. Res. 1992, pp. 125-134.

Mammalian tyrosinase: biosynthesis, processing and modulation by melanocyte stimulating hormone. Jimenez, M., Kameyama, K., Maloy, WL, Tomita Y., and hearing, V. Proc. Natl. Acad. Sci. USA (1988), 85:3830-34.

McCutcheon's Detergents and Emulsifiers, North American Edition, pp. 317-324 (1986).

Macrophage Uptake of Cholesterol-Containing Particles Derived From LDL and Isolated From Atherosclerotic Lesions. Hoff, H. F., et al. European Heart Jouenal, 1990, pp. 105-115.

Mid-Dermal Elastolysis; An Ultrastructural and Biochemical Study. Fimiani, M., et al., Siena University, 1995, pp. 152-157.

Neutrophil and Monocyte Phagocytosis in Depressed Patients. McAdams C., et al. Neuro-Psychopharmacol & Bio. Psychiat, 1998 pp. 971-984.

Nutrition Communique Soy: Just a Hill of Beans? Clare M. Hasler: Journal of women's Health, vol. 7, No. 5 (1998) 519-523.

Periodontal Disease, Diabetes, and Immune Response; A Review of Current Concepts. Grant-Theule, D., Peridontal Abstracts, vol. 44, No. 3, 1996:69-77.

Partial Purification and Characterization of a Novel Soybean Protease Which is Inhibited by Kunitz and Bowman-Birk Trypsin Inhibitors, Shimpei Morita, vol. 119, No. 4, 1996 p. 711-718.

Photocarcinogenesis and Inhibition of Intercellular Adhesion Molecular I Expression in Cells of DNA-Repair-Defective Individuals. Ahrens, C., et al. The National Academy of Sciences 1997, pp. 6837-6841.

Phytoestrogen Content of Processed Soybean Products, P.A. Murphy: Food Technology, vol. 1, 60-64 (1982).

Preservation of Cosmetics, F. Sharpell Chapter 51, p. 887-900, publicly available prior to Feb. 28, 2001.

Potent Thrombin Inhibitors That Probe the S Subsite; Tripeptide Transition State Analogues Based on a Heterocycle Activated Carbonyl Grup. Costanzo, Michael j., et al. J. Med. Chem. 1996, pp. 3039-3043.

Protease-Activated G Protein Coupled Receptors on Human Platelets and Endothelial Cells. Brass, Lawrence F., et al. University of Pennsylvania, 1997, pp. 234-241.

Protease Activated Receptors Start a Family. Couglin, shaun R., University of California, 1994, pp. 9200-9202.

Primary Structure of a Kunitz-Type Trypsin Inhibitor From Enterolobium Contortisiliquum Seeds, I.F.C. Batista: Phytochemistry vol. 41, No. 4, (1996) 1017-1022.

Protection Against UV-Induced Reactivr Intermediate, D. P. T. Steenvoorden, et al., Photochem Photobiol. 67:651-656 (1998).

Photoprotective Effect of Esterified Glutathione Against Ultraviolet B-Induced Sunburn Cell K. Hanada, et al., J. Invest. Dermatol. 108:727-730 (1997).

Protein Proteinase inhibitors in legume seeds—Overview, Yehudith Birk: Archivos Latinoamericanos de Nutricion, vol. 44, No. 4-S (1994) 26-S-30-S.

Refractory Periodontitis Associated With Abnormal Polymorphonuclear Leukocyte Phagocytosis and Cigarette Smoking. MacFarlane, Gordon, et al. J. Peridontal, Nov. 1992, University of Minneapolis, pp. 908-913.

"Single-Step Method of RNA Isolation by Acid Guanidinium Thiocyanate-Phenol-Chloroform Extraction," Piotr Chomczynski & Nicoletta Sacchi, Analytical Biochemistry 162, 156-159 (1987), Copyright 1987 by Academic Press, Inc.

Soy Intake and Cancer Risk: A Review of the InVitro and InVivo Data, Mark J. Messina: Nutrician and Cancer vol. 21, No. 2, (1994) 113-131.

Specific identification of an authentic tyrosinase clone. Jimenez, M., K., Maloy, WL, and Hearing, V. J. Biol. Chem. (1989) 264:3397-3403.

Subcellular Distribution of Tyrosinase and Tyrosinase-Related Protein-L; Implications for Melanosomal Biogenesis. Orlow, Seth J., et al. The Socieity for Investigative Dermatology, Inc. 1993, pp. 55-64.

The Complete Amino Acid Sequence of Rice Bran Trypsin Inhibitor: J. Biochem 102, 2970-306 (1987).

The biochemistry and nutrition group:30 years of research in a developing country, Abraham Levy Benshimol: Archivos LatinoAmericanos De Nutrician, vol. 44, No. 4-S, pp. 5-S-9-S (1994).

"The Bowman-Birk Inhibitor", Int. J. Pept. Protein Res. 25:113-131 (1985).

The Bowman Birk Inhibitor from Soybeans As an Anticarcinogenic Agent), Kennedy, Am. J. Clin. Neutr. 68:1406S-1412S (1998).

The Effect of a Drug-delivery System Consisting of Soybean Phosphatidyl Choline and Medium-chain Monoacylglycerol on the Intestinal Permeability of Hexarelin in the Rat, Urban Fagerholm: J. Pharm. Pharmacol (1998) 50: 467-473.

The Role of Proteolytic Enzymes in the Development of Pumonary Emphysema and Periodontal Disease. Travis, J., et al. University of Georgia and Institute of Molecular Biology. 1994, pp. S143-S146.

The Role of Neutrophil Elastase in Chronic Inflammation. Doring, Grd. Department of Genreal Hygiene and Environmental Hygiene, 1994, pp. 114-117.

The Use of Endogenous Antioxidants to Improve Photoprotection Steenvoorden et al., Journal of Photochemistry and Photobiology B:Biology 41 (1997) 1-10.

The Use of Thermospray Liquid Chromatography/Tandem Mass spectrometry for the Class Identification and Structural Verification of Phytoestrogens in Soy Protein Preparations, Robert J. Barbuch: Biomedical and Environmental Mass Spectrometry, vol. 18, (1989) 973-977.

Tryptase Inhibitors Block Allergen-induced Airway and Inflammatory Responses in Allergic Sheep, Warne, William R. Moore, and Richard D. Tanaka, Dept. of Molecular Pharmacology, Inflammation Program, Arris Pharmaceutical Corp, Souch San Francisco, CA, and Department of Research, Division of Pulmonary Diseases, University of Miami at Mount Sinai Medical Center, Miami Beach, Florida, Am J Respir Crit Care Med vol. 152. pp. 2076-2083, 1995.

Trypsin Inhibitor Polymorphism: Multigene Family Expression and Posttranslational Modification, Laurence Quillien: Journal of Protein Chemistry, vol. 16, No. 3 (1997) 195-203.

Trypsin Inhibitor Activity in Commercial Soybean Products in Japan, Yuko Miyagi: J. Nutr. Sci. Vitaminol (1997) vol. 43: 575-580.

Two Groups of Protease Inhibitors Functionally Active in Buckwheat Seeds, Yakov Dunaevsky: soba.shinshu-uac.jp/contents/105.html, publicly available prior to Feb. 28, 2001.

Wheat Germ Trypsin Inhiboors. Isolation and Structural Characterization of Single-Headed and Double-Headed Inhibitors of the Bowman-Birk Type: J. Biochem 100, 975-983 (1986).

The Joy of Soy: www.wheat-grass.com/851_oral_liquid.shtml, Wheatgrass Express, Inc. 1996.

"RQ1 RNase-Free DNASE, Promega," Technical Bulletin No. 518, pp. 1-4, Feb. 2000, Promega Corporation, 2800 Woods Hollow Rd, Madison, WI 53711-5399.

"Invitrogen Life Technologies, ThermoScript RNase H-Reverse Transcriptase," 2001, Invitrogen Corporation, www.invitrogen.com/content.cfm.

Leaflet from Ichimaru Pharcos issued Mar. 7, 1997 "Plant Extract Containing Female Hormone-Like Isoflavones".

Thrombin Inhibitors: Relevant Patent Applications as of Jul. 8, 1998 and Oct. 1, 1996.

Concerns Regarding Soybeans: www.rheumatic.org/soy.htm, publicly available prior to Feb. 28, 2001.

Soy Therapy, www.wiseessentials.com/soytherapy.html (Apr. 13, 2000).

Brochure on Lipoxydase Code 411784, Apr. 1999.

Chapter 8: Antithrombotics/Serine Protease; William Ripka and George Vlasuk, Covads International, San Diego, CA, publicly available prior to Feb. 28, 2001.

Helena Rubinstein Whitening with Soybean? HR has launched "Future White" in Japan, publicly available prior to Feb. 28, 2001.

"Isoral" Soybean power makes your skin clear and moist—Brochure, publicly available prior to Feb. 28, 2001.

Elhibin—Brochure, Centerchem, Inc., publicly available prior to Feb. 28, 2001.

Avon's Anew Positivity Trio Targets Menopausal Women, The Rose Sheet, Feb. 28, 2000, p. 8.

Soybean Technology Improves Skin, Allured's Cosmetics & Toiletries Magazine vol. 115, No. 3, Mar. 2000, p. 22.

Nudit—Advertisement, publicly available prior to Feb. 28, 2001.

Anti-regrowth effect of hair, Dec. 22, 1998, pp. 11-13.

"CaspACE Assay System, Colorimetric," Product Improvements, Neural Notes vol. V, Issue 1 1999, p. 13.

Abstracts of requested patent titles 1996.

Abstract for Product for Damaged hair by Bristol-Myers-Squibb, publicly available prior to Feb. 28, 2001.

Gastric Juice for antiaging—Abstracts 1997.

Soybeans for skin pigmentation—Abstracts 1997.

Soybeans for skin whitening—Chemical Abstracts 1997.

Plant extracts for skin whitening—Abstracts, publicly available prior to Feb. 28, 2001.

EnzChek™ Protease Assay Kits Product Information, Revised Mar. 15, 1999; Molecular Probes, Eugene OR.

Derwent Abstract of JP 8012560, "Dermal external preparation useful treat freckles sunburn contain extract copaiba useful skin melanocyte inhibit", Shiseido Co., Ltd. (Jan. 1996).

Derwent Abstract of JP 9025212, "External dermal agent contain protease inhibit contain extract plant belong family", Shiseido Co., Ltd. (Jan. 1997).

Derwent Abstract of Japan, JP 04169514, "Safe External Skin Agent White Skin Prevent Rough Skin Contain One Protease Inhibit Soy Trysin Inhibit One Ketose", Shiseido Co., Ltd. (Jun. 1992).

Derwent Abstract JP 09 059166, "Epithelial Cell Grown Promoter Useful as dermal agent comprises malonyl isoflavone glycoside . . ." Kikkoman Corp et al. (Mar. 1997).

Patent Abstract JP 62 036304, "Cosmetic" Kashiwa Kagaku Kogyo, KK (Feb. 1987).

Derwent XP002222884 Pure Natural Medicine Health Hair Shampo N. Wang, (Nov. 1994).

Derwent XP02222885 White Cosmetic Contain ISO Flavone Compound suppress formation melanin pigment, Ichimaru Pharcos (Dec. 1983.

Derwent XP002222886 "External Dermal Agent contain Protease Inhibit Contain Extract Plant" Shiseido Co. Ltd. Jan. 1997).

Derwent XP002222887 "Treat Hair Prevent Treat Hair Fall Alopecia Male White Hair Formation Ingestion Derivative Soy" Crescendo Corp. KK (Oct. 2000).

Chemical abstracts, Nov. 1995 Evidence for Presence of Protease-activiated receptor distinct from the thrombin receptor in human keratinocytes Sant7ulli et al.

U.S. Appl. No. 10/611,100, filed Jul. 1, 2003, Halas et al.
U.S. Appl. No. 10/659,598, filed Sep. 10, 2003, Seiberg et al.
U.S. Appl. No. 09/206,249, filed Dec. 7, 1998, Seiberg et al.
U.S. Appl. No. 09/677,511, filed Sep. 29, 2000, Liu et al.
U.S. Appl. No. 09/621,565, filed Jul. 20, 2000, Seiberg et al.
U.S. Appl. No. 10/434,309, filed May 8, 2003, Seiberg et al.
U.S. Appl. No. 09/698,454, filed Oct. 27, 2000, Seiberg et al.

Babiarz-Magee et al, "The Expression and Activation of Protease-Activated Receptor-2 Correlate with Skin Color", *Pigment Cell Res*, vol. 17 (2004) pp. 241-251.

Hermanns et al, "Unraveling the Patterns of Subclinical Pheomelanin-Enriched Facial Hyperpigmentation: Effect of Depigmenting Agents", *Dermatology*, vol. 201 (2000) pp. 118-122.

Liu et al, "Application of Soy in Skin Care", *Journal Nutr.*, vol. 132 (2002) pp. 574S.

Paine et al, "An Alternative Approach to Depigmentation by Soybean Extracts via Inhibition of the PAR-2 Pathway", *Journal Investivative Dermatology*, vol. 116 (2001) pp. 587-595.

Scott et al, "Protease-Activated Receptor 2, a Receptor Involved in Melanosome Transfer, is Upregulated in Human Skin by Ultraviolet Irradiation", *Journal Investigative Dermatology*, vol. 117 (2001) pp. 1412-1420.

Scott et al, "Proteinase-Activated Receptor-2 Stimulates Prostaglandin Production in Keratinocytes: Analysis of Prostaglandin Receptors on Human Melanocytes and Effects of PGE2 and PGF2α on Melanocyte Dendricity", *Journal Investigative Dermatology*, vol. 122 (2004) pp. 1214-1224.

Scott et al, "The Proteinase-Activated Receptor-2 Mediates Phagocytosis in a Pho-Dependent Manner in Human Keratinocytes", *Journal Investigative Dermatology*, vol. 121 (2003) pp. 529-541.

Seiberg et al, "Inhibition of Melanosome Transfer Results in Skin Lightening", *Journal Investigative Dermatology*, vol. 115 (2000) pp. 162-167.

Seiberg et al, "Soy Extracts Reduce Hair Growth and Hair Follicle Dimensions", *Hair Science and Technology*, D. Van Neste (editor) (2003) pp. 391-400.

Seiberg et al, "Soymilk Reduces Hair Growth and Hair Follicle Dimensions", *Experimental Dermatology*, vol. 10 (2001) pp. 405-423.

Seiberg et al, "The Protease-Activated Receptor 2 Regulates Pigmentation via Keratinocyte-Melanocyte Interactions", *Experimental Cell Research*, vol. 254 (2000) pp. 25-32.

Seiberg et al, "The Protease-Activated Receptor-2 Regulates Pigmentation via Melanosome Phagocytosis", *Mechanisms of Suntanning*, J. P. Ortonne and R. Ballotti (editors) (2002) pp. 215-278.

Seiberg et al, "The Regulation of Pigmentation by Serine Proteases and Their Inhibitors", Inhibition of Human Proteases: From Target Identification to Therapy, CHI Press (1998) pp. 1-3.

Seiberg, "Keratinocyte-Melanocyte Interactions During Melanosome Transfer", *Pigment Cell Res.*, vol. 14 (2001) pp. 236-242.

Sharlow et al, "The Protease-Activated Receptor-2 Upregulates Keratinocyte Phagocytosis", *Journal of Cell Science*, vol. 113 (2000) pp. 3093-3101.

Wang et al, "Effects of Soybean Trypsin Inhibitor on Digestive Physiology and Growth and Development of Helicoverpa armigera Larvae", *Acta Entomologica Sinica*, vol. 38, No. 3 (Aug. 1995) pp. 272-274.

Wilson et al, "Immunocytochemical Study of the Interaction of Soybean Trypsin Inhibitor with Rat Intestinal Mucosa", *Gut*, vol. 19 (1978) pp. 260-266.

"A Combined Soybean Crushing-Deordorizing System that Yields 100-200 Mesh Powder for Food Additive Use has been Developed by Shinyu Zoki Co. Ltd. And Mitsubishi Rayon Engineering Ltd.", *Tech Times*, pp. 10 (1978).

"Soy Protein Prevents Skin Tumors From Developing in Mice", *Gene Therapy Weekly*, ISSN 1078-2842, pp. 21 (Nov. 8, 2001).

Badash et al, "Effect of Gamma Irradiation of Field and Storage Fungi of Wheat, Maize and Soybean", *Chemie Mikrobiologie Technologie der Lebensmittel* (1992).

Blackheart et al, "Ligand Cross-Reactivity Within the Protease-Activated Receptor Family", *The Journal of Biological Chemistry*, vol. 271, No. 28, pp. 16466-16471 (1996).

Doolittle, "Proteins", *Reading from Scientific American—The Molecules of Life*, Chapter 4, pp. 38-47 (1985).

Ebling et al, "Hair", *Journal of Investigative Dermatology*, vol. 67, No. 1, pp. 98-105 (Jul. 1976).

Ebling, "Hair Follicles and Associated Glands as Androgen Targets", *Clinics in Endocrinology and Metabolism*, vol. 15, No. 2, pp. 319-339 (May 1986).

Galvez et al., "Chemopreventive Property of a Soybean Peptide (Lunasin) That Binds to Deacetylated Histones and Inhibits Acetylation", *Cancer Research*, vol. 61, No. 20, pp. 7473-7478 (Oct. 15, 2001).

Hafez et al, "Effects of Gamma Irradiation on Proteins and Fatty Acids of Soybean", *Journal of Food Science*, vol. 50 (1985) pp. 1271-1274.

Hattori et al, "Effects of sup.60 Co- gamma-rays on Defatted Soybean Powder", *Food Irradiation*, vol. 3, No. 1, pp. 104-110 (1968).

Hollenberg et al, "Proteinase-Activated Receptor-2 in Rat Aorta: Structural Requirements for Agonist Activity of Receptor-Activating Peptides", *Molecular Pharmacology*, vol. 49, pp. 229-233 (1996).

Itami et al, "Mechanism of Action of Androgen in Hair Follicles", Journal of Dermatological Science, 7 Suppl., S98-S103 (Jul. 1994).

Jingtian et al, "Studies of Soy Sauce Sterlization and its Special Flavour Improvement by Gamma-Ray Irradiation", *Radiation Physics and Chemistry*, vol. 31, Nos. 1-3, pp. 209-213 (1988).

Keeton et al, "The Chemistry of Life", *Biological Science*, Fourth Edition, Chapter 3, pp. 66-67 (1986).

Kennedy et al, "Prevention of Carcinogenesis by Protease Inhibitors", *Cancer Research*, vol. 54, No. 7 (Suppl), pp. 1999s-2005s (Apr. 1, 1994).

Kennedy, "The Evidence for Soybean Products as Cancer Preventive Agents", *The Journal of Nutrition*, vol. 125, No. 3 Suppl, pp. 733s-743s (Mar. 1995).

Kovacs et al, "Effect of Irradiation and Dielectric Heating on Soybean Ultrastructure, Trypsin Inhibitor, and Lipoxygenase Activities", *Food Structure*, vol. 10, pp. 217-227 (1991).

Lam et al, "Combined Effect of Irradiation and Dielectric Heating on Chemical Properties of Soybeans", *7th Symp. On Radiation Chemistry*, pp. 477-483 (1990).

Limtrakul et al, "Suppressive Effect of Soybean Milk Protein on Experimentally Induced Skin Tumor in Mice", *Life Sciences*, vol. 53 (1993) pp. 1591-1596.

Merck Index (12th Edition), Edited by Susan Budavari (1996) Thrombin., entry 9525, p. 1601.

Merck Index (12th Edition), Edited by Susan Budavari (1996) Trypsin, entry 9926, p. 1669.

Mysliborski et al, "Therapy for Acne Vulgaris", *Comprehensive Therapy*, vol. 7, No. 1, pp. 13-16 (Jan. 1981).

Odani et al. "Studies on Soybean Trypsin Inhibitors. XIII. Preparation and Characterization of Active Fragments from Bowman-Birk Proteinase Inhibitor", *Journal Biochem.*, vol. 83, No. 3, pp. 747-753 (1978).

Seiberg et al, "Trypsin-Induced Follicular Papilla Apoptosis Results in Delayed Hair Growth and Pigmentation", *Developmental Dynamics*, vol. 208, pp. 553-564 (1997).

Sessa et al, "Toasted Soybean Flour Components with Trypsin Inhibitor Activity", *JAOCS*, vol. 63, No. 6, pp. 784-788 (Jun. 1986).

Song et al, "PS04.01.44 Crystal Structure of the Complex of Porcine Pancreatic Trypsin with Kunitz-Type Soybean Trypsin Inhibitor", Crystallography of Biological Macromolecules, p. C-106, XVII Congress and General Assembly of the International Union of Crystallog, (1996) (www.bmsc.wahing...ts/abstracts/S0081.html).

Tan-Wilson, "Relevance of Multiple Soybean Trypsin Inhibitor Forms to Nutritional Quality", *Nutritional and Toxicological Significance of Enzyme Inhibitors in Foods*, Edited by Mendel Friedman, Chapter 22, pp. 391-411 (1985), Department of Biological Sciences, State University of New York at Binghamton.

Thornton et al, "Effect of Androgens on the Growth of Cultured Human Dermal Papilla Cells Derived from Beard and Scalp Hair Follicles", *The Journal of Investigative Dermatology*, vol. 97, No. 2, pp. 345-348 (Aug. 1991).

Van Den Broeke et al, "Topically Applied N-acetylcysteine as a Protector Against UVB-Induced Systemic Immunosuppression", *Journal of Photochemistry and Photobiology, B: Biology*, vol. 27, pp. 61-65 (1995).

Xiang et al, "A Study of Nexin 1 of Skin and Hair Follicle during Postnatal Development Period of Rat", Zhongguo Yi Xue Ke Xue Yaun Xue Bao, vol. 20, No. 2, pp. 127-132 (Apr. 1998) Abstract.

Yu et al, "Message of Nexin 1, a Serine Protease Inhibitor, is Accumulated in the Follicular Papilla During Anagen of the Hair Cycle", Journal of Cell Science, vol. 108, Pt 12 (Dec. 1995) pp. 3867-3874 Abstract.
European Search Report dated Jan. 7, 2005, for corresponding EP application 04255470.9.
http://www.faqs.org/health/Sick-V1/Acne.html.
Ogawa, "Current Problem of Research on Hair Growth Mechanisms and Hair Growth Promoters", Fragrance Journal, vol. 5, pp. 1-5 (1989).
UNIQEMA: "Pharmaceutical and Cosmetic Uses of Diolic Acids", *Research Disclosure*, Kenneth Mason Publications, Hampshire, GB, vol. 444, No. 77 (Apr. 2001.
Huang et al: "Inhibitory Effect of Topical Applications of Nondenatured Soymilk on the Formation and Growth of UVB-Induced Skin Tumors", *Oncology Research*, vol. 14 (2004) pp. 387-397.
http://familydoctor.org/online/famdocen/home/common/cancer/risk/159.html.
McGuire, "Activation of Epidermal Tyrosinase", *Biochemical and Biophysical Research Communications*, vol. 40, No. 5 (1970) pp. 1084-1089.
Relevance of Multiple Soybean Trypsin Inhibitor Forms to Nutritional Quality, Anna L. Tan-Wilson, Department of Biological Sciences, State University of New York at Binghamton, 391-411.
Nutritiion Communique Soy: Just a Hill of Beans? Clare M. Hasier: Journal of womens's Health, vol. 7, No. 5 (1998) 519-523.
Trypsin Inhibitor Activity in Comercial Soybean Products in Japan, Yuko Miyagi: J. Nutr. Sci. Vitaminol (1997) vol. 43: 575-580.
Soy-derived protease inhibitors treat cancer and inflammation, Louis J. Scotti: Windhover Information Inc. (1998).
Crystal Structure of the Complex of Porcine Pancreatic Trypsin with Kunitz-Type Soybean Trypsin Inhibitor, Hyun K. Song: www.bmsc.wahing...ts/abstracts/S0081.html.
Two Groups of Protease Inhibitors Functionally Active in Buckwheat Seeds, Yakov Dunaevsky: soba.shinshu-uac.jp/contents/105.html.
Isolation and Properties of Anionic Protease Inhibitors from Buckwheat Seeds, Y.E. Dunaevsky: Biochemistry and Molecular Biology International, vol. 40, No. 1, (1996) 199-208.
Effect of Heat Treatments on Trypsin/Chyomotrypsin Inhibitor Activity of Red Gram (*Cajanus cajan* L.), V.H. Mulimani: Plant Foods for Human Nutrition, vol. 46, No. 2, ((1994) 103-107.
The Joy of Soy: www.wheat-grass.com/851_oral_liquid.shtml.
Concerns Regarding Soybeans: www.rheumatic.org/soy.htm.
Evaluation of the Effects of Hair Re-growth substances on Elongation of Anagen Period and Blockade of Anagen-Catagen Transformation, Kazuto Hamada: J. Soc. Cosmet. Chem. Japan, vol. 31, No. 4 (1997) 1-3.
Current problem of research on hair growth mechanisms and hair growth promoters, Hideki Ogawa:Frangrance Journal (1985) vol. 5, 1-5.
Brochure for Anti-growth effect of hair: Dec. 22, 1998.
Phtoestrogen Content of processed Soybean Products, P.A. Murphy: Food Technology, vol. 1, 60-64 (1982).
Soy Therapy, www.wiseessentials.com/soytherapy.html (Apr. 13, 2000).
"CaspACE Assay System, Colorimetric," Product Improvements, Neural Notes vol. V, Issue 1 1999, p. 13.
"RQ1 RNase-Free DNASE, Promega," Technical Bulletin No. 518, pp. 1-4, Promega Corporation, 2800 Woods Hollow Rd, Madison, WI 53711-5399.
"Invitrogen Life Technologies, ThermoScript RNase H-Reverse Transcriptase," www.invitrogen.com/content.cfm.
Piotr Chomcyzynski & Nicoletta Sacchi, "Single-Step method of RNA Isolation by Acid Guanidinium Thiocyanate-Phenol-Chloroform Extraction," Analytical Biochemistry 162, 156-159 (1987), Copyright 1987 by Academic Press, Inc.
Ann R. Kennedy, Department of Radiation Oncology, University of PA School of Medicine, Philadelphia, PA 19104, USA, "Chemopreventive Agents: Protease Inhibitors," Pharmacol. Ther. 78(3):167-209, 1988, Copyright 1998 Elsevier Sceience Inc.
James M. Clark, William M. Abraham, Cindy E. Fishman, Rosanna Forteza, Ashfaq Ahmed, Alejandro Cortes, Robert L. Warne, William R. Moore, and Richard D. Tanaka, Dept. of Molecular Pharmacology, Inflammation Program, Arris Pharmaceutical Corp, Souch San Francisco, CA, and Department of Research, Division of Pulmonary Diseases, University of Miami at Mount Sinai Medical Center, Miami Beach Florida, Tryptase Inhibitors Block Allergen-induced Airway and Inflammatory Responses in Allergic Sheep, Am J Respir Crit Care Med vol. 152. pp. 2076-2083, 1995.
Jussara F. Molinari, Mario Scuri, William R. Moore, James Clark, Richard Tanaka, and William M. Abraham, Division of Pulmonary Disease, University of Miami at Mount Sinai Medical Center, Miami Beach, Florida and the Arris Pharmaceutical Corporation, South San Francisco, CA, "Inhaled Tryptase Causes Bronchoconstriction in Sheep Via Histamine Realease", am J Respir Crit Care Med vol. 154 pp. 649-653, 1996.
Differential Regulation of Human Kertinocyte Growth and Differentiation by a Novel Family of Protease-activated Receptors, Claudia Derian; Cell Growth & Differentiation vol. 8, 743-449, Jul. 1997.
Potent Thrombin Inhibitor That Probe the S1 Subsite; Tripeptide Transition State Analogues Based on a Heterocycle-Activated Carbonyl Group, Journal Medical Chem., 1996, 39, 3039-3043.
Chapter 8: Antithrombotics/Serine Protease; William Ripka and George Vlasuk, Covads International, San Diego, CA, 1999.
41USPQ2d, Hess v Advanced Cardiovascular Systems, Inc., pp. 1782-1788, 1997.
Helena Rubinstein Whitening with Soybean? HR has launched "Future Whie" in Japan, 1999.
"Isoral" Soybean power makes your skin clear and moist—Brochure, 1999.
Elhibin—Brochure, 2000.
Abstract for Product for Damaged hair by Bristol-Myers-Squibb, 2000.
Nudit—Advertisement, 2001.
Liposydase, Brochuret, 1999.
Anti-regrowth effect of hair, pp. 11-13, 1999.
Thrombin Inhibitors: Relevant Patent Applications as of Oct. 1, 1996.
Thrombin Inhibitors: Relevant Patent Applications as of Jul. 8, 1998.
Gastric Juice for antiaging—Abstracts.
Soybeans for skin pigmentation—Abstracts, 2001.
Soybeans for skin whitening—Chemical Sbstracts, 2000.
Plant extracts for skin whitening—Abstracts, 2000.
"Superscript II Reverse Transcriptase" protocol pub. by Gibco-BRL (now LifeTech Inc) Apr. 1992.
Abstract of JP07304655, 1997.
Abstract of WO9936050, 1999.
WO 99/40752 search report, 1999.
U.S. Appl. No. 09/361,426, filed Jul. 27, 1999.
Billings et al., Pro. Natl. Acad. Sci. 89:3120-3124 (1992) A Growth-regulated Protease Activity That is Inhibited by the Anticarcinogenic Bowen-Birk Protease Inhibitor.
Kennedy, Am. J. Clin. Neutr. 68:1406S-1412S (1998) The Bowman Birk Inhibitor from Soybeans As An Anticarcinogenic Agent).
Liu, K., Chemistry and Nutritional value of soybean components. In: Soybeans, chemistry, technology and utilization. pp. 32-35 (Aspen publishers, Inc., Gaithersburg, MD, 1999).
Song et al., J. Mol. Biol. 275:347-63 (1998) Kunitz-Type Soybean Trypsin Inhibitor Revisited.
"Liposomes—A Selective Drug Delivery System for the Topical Route of Adminstration; Gel Dosage Form", Journal of Pharmaceutics and Pharmacology, vol. 34 (1982), pp. 473-474.
(EnzChek™ Protease Assay Kits Product Information, revised Mar. 15, 1999; Molecular Probes, Eugene OR).
"Disinfection, sterilization, and preservation" 4th edition, Seymour S. Block, pp. 887-888 (1991, Lea & Febiger, Malvern, PA).
"Official Compendia of Standards, USP 24 USP/NF 19", United States Pharmacopeial Convention, Inc., 2000 (Broad of Trustees, United States Pharmacopeial Convention, Inc.).
"Official Methods of Analysis of AOAC International," edited by Patricia Cunniff, Sixteenth Edition, $5^{th}$ Revision, 1999 (AOAC International).
A. Meister, Cancer Res. 54:1969s-1975s (1994) Glutathinoe, Ascorbate, and Cellular Protection.

Current Protocol in Cell Biology, Edited by Juan S. Bonifacino et al. Chapter 6: Electrophoresis and Immnunoblotting. Copyright 1999 by John Wiley & Sons, Inc.

D. P. T. Steenvoorden, et al., Photochem Photobiol. 67:651-656 (1998) Protection Against UV-Induced Reactivr Intermediate.

Jimenez, M., K., Maloy WL, and Hearing, V. Specific Identification of an authentic tyrosinase clone. J. Biol. Chem. (1989) 264:3397-3403.

Jimenez, M., Kameyama, K., Maloy, WL, Tomita Y., and Hearing, V. Mammalian tyrosinase: biosynthesis, processing and modulation by melanocyte stimulating hormone, Proc. Natl. Acad. Sci. USA (1988), 85:3830-34.

K. Hanada, et al., J. Invest. Dematol. 108:727-730 (1997) Photoprotective Effect of Esterified Glutathione Against Ultraviolet B-Induced Sunburn Cell.

L. T. van den Broeke and G. M. J. Beijersbergen van Henegouwen, J. Photochem. Photobiol. B. Biol. 27:61-65 (1995).

M. J. Connor and L. A. Wheeler, Photochem. Photobiol. 46:239-246 (1987) Depletion of Cutaneous Glutathione By Ultraviolet Radiation.

Mezei & Gulasekharam, "Liposomes—A Selective Drug Delivery System for the Topical Route of Administration; Gel Dosage Form", Journal of Pharmaceutics and Pharmacology, vol. 34 (1982), pp. 473-474.

Mezei, M., "Liposomes as a Skin Drug Delivery System", Topics in Pharmaceutical Sciences (D. D. Breimer and P. Speiser, eds.,), Elsevier Science Publishers B. V., New York, N.Y., 1985, pp. 345-358.

R. M. Tyrrell and M. Pidoux, Photochem. Photobiol. 47:405-412 (1988) Correlation between Endogenous Glutathione.

Sagarin, Cosmetics, Science and Technology, 2nd Edition, vol. 1, pp. 32-43 (1972).

Sagarin, Cosmetics, Science and Technology, 2nd Edition, vol. 1, pp. 72-73 (1972).

Stenn, et al., "Glucocorticoid Effect on Hair Growth Initiation: A Reconsideration," 6 Skin Pharmacol. , 125-134 (1993).

Steenvoorden et al., "The Use of Endogenous Antioxidants to Improve Photoprotection" Journal of Photochemistry and Photobiology B:Biology 41 (1997) 1-10.

Chemical Abstracts, vol. 123, No. 21, Nov. 20, 1995 Columbus, Ohio, US; abstract No. 281641, XP002094580 & R.J. Santulli et al.: "Evidence for the presence of PAR.." Proc. Natl. Acad. Sci USA, vol. 92, No. 20, 1995, p. 9151-9155.

Derwent Abstract of JP 09 025214 A, 1995.
Derwent Abstract of JP 04 169514 A, 1998.
Derwent Abstract of JP 09 025212 A, 1997.
Derwent Abstract of JP 08 099891 A, 1996.
Derwent Abstract of JP 08 012560 A, 1998.

Diazepam Inhibits Phaagocytosis and Killing Exerted Polymorphonuclear Cells and Monocytes From Healthy Donors. Abstract Immunopharmacology and Immunotoxicology (1989) pp. 701-714.

Influence of Nonionic Lipsomal Composition on Topical Deliveyr of Peptide Drugs Into Pilosebaceous Units; An In Vivo Study Using the Hamster Ear Model. Niemiec, S., et al. Pharmaceutical Research, 1995, pp. 1184-1188.

Adhesion Molecule Expression in Normal Skin and Melanocytic Lesions. Tronnier, M., et al. Medical University of Lubeck, Germany. 1996 pp. 278-285.

Intecellular Adhesion Molecule-1. Van de Stope, A., et al. University Hospital Nijmegen, The Netherlands. 1996 pp. 13-33.

Periodontal Disease, Diabetes, and Immune Response; A Review of Current Concepts. Grant-Theule, D.

Refractory Periodontitis Associated With Abnormal Polymorphonuclear Leukocyte Phagocytosis and Cigarette Smoking. MacFarlane, Gordon, et al. University of Minneapolis, pp. 908-913.

The Role of Preteolytic Enzymes in the Development of Pumonary Emphysema and Periodontal Disease. Travis, J., et al. University of Georgia and Institute of Molecular Biology. 1994, pp. S143-S146.

Abstract of S62255292—1992.
Abstract JP 87255292—1993.

Preservation of Cosmetics, F. Sharpell Chapter 51, p. 887-900,— (1983).

Abstract JP 62036304—1995.

Pending U.S. Appl. No. 09/361,426, filed Jul. 27, 1999, Johnson & Johnson.

EPO communication dated Jul. 13, 2002reporting on substantive examination for European Patent Application No. 98939062.0 citing references.

European Search Report, dated Dec. 30, 2002, for European Appln. No. 00306352.6.

European Search Report dated Dec. 17, 2002 for European Appln. No. 00306350.0.

China Patent Agent Ltd. correspondence Oct. 23, 2002 citing references in office action issued on Aug. 30, 2002 re: Chinese Patent Application No. 98801022.4.

* cited by examiner

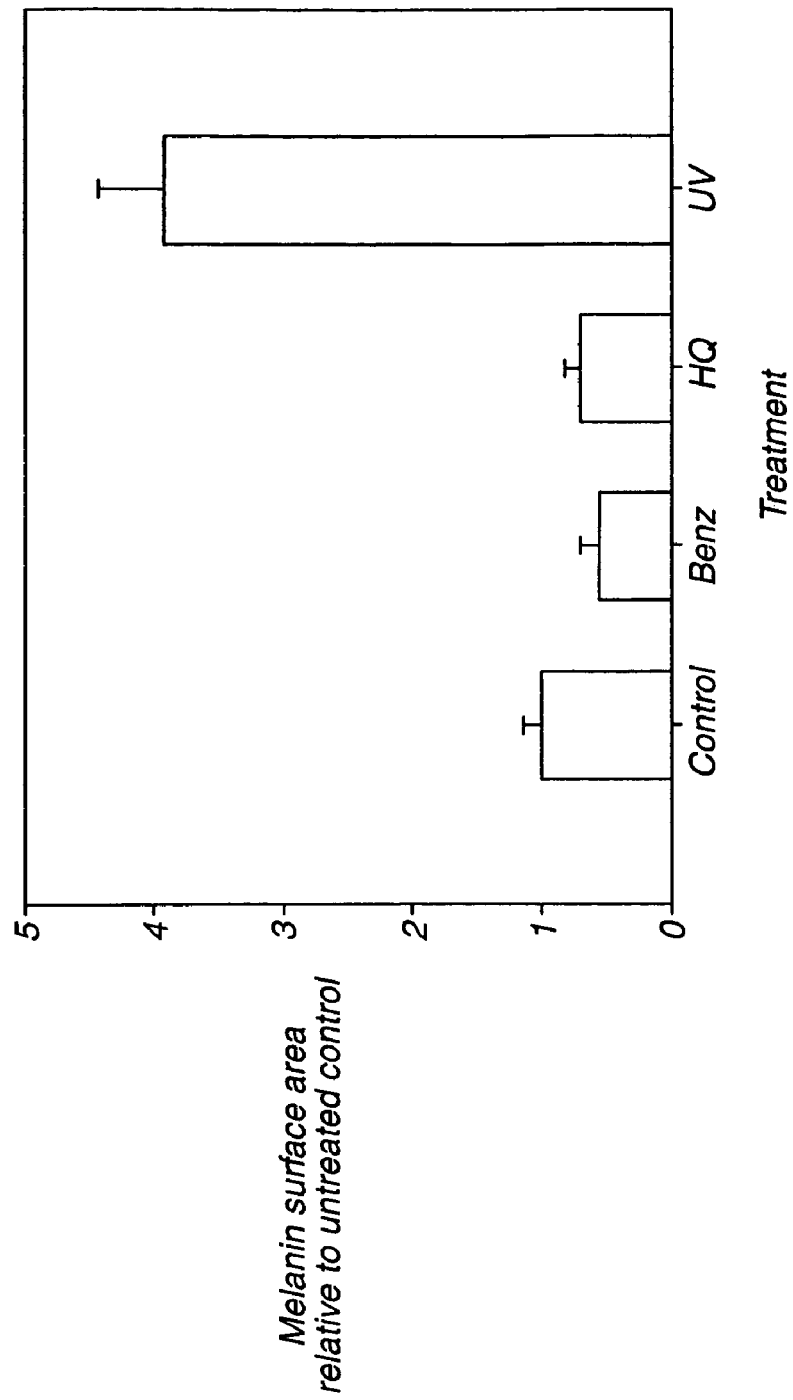

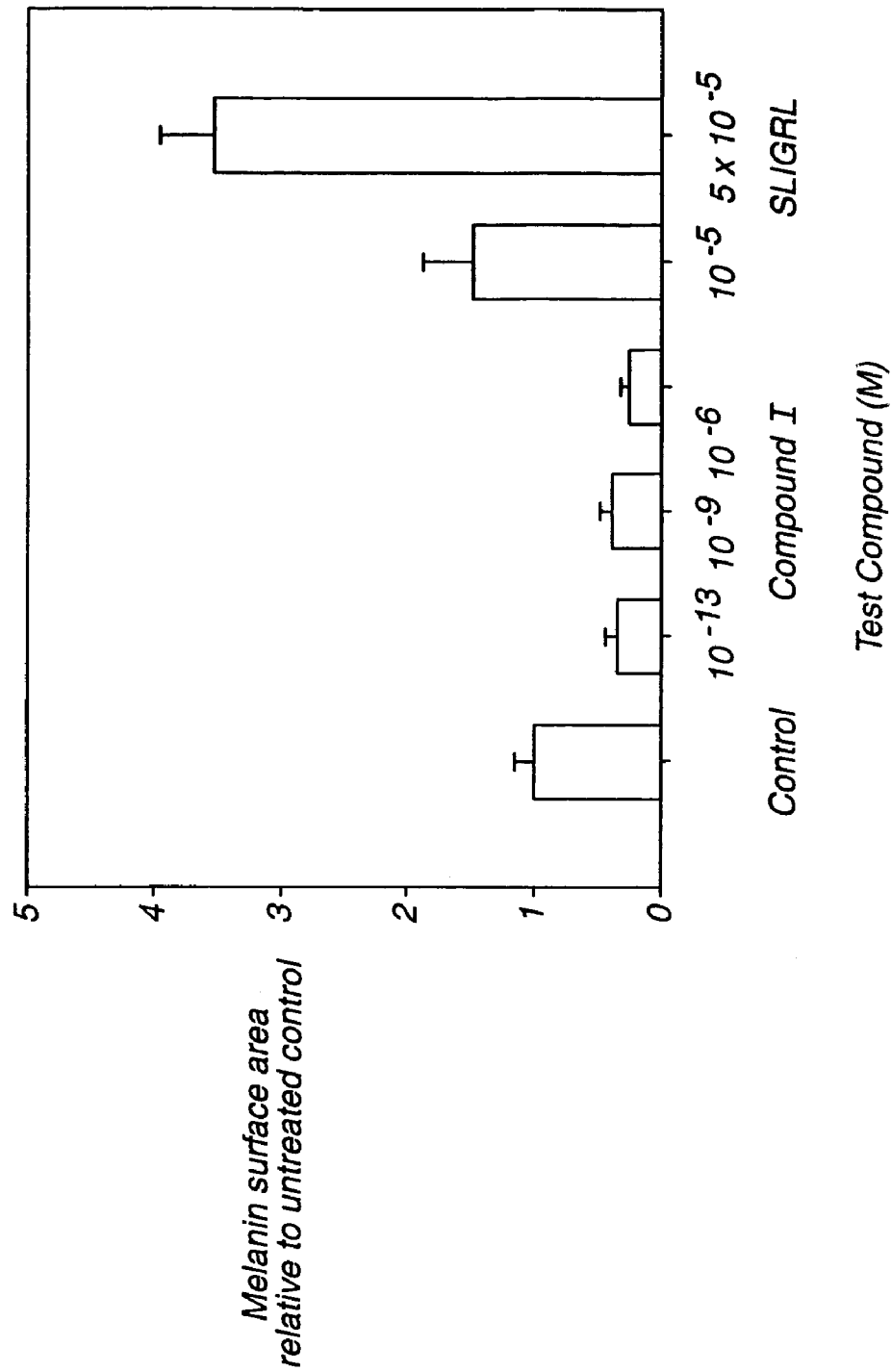

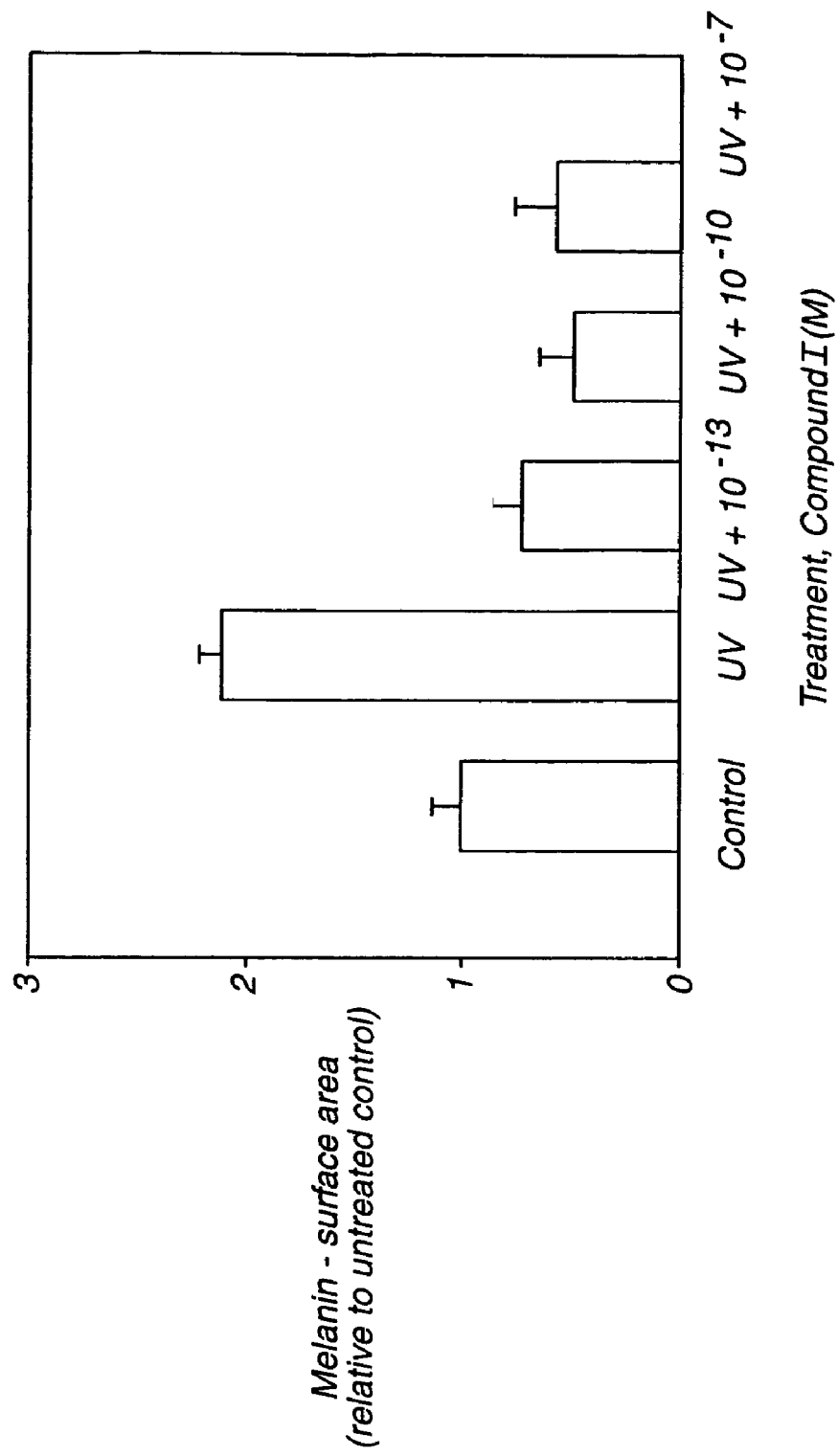

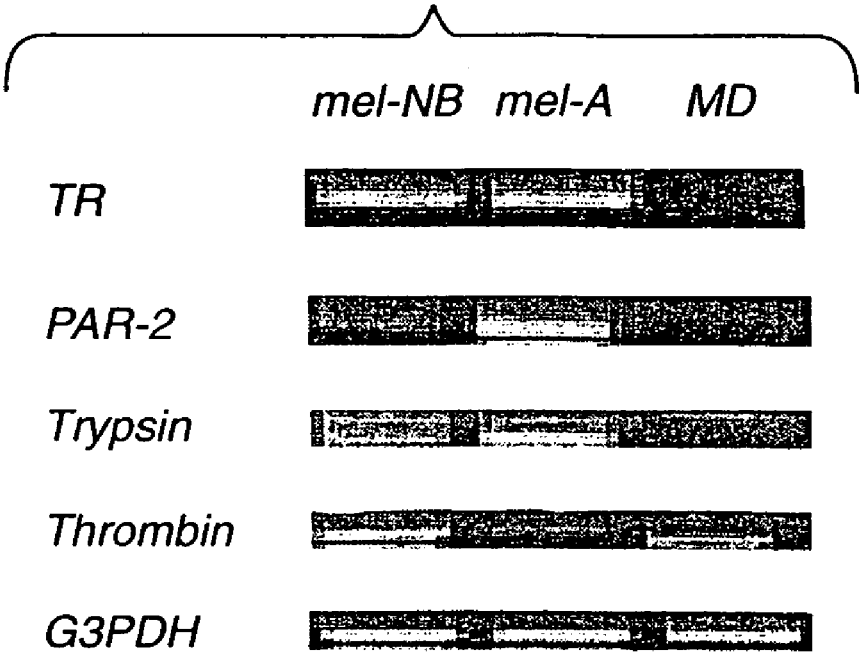

FIG. 6B
| SLIGRL μM | 0 | 2 | 10 | 50 |
|---|---|---|---|---|
| Tyrosinase |  | | | |
| TRP-1 |  | | | |
| TRP-2 |  | | | |
| Trypsin |  | | | |
| G3PDH | 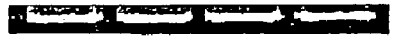 | | | |

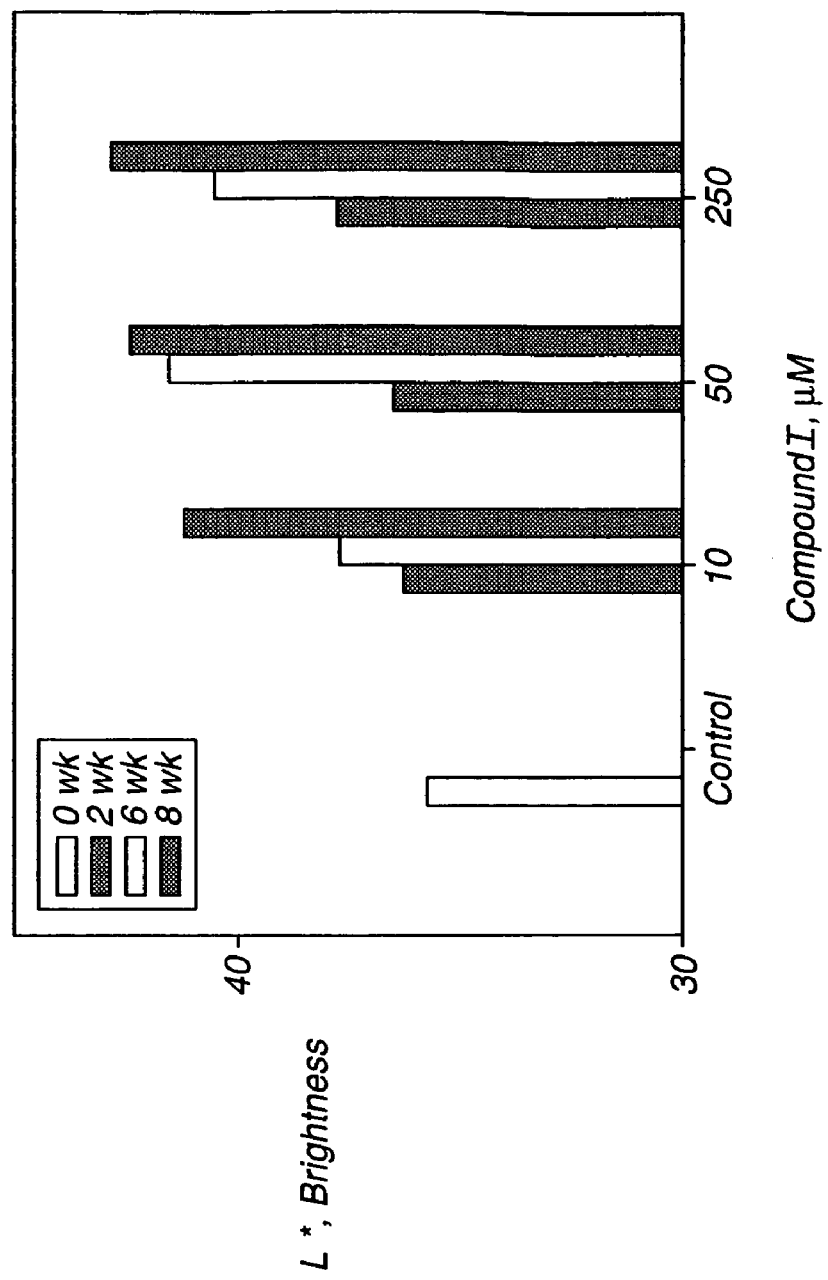

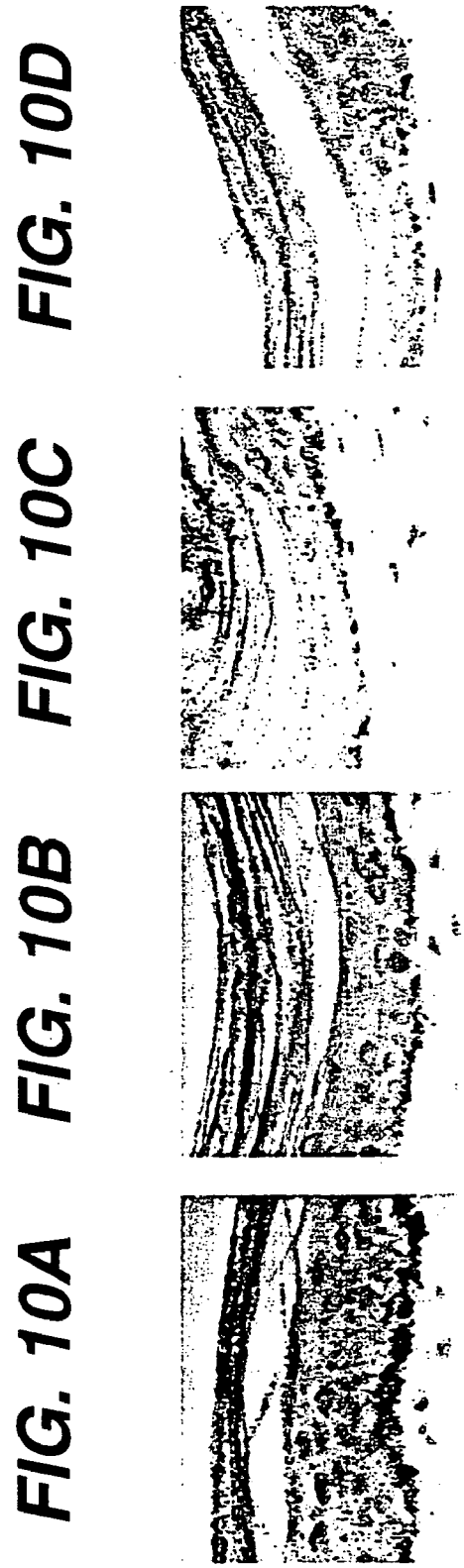

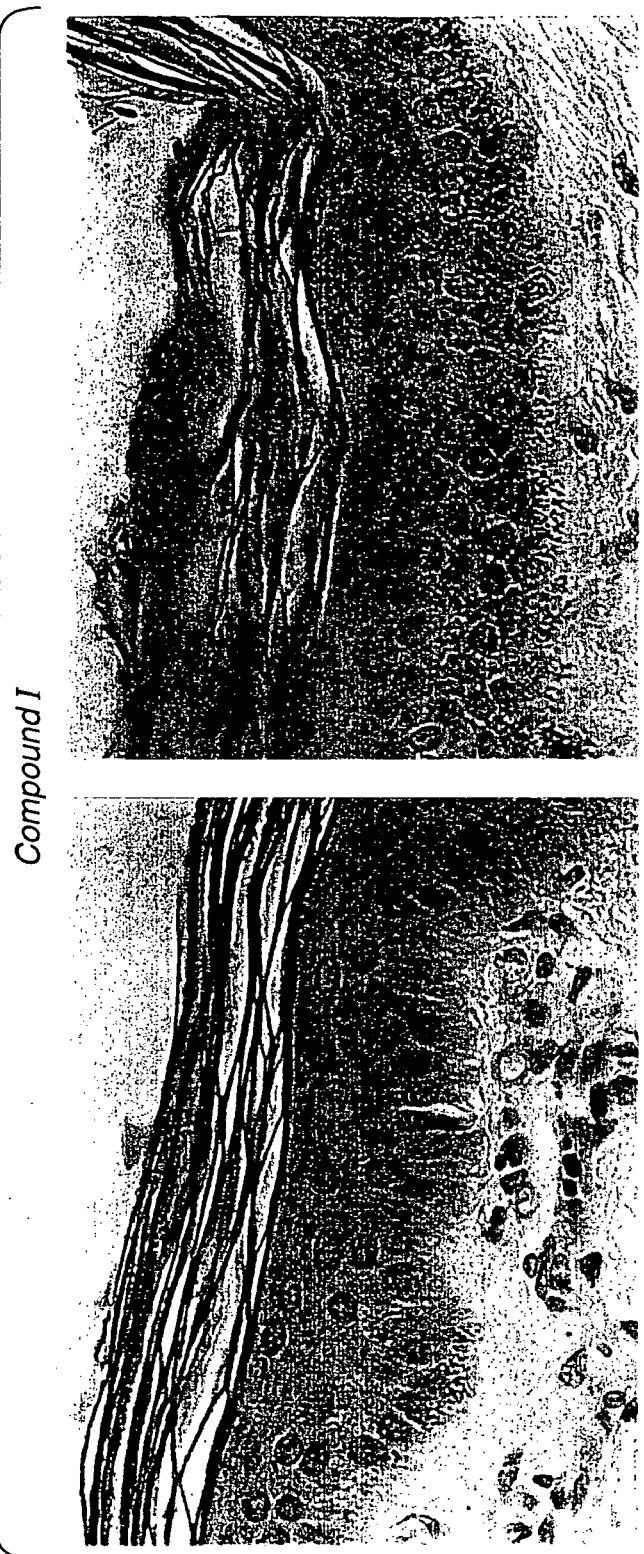
FIG. 12B Compound I

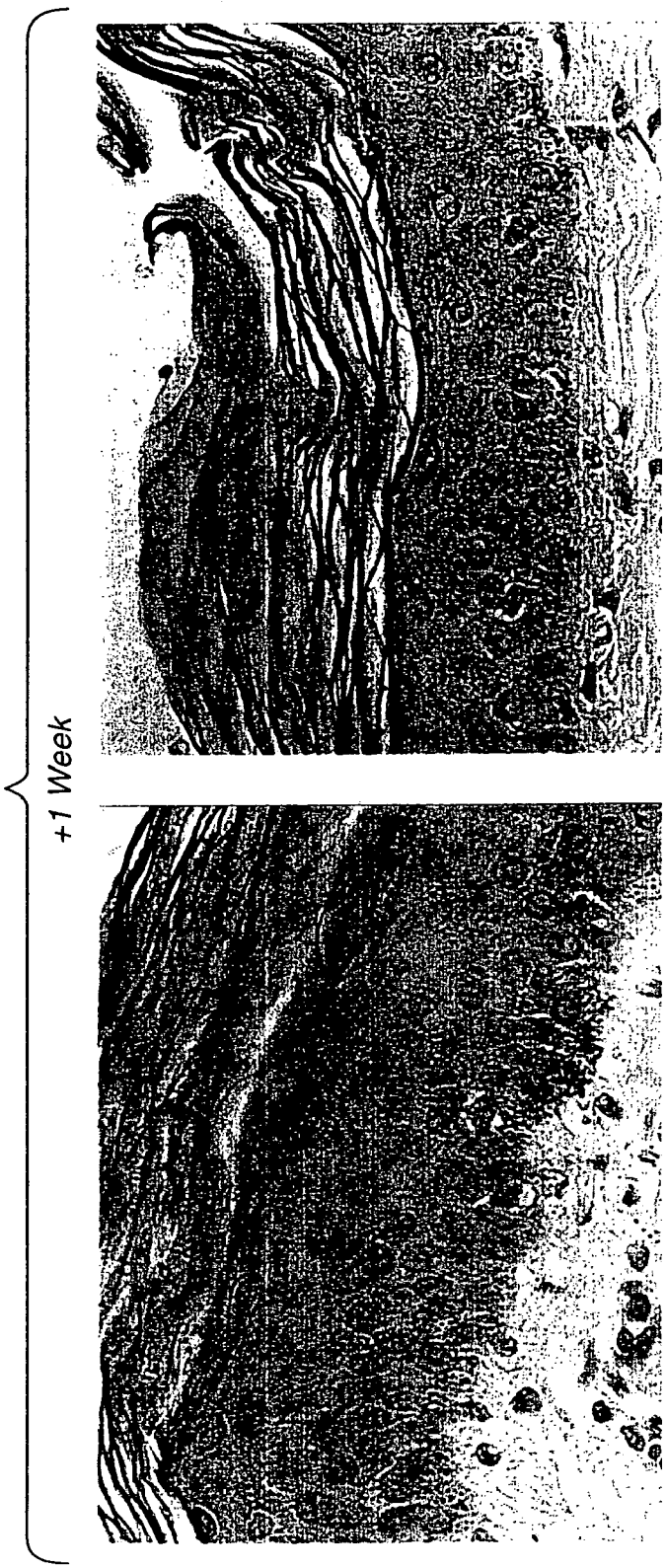
FIG. 12C +1 Week

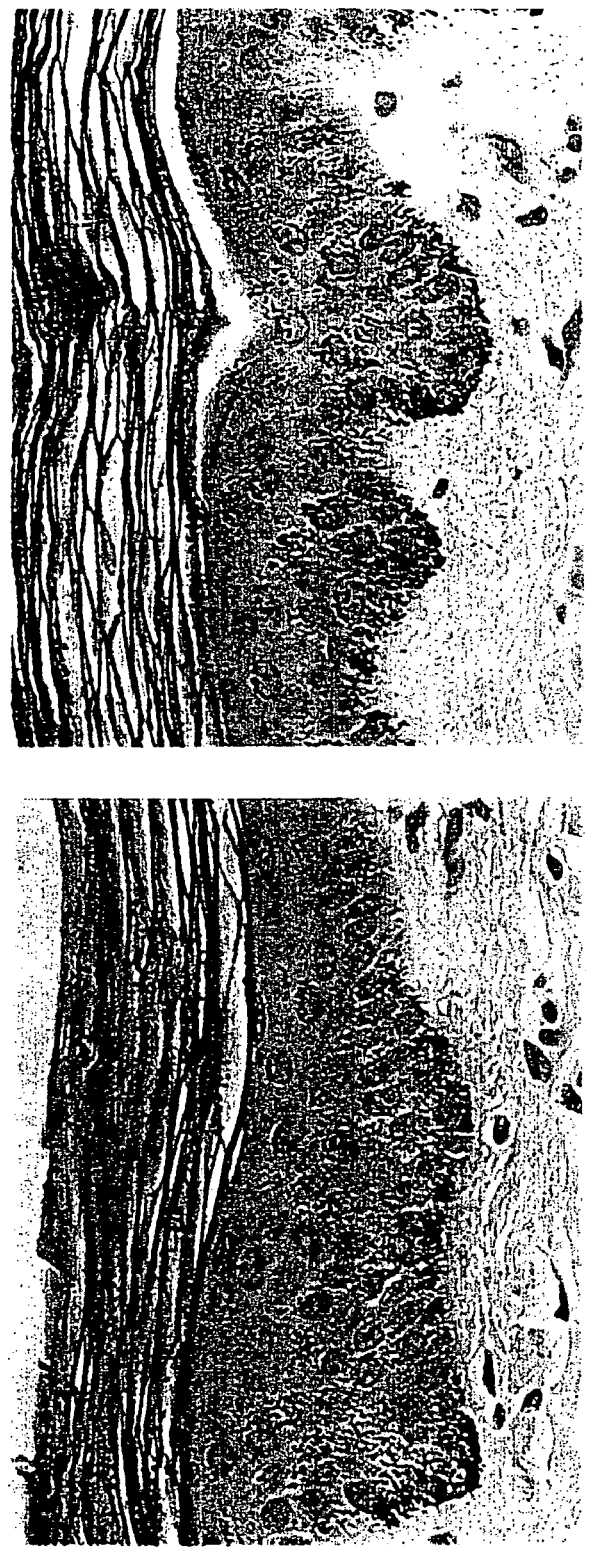
FIG. 12E +4 Weeks

METHODS FOR TREATING SKIN PIGMENTATION

This application claims the benefit of provisional applications 60/053,942 filed on Jul. 28, 1997 and 60/080,441 filed on Apr. 2, 1998.

FIELD OF THE INVENTION

This invention is related to methods and compositions for bringing about skin pigmentation and/or for causing skin depigmentation. More particularly, this invention relates to compounds which affect melanogenesis and can be used as depigmenting agents or as agents for darkening skin.

BACKGROUND OF THE INVENTION

Skin coloring has been of concern to human beings for many years. In particular, the ability to remove hyperpigmentation, such as found in age spots, freckles or aging skin generally, is of interest to individuals desiring a uniform complexion. In certain areas of the world, general body whitening is desirable. There are also hypopigmentation and hyperpigmentation disorders that are desirable to treat. Likewise, the ability to generate a tanned appearance without incurring photodamage due to solar radiation is important to many individuals. There have been many methods proposed to accomplish depigmentation, as well as to accomplish darkening of the skin. For example, kojic acid, hydroquinone, retinoids and other chemical compounds have been used for depigmentation. Dihydroxyacetone and like chemical compounds have been utilized for their ability to "tan" the skin without exposure to the sun.

Many of these previous solutions have not been found acceptable. There is often a distinct line of demarcation between the areas of skin to which such previous compositions have been applied. Therefore, precise application of all these compounds is necessary in order to achieve the desired result. Many of these compounds have been found to be quite irritating to the skin and therefore undesirable for use.

The understanding of the chemical and enzymatic basis of melanogenesis is heavily documented. Melanocytes migrate from the embryonal neural crest into the skin to produce secretory granules, melanosomes, which produce melanin. Melanogenesis occurs within the melanosome, and the melanin is later distributed to keratinocytes via the melanocyte dendrites. The key enzyme in melanogenesis is tyrosinase, which initiates a cascade of reactions which convert tyrosine to the biopolymer melanin. Two tyrosinase-related proteins (TRP's) are known, TRP-1 and TRP-2. These proteins share with tyrosinase about 40% homology and have catalytic activities as well as regulatory roles in melanogenesis. TRP-1 is the most abundant glycoprotein in melanocytes.

In spite of the fact that the chemical and enzymatic basis of melanogenesis is well-documented, its regulation at the cellular level is only partially understood. Tyrosinase and the TRP's share structural and biological properties with the lysosomal-associated membrane protein (LAMP) gene family, therefore their targeting to the melanosomal membrane might induce their activation. A phosphorylation/dephosphorylation reaction at the cytoplasmic tails of thes proteins could be involved in the regulation of melanogenesis. The beta isoform of the Protein Kinase C (PKC) family has been shown to regulate human melonogenesis through tyrosinase activation. Gene expression of tyrosinase, TRP-1 and TRP-2 is coordinated. All three enzymes are expressed in human epidermis. In melanocytes co-cultured with keratinocytes, these transcripts are expressed at a ratio of 45:45:10, respectively. In melanocytes cultured alone, only TRP-1 transcripts are present, indicating that a keratinocyte-derived signal is involved in the coordinate expression of these genes. The regulation of keratinocyte-melanocyte interactions and the mechanism of melanosome transfer into keratinocytes are not yet understood.

The Protease-activated receptor-2 (PAR-2) is a seven transmembrane G-protein-coupled receptor, that is related to, but distinct from the thrombin receptors (TR, also named PAR-1, and PAR-3) in its sequence. Both receptors are activated proteolytically by an arginine-serine cleavage at the extracellular domain. The newly created N-termini then activate these receptors as tethered ligands. Both receptors could be activated by trypsin, but only the TRs are activated by thrombin. Only PAR-2 is activated by mast cell tryptase. Both receptors could also be activated by the peptides that correspond to their new N-termini, independent of receptor cleavage. SLIGRL, the mouse PAR-2 activating peptide, is quipotent in the activation of the human receptor. While the function of the TR is well documented, the biology of the PAR-2 has not yet been fully identified. A role for PAR-2 activation in the inhibition of keratinocyte growth and differentiation has been recently described (Derian et al., "Differential Regulation of Human Keratinocyte Growth and Differentiation by a Novel Family of Protease-activate Receptors", *Cell Growth & Differentiation*, Vol. 8, pp. 743-749, July 1997).

SUMMARY OF THE INVENTION

In accordance with this invention, we have found a method for affecting changes in mammalian skin pigmentation comprising topically applying to the skin of a mammal a compound which affects the PAR-2 pathway. The compositions of this invention may contain one or more compounds that act as trypsin, as tryptase, as serine protease or as PAR-2 agonists, for increase in pigmentation. Alternatively, they may contain one or more compounds that act as serine protease inhibitors, trypsin inhibitors, thrombin inhibitors, tryptase inhibitors, as PAR-2 pathway inhibitors or as a PAR-2 antagonist for decrease in pigmentation, or "depigmentation".

As used herein, "mammal" means any member "of the higher vertebrate animals comprising the class "Mammalia", as defined in Webster's Medical Desk Dictionary 407 (1986), and includes but is not limited to humans. As used herein, "receptor" shall include both intracellullar and extracellular receptors and shall mean those molecules capable of receiving and transducing a signal. The term PAR-2 refers to the protease-activated receptor-2 or a related protease activated receptor.

The Protease-activated receptor-2 (hereinafter, "PAR-2") is a serine-protease activated receptor that is expressed in numerous tissues, including keratinocytes and fibroblasts. The thrombin receptor (also named PAR-1, hereinafter, "TR") is a serine-protease activated receptor that is expressed in numerous tissues, including keratinocytes. The biological roles of PAR-2 and TR in skin are not entirely known. However, we have found that interactions between keratinocytes and melanocytes, via the PAR-2 pathway, affect melanogenesis. We have found that thrombin inhibitors, and/or tryptase inhibitors, and/or trypsin inhibitors and PAR-2 antagonists can be used as depigmenting agents without irritation of the skin. PAR-2 agonists and serine proteases such as trypsin and tryptase can be used as darkening agents. Furthermore, PAR-2 could be useful as a target for whitening and darkening agents.

BRIEF DESCRIPTION OF THE DRAWINGS

FIG. 1A is a graph depicting the increase or decrease in relative pigmentation of epidermal equivalents containing melanocytes treated with known pigmenting and depigmenting agents in accordance with the methods of this invention.

FIG. 4A is a graph depicting the dose/response with respect to pigmentation in epidermal equivalents containing melanocytes when treated with compositions of this invention.

FIG. 4B is a graph depicting the response of epidermal equivalents containing melanocytes after exposure to ultraviolet light followed by treatment with compositions of this invention.

FIG. 5B is a photograph depicting gels showing the expression of TR and PAR-2 by primary human melanocytes.

FIGS. 6A and 6B are photographs depicting gels showing the expression of various genes after treatment with different concentrations of Compound I and SLIGRL.

FIG. 9 is a graph depicting the brightness of Yucatan Swine skin during the course of treatment in accordance with the methods and compositions of this invention.

FIGS. 10A, 10B, 10C and 10D are photographs of F&M stained histological sections of Yucatan Swine skin treated with compositions containing Compound I in accordance with methods of this invention at concentrations of 0, 10 μM, 50 μM and 250 μM respectively.

FIGS. 12A, 12B, 12C, 12D and 12E are photographs of histological F&M stained sections of Yucatan Swine skin, as follows: 12A shows untreated skin; 12B shows skin treated with compositions of this invention after eight weeks of treatment; 12C shows skin one week after stopping treatment; 12D shows skin two weeks after stopping treatment and 12E shows skin four weeks after stopping treatment.

DETAILED DESCRIPTION OF THE PREFERRED EMBODIMENTS

Figure 1B:
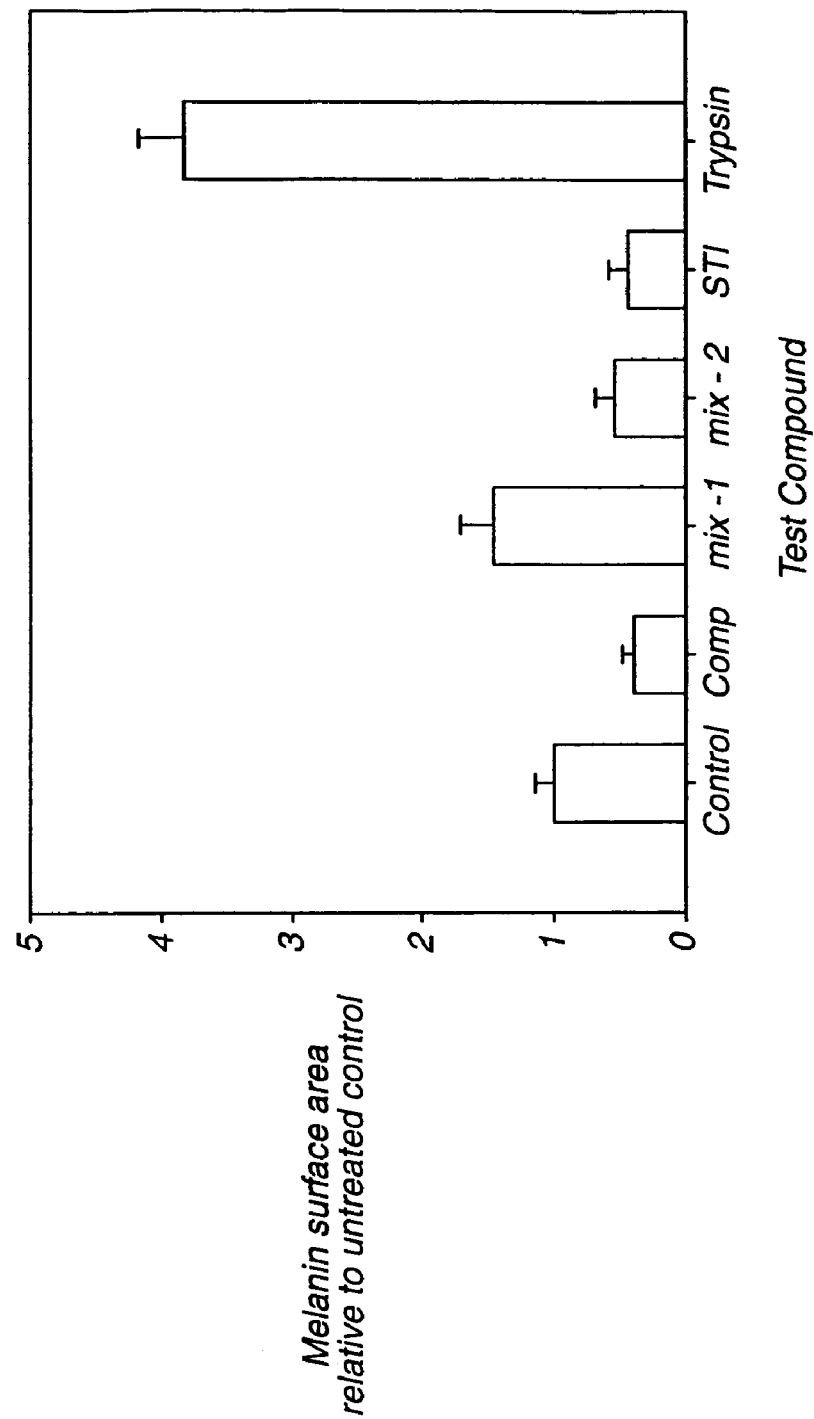
FIG. 1B is a graph depicting the increase or decrease in relative pigmentation in epidermal equivalents containing melanocytes treated in accordance with the methods and compositions of this invention.

We have discovered that trypsin, tryptase and PAR-2 agonists can be used to increase pigmentation and that trypsin inhibitors, and/or tryptase inhibitors, and/or thrombin inhibitors and PAR-2 antagonists act to decrease pigmentation in mammalian skin. Compounds that bind to or block but do not activate PAR-2, such as antagonists based on SLIGRL which bind to or block but do not activate PAR-2, antagonists based on SLIGKVD which bind to or block but do not activate PAR-2 and mixtures thereof may also be used to affect pigmentation. In our opinion, some of the compounds described in U.S. Pat. No. 5,523,308, which is hereby incorporated herein by reference, and behave as thrombin and/or trypsin and/or tryptase inhibitors, will be useful in methods of this invention. Some of these compounds are also described in Costanzo, et al., "Potent Thrombin Inhibitors That Probe the $S_1'$ Subsite: Tripeptide Transition State Analogues Based on a Heterocycle-Activated Carbonyl Group", *J. Med. Chem.*, 1996, Vol. 39, pp. 3039-3043 and have the following structural formula:

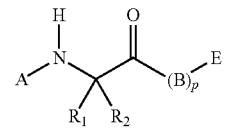

wherein:

A is selected from the group consisting of $C_{1-8}$alkyl, carboxy$C_{1-4}$alkyl, $C_{1-4}$alkoxycarbonyl$C_{1-4}$alkyl, phenyl$C_{1-4}$alkyl, substituted phenyl$C_{1-4}$alkyl (where the phenyl substituents are independently selected from one or more of, $C_{1-4}$ alkyl, perfluoro$C_{1-4}$alkyl, $C_{1-4}$alkoxy, hydroxy, halo, amido, nitro amino, $C_{1-4}$alkylamino, $C_{1-4}$dialkylamino, carboxy or $C_{1-4}$ alkoxycarbonyl), formyl, $C_{1-4}$alkoxycarbonyl, $C_{1-2}$alkylcarbonyl, phenyl$C_{1-4}$alkoxycarbonyl, C3-7cycloakylcarbonyl, Phenylcarbonyl, substituted phenylcarbonyl (where the phenyl substituents are independently selected from one or more of, $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$ alkoxycarbonyl), $C_{1-4}$alkylsulfonyl, $C_{1-4}$alkoxysulfonyl, perfluoro$C_{1-4}$alkyl-sulfonyl, phenylsulfonyl, substituted phenylsulfonyl (where the phenyl substituents are independently selected from one or more of, $C_{1-4}$alkl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl), 10-camphorsulfonyl, phenyl$C_{1-4}$alkysulfonyl, substituted phenyl$C_{1-4}$alkysulfonyl, $C_{1-4}$alkylsulfinyl, perfluoro$C_{1-4}$ alkylsulfinyl, phenylsulfinyl, substituted phenylsulfinyl (where the phenyl substituents are independently selected from one or more of, $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl), phenyl$C_{1-4}$alkylsulfinyl, substituted pehnyl$C_{1-4}$alkylsulfinyl, 1-naphthylsulfonyl, 2-naphthylsulfonyl or substituted naphthylsulfonyl (where the naphthyl substituents are independently selected from one or more of, $C_{1-4}$alkyl, perfluoro$C_{1-4}$ alkyl, $C_{1-4}$alkoxy, hydroxy, halo, amido, nitro, amino, carboxy or $C_{1-4}$alkoxyy-carbonyl), 1-naphthylsulfinyl, 2-naphthylsulfinyl or substituted naphthylsulfinyl (where the naphthyl substituents are independently selected from one or more of, $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl);

a D or L amino acid which is coupled as its carboxy terminus to the nitrogen depicted in formula I and is selected from the group consisting of alanine, asparagine, 2-azetidinecarboxylic acid, glycine, N—$C_{1-8}$alkyglycine, proline, 1-amino-1-cyclo$C_{3-8}$alkylcarboxylic acid, thiazzolidine-4-carboxylic acid, 5,5-dimethylthiazolidine-4-carboxylic acid, oxadolidine-4-carboxylic acid, pipecolinic acid, valine, methionine, cysteine, serine, threonine, norleucine, leucine, tert-leucine, isoleucine, phenylalanine, 1-naphthalanine, 2-naphthalamine, 2-thienylalanine, 3-thienylalanine, [1,2,3,4]-tetrahydroisoquinoline-1-carboxylic acid and 1,2,3,4,]-tetrahydroisoquinoline-2-caroboxylic acid where the amino terminus of said amino acid is connected to a member selected form the group consisting of $C_{1-4}$alkyl, tetrazol-5yl-$C_{1-2}$alkyl, carboxyt$C_{1-4}$alkyl, $C_{1-4}$alkoxycarbonylC14alkyl, phenyl$C_{1-4}$alkyl, substituted phenyl $C_{1-4}$ alkyl (where the phenyl substituents are independently selected from one or more of, $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboy or $C_{1-4}$alkoxycarbonyl), 1,1-diphenyl$C_{1-4}$alkyl, 3-phenyl-2-hydroxypropionyl, 2,2-diphenyl-1-hydroxyethylcarbonyl, [1,2,3,4]-tetrahydroisoquinoline-1-carbonyl, [1,2,3,4]-tetrahydroisoquinoline-3, carbonyl, 1-methylamino-1-cyclohexanecarbonyl, 1-hydroxy-1-cyclohexanecarbonyl, 1-hydroxy-1-pheny-lacetyl, 1-cyclohexyl-1-hydroxyacetyl, 3-phenyl-2-hydroxypropionyl, 3,3-diphenyl-2-hydroxypropionyl, 3-cyclohexyl-2-hydroxypropionyl, formyl, $C_{1-4}$alkoxycarbonyl, $C_{1-12}$alkylcarbonyl, perfluoro$C_{1-4}$alkyl, $C_{1-4}$alkylcarbonyl, phenyl$C_{1-4}$alkylcarbon1, substituted phenyl$C_{1-4}$alkylcarbonyl (where the phenyl substituents are independently selected from one or more of, $C_{1-4}$alkyl, perfluoro$C_{1-4}$alkyl, $C_{1-4}$alkoxy, hydroxy, halo amido, nitro amino, $C_{1-4}$alkylamino, $C_{1-4}$dialkylamino, carboxy or $C_{1-4}$alkoxycarbonyl) 1,1-diphenyl$C_{1-4}$alkylcarbonyl, substituted 1,1-diphenyl$C_{1-4}$alkylcarbonyl (where the phenyl substituents are independently selected from one or more of, $C_{1-4}$alkyl, perfluoro $C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$ alkoxy-carbonyl), perfluoro$C_{1-4}$alkysulfonyl, $C_{1-4}$alkysulfonyl, $C_1$ alkoxysulfonyl, phenysulfonyl, substituted phenylsulfonyl (where the phenyl substituents are independently selected from one or more of, C-1alkyl, perfluoro $C_{1-4}$alkylamino, $C_{1-4}$dialkylamino, carboxy or $C_{1-4}$alkoxycarbonyl), 10-cxamphorsulfonyl, phenyl$C_{1-4}$alkylsulfonyl, substituted phenyl$C_{1-4}$alkylsulfonyl, perfluoro$C_{1-4}$alkysulfinyl, C-14alkysulfinyl, phenylsulfinyl, substituted phenysulfinyl (where the phenyl substituents are independently selected from one or more of, $C_{1-4}$alkyl, perfluoro $C_{1-4}$alkyl, $C_{1-4}$ alkoxy, hydroxy, halo, amido, nitro, amino, $C_{1-4}$ alkylamino, $C_{1-4}$ dialkylamino, carboxy or $C_{1-4}$ alkoxycarbonyl), 1-naphthysulfon1, 2-naphthylsulfonyl, substituted naphthylsulfonyl (where the naphthyl substituents are independently selected from one or more of, $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboy or $C_{1-4}$alkoxycarbonyl), 1-naphthysulfinyl, 2-naphthysulfinyl, and substituted naphthylsulfinyl (where the naphthyl substituents are independently selected from one or more of, $C_{1-4}$alkyl, perfluoro$C_{1-4}$alkyl, $C_{1-4}$alkoxy, hydroxy, halo amido, nitro, amino, $C_{1-4}$alkylamino, C104dialkylamono, carboxy or C-14alkoxycarbonyl):

or a poly peptide comprised of two amino acids, where the first amino acid is a D or L amino acid, bound via its carboxy terminus to the nitrogen depicted in Formula I and is selected from the group consisting of glycine, N—$C_{1-8}$alkylglycine, alanine, 2-azetidinecarboxylic acid, proline, thiazolidine-4-carboxylic acid, 5,5-dimethylthiazolidine-4-carboxylic acid, oxazolidine-4-carboxylic acid, 1-amino-1-cyclo$C_{3-8}$ alkylcarboxylic acid, 3-hydroxypropoline, 4-hydroxyproline, 3-($C_{1-4}$alkoxy)proline, 4($C_{1-4}$alkoxy)proline, 3,4-dehydroprline, 2,2-dimethyl-4-thiazolidine carboxylic acid, 2,2-dimethyl-4-oxadolidine carboxylic acid, pipecolinic acid, valine, methionine, cysteine, asparagine, serine, threonine, leucine, tert-leucine, isoleucine, phenylalanine, 1-naphthalanine, 2-naphthalanine, 2-thienylalanine, 3-thienylalnine, [1,2,3,4]-tetrahydroisoquinoline-2-carboxylic acid, aspartic acid-4-$C_{1-4}$alkyl ester and glutamic acid 5-$C_{1-4}$ alkyl ester and the second D or L amino acid, is bound to the amino terminus of said first amino acid, and is selected from the group consisting of phenylalanine, 4-benzolyphenylalanine, 4-carboxyphenylalanine, 4-(Carboxy C1-2alkyl)phenylalanine, substituted phenylalanine (where the phenyl substituents are independently selected from one or more of $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl), 3-benzothienylalanine, 4-biphenylalanine, homophenylalanine, octahydroindole-2-carboxylic acid, 2-pyridylalanine, 3-pyridylalanine, 4-thiazolyalanine, 2-thienylalanie, 3-(3-benzothienyl)alanine, 3-thienylalanine, tryptophan, tyrosine, asparagine, 3-tri-$C_{1-4}$alkylsilylalanine, cyclohexylglycine, diphenylglycine, phenylglycine, methionine sulfoxide, methionine sulfone, 2,2-dicyclohexylalanine, 2-(1-naphthylalanine), 2-(2-naphthylalanine), phenyl substituted phenylalanine (where the substituents are selected from $C_{1-4}$alkyl, perfluoro$C_{1-4}$ alkyl, $C_{1-4}$ alkoxy, hydroxy, halo, amido, nitro, amino, $C_{1-4}$alkylamino,$C_{1-4}$dialylamino, carboxy or$C_{1-4}$ alkoxycarbonyl), aspartic acid, aspartic acid-4$C_{1-4}$alkyl, perfluoro$c_{1-4}$ alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbony), aspartic acid, aspartic acid-4-$C_{1-4}$alkyl ester glutamic acid, glutamic acid-5-$C_{1-4}$ alkyl ester, cycloC3-salkylaalanine, substituted cyclo$C_{3-8}$alkylalanine (where th ring substituents are carboxy, $C_{1-4}$ alkyl ester, cycloC3-salkylalanine, substituted cyclo$C_{3-8}$alkylalanine (where the ring substituents are carboxy, $C_{1-4}$alkylcarboxy, $C_{1-4}$alkoxycarbonyl or aminocarbonyl), 2,2-diphenylalanine and all alpha-$C_{1-5}$alkyl of all amino acid derivatives thereof, where the amino terminus of said second amino acid is unsubstituted or monosubstituted with a member of the group consisting of formyl, C1-12 alkyl, tetrazol-5-ylC1-2alkyl, carboxyC1-8 alkyl, carboalkoxy$C_{1-4}$alkyl, phenyl $C_{1-4}$alkyl, substituted phenyl$C_{1-4}$alkyl (where the phenyl substituents or independently selected from one or more of, $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl), 1,1-dipehnyl$C_{1-4}$alkyl, C1-6alkoxycarbonyl, phenylC1-6alkoxycarbonyl, C1-2alkylcarbonyl, perfluoro$C_{1-4}$alkylCo-4alkylcarbonyl, pheny$C_{1-4}$alkylcarbonyl, substituted pheny$C_{1-4}$alkylcarbonyl (where the phenyl substituents are independently selected from one or more of $C_{1-4}$alkyl, perfluoro $C_{1-4}$alkyl, $C_{1-4}$ alkoxy, hydroxy, halo, amido, nitro, amino, $C_{1-4}$alkylamino, $C_{1-4}$dialkylamino, carboxy or $C_{1-4}$alkoxycarbonyl), 1,1-diphenyl$C_{1-4}$alkyl, perfluoro$C_{1-4}$alkyl, $C_{1-4}$alkoxycarbonyl), 10-camphorsulfonyl, phenyl$C_{1-4}$alkysulfonyl, substituted phenyl$C_{1-4}$alkylsulfonyl, $C_{1-4}$alkysulfinyl, perfluoro $C_{1-4}$alkylsulfinyl, phenylsulfinyl, substituted phenylsulfinyl (where the phenyl substituents are independently selected from one or more of, $C_{1-4}$alkyl, perfluoro$C_{1-4}$alkyl, $C_{1-4}$alkoxy, hydroxy, halo, amido, nitro, amino, $C_{1-4}$alkylamono, $C_{1-4}$dialkylamono, carboxy or $C_{1-4}$alkoxycarbonyl), phenyC$_{1-4}$alkylsulfinyl, substituted phenylC$_{1-4}$alkylsulfinyl 1-naphthylsulfonyl, 2-naphthylsulfonyl, substituted naphthylsulfonyl (where the naphthyl substituent is selected from $C_{1-4}$alkyl, perfluoroC$_{1-4}$ alkyl, $C_{1-4}$alkoxy, hydroxy, halo amido, nitro, amino, $C_{1-4}$alkylamino, $C_{1-4}$dialkylamino, carboxy or $C_{1-4}$alkoxycarbonyl), 1-haphthyl-sulfinyl, 2-haphthylsulfinyl and substituted naphthyl-sulfinyl (where the naphthyl substituent is selected from $C_{1-4}$alkyl, perfluoroC$_{1-4}$alkyl, $C_{1-4}$alkoxy, hydroxy, halo, amido, nitro, amino, $C_{1-4}$alkylamino, C-14dialkylamino, carboxy or $C_{1-4}$alkoxycarbonyl); $R_1$ is selected from the group consisting of hydrogen and alkyl;

$R_2$ is selected from the group consisting of aminoC2-salkyl, guanidinoC$_{2-5}$alkyl, $C_{1-4}$alkylguanidinoC$_{2-5}$alkyl, diC$_{1-4}$ alkylguanidinoC$_{2-5}$alkyl, amidinoC$_{2-5}$alkyl, $C_{1-4}$alkylguanidinoC$_{2-5}$alkyl, diC$_{1-4}$alky-lguanidinoC$_{2-5}$alkyl, $C_{1-3}$alkoxyC$_{2-5}$alkyl, phenyl, substituted phenyl (where the substituents are independently selected from one or more of amino, amidino, guanidino, $C_{1-4}$alkylamino, $C_{1-4}$dialkylamino, halogen, perfluoro $C_{1-4}$alkyl, $C_{1-4}$alkyl, $C_{1-3}$ alkoxy or nitro), benzyl, phenyl substituted benzyl (where the substituents are independently selected from one or more of, amino, amidino, guanidino, $C_{1-4}$alkylamino, $C_{1-4}$dialkylamino, halogen, perfluoro $C_{1-4}$alkyl, C1-04alkyl, $C_{1-3}$alkoxy or nitro), hydroxyC$_{2-5}$alkl, C'$_{1-5}$alkylaminoC$_{2-5}$alkyl, $C_{1-5}$dialkylaminoC$_{2-5}$alkyl, 4-aminocyclohexylC$_{0-2}$alkyl and $C_{1-5}$alkyl;

p is 0 or 1;
B is

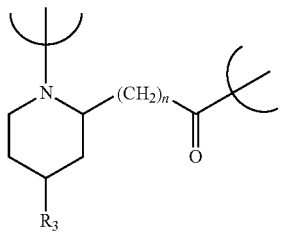

where n is 0-3, $R_3$ is H or C1-5alkyl and the carbonyl moiety of B is bound to E;

E is a heterocycle selected from the group consisting of oxazolin-2-yl, oxazol-2-yl, thiazol-2-yl, thiazol-5-yl, thiazol-4-yl, thiazolin-2-yl, imidazol-2-yl, 4-oxo-2-quinoxalin-2yl, 2-pyridyl, 3-pyridyl, benzo[b}thiophen-2-yl, triazol-4-yl triazol-6-yl, pyrazol-2-yl, 4,5,6,7-tetrahydrobenzothiazol-2yl, naphtho[2,1-d]thiazol-2-yl, naphtho[1-2-d]thiazol-2-ylquinoxalin-2-yl, isoquinolin-1-yl, isoquinolin-3-yl, benzo[b]furan-2-yl, [pyrazin-2-yl, isothiazol-5-yl, isothiazol-3-yl, purin-8yul and a substituted heterocycle where the substituents are selected from $C_{1-4}$ from C-14alky, perfluoro $C_{1-4}$alkyl, $C_{1-4}$alkoxy, hydroxy, halo, amido, nitro, amino, $C_{1-4}$alkylamino, $C_{1-4}$dialkylamino, carboxy, $C_{1-4}$alkoxycarbonyl, hydroxy or phenylC$_{1-4}$ alkylaminocarbonyl;

or pharmaceutically acceptable salts thereof.

More particularly, in our opinion, some of the compounds of the foregoing formula containing a d-phenylalanine-proline-arginine motif should be effective in inhibiting the PAR-2 pathway and causing depigmentation. One particularly preferred compound which acts as a thrombin and trypsin inhibitor and is active in depigmenting mammalian skin is (S)—N-Methyl-D-phenylalanyl-N-[4-[(aminoiminomethyl)amino]-1-(2-benzothiazolylcarbonyl)butyl]-L-prolinamide (Chemical Abstracts name) (hereinafter referred to as "Compound I"). We suggest that other compounds which are analogs or function similarly to Compound I and are set forth in U.S. Pat. No. 5,523,308 may be active in the methods and compositions of this invention. Other compounds that inhibit trypsin, such as serine protease inhibitors, and in particular, soybean trypsin inhibitor (STI) will also be useful in methods of this invention. Soybean, limabean and blackbean extracts, and other natural products made from these beans, such as, but not limited to, bean milk, bean paste, miso and the like, also serve to reduce pigmentation by this mechanism.

Additional sources of serine protease inhibitors may be extracted from th species belonging to the following plant families: Solanaceae (e.g., potato, tomato, tomatilla, and the like); Gramineae (e.g., rice, buckwheat, sorghum, wheat, barley, oats and the like); Cucurbitaceae (e.g., cucumbers, squash, gourd, luffa and the like); and, preferably, Leguminosae (e.g., beans, peas, lentils, peanuts, and th like).

While not willing to be bound by the following theory, we theorize that the compounds capable of affecting the pigmentation of the skin do so by interacting directly or indirectly with the keratinocyte PAR-2 or with its activating protease, and thereby affect melanogenesis, directly or indirectly. Possibly, the compounds of this invention induce, in the case of increased pigmentation or reduce, in the case of decreased pigmentation, the signal to transport melanosomes by melanocytes, or to receive melanosomes by keratinocytes in the skin.

The compounds which are active in the compositions and methods of this invention may be delivered topically by any means known to those of skill in the art. If the delivery parameters of the topically active pharmaceutical or cosmetic agent so require, the topically active composition of this invention may preferably be further composed of a pharmaceutically or cosmetically acceptable vehicle capable of functioning as a delivery system to enable the penetration of the topically active agent into the skin.

One acceptable vehicle for topical delivery of some of the compositions of this invention, particularly proteins such as trypsin and STI, may contain liposomes. The liposomes are more preferably non-ionic and contain a) glycerol dilaurate (preferably in an amount of between about 5% and about 70% by weight); b) compounds having the steroid backbone found in cholesterol (preferably in an amount of between about 5% and about 45% by weight); and c) one or more fatty acid ethers having from about 12 to about 18 carbon atoms (preferably in an amount of between about 5% and about 70% by weight collectively), wherein the constituent compounds of the liposomes are preferably in a ratio of about 37.5:12.5:33.3:16.7. Liposomes comprised of glycerol dilaurate/cholesterol/polyoxyethylene-10-stearyl ether/polyoxyethylene-9-lauryl ether (GDL liposomes) are most preferred. Preferably the liposomes are present in an amount, based upon the total volume of the composition, of from about 10 mg/mL to about 100 mg/mL, and more preferably from about 20 mg/mL to about 50 mg/mL. A ratio of about 37.5:12.5:33.3:16.7 is most preferred. Suitable liposomes may preferably be prepared in accordance with the protocol set forth in Example 1, though other methods commonly used in the art are also acceptable. The above described composition may be prepared by combining the desired components in a suitable container and mixing them under ambient conditions in any conventional high shear mixing means well known in the art for non-ionic liposomes preparations, such as those disclosed in Niemiec et al., "Influence of Nonionic Liposomal Composition On Topical Delivery of Peptide Drugs Into Pilosebacious Units: An In Vivo Study Using the Hamster Ear Model,"

12 Pharm. Res. 1184-88 (1995) ("Niemiec"), which is incorporated by reference herein in its entirety. We have found that the presence of these liposomes in the compositions of this invention may enhance the depigmenting capabilities of som of the compositions of this invention.

Other preferable formulations may contain, for example, soybean milk or other liquid formulations derived directly from legumes or other suitable plant. For example, such a formulation may contain a large proportion of soybean milk, an emulsifier that maintains the physical stability of the soybean milk, and, optionally a chelating agent, preservatives, emollients, humectants and/or thickeners or gelling agents.

Oil-in-water emulsions, water-in-oil emulsions, solvent-based formulations and aqueous gels known to those of skill in the art may also be utilized as vehicles for the delivery of the compositions of this invention.

The source of active compound to be formulated will generally depend upon the particular form of the compound. Small organic molecules and peptidyl fragments can be chemically synthesized and provided in a pure form suitable for pharmaceutical/cosmetic usage. Products of natural extracts can be purified according to techniques known in the art. Recombinant sources of compounds are also available to those of ordinary skill in the art.

In alternative embodiments, the topically active pharmaceutical or cosmetic composition may be optionally combined with other ingredients such as moisturizers, cosmetic adjuvants, anti-oxidants, bleaching agents, tyrosinase inhibitors and other known depigmentation agents, surfactants, foaming agents, conditioners, humectants, fragrances, viscosifiers, buffering agents, preservatives, sunscreens and the like. The compositions of this invention may also contain active amounts of retinoids (i.e., compounds that bind to any members of the family of retinoid receptors), including, for example, tretinoin, retinol, esters of tretinoin and/or retinol and the like.

The topically active pharmaceutical or cosmetic composition should be applied in an amount effective to affect changes in the pigmentation of mammalian skin. As used herein "amount effective" shall mean an amount sufficient to cover the region of skin surface where a change in pigmentation is desired. Preferably, the composition is liberally applied to the skin surface such that, based upon a square cm of skin surface, from about 2 $\mu l/cm^2$ to about 200 $\mu l/cm^2$ of topically active agent is present when a change in pigmentation is desired. When using a thrombin and trypsin inhibitor such as Compound I or its analogs, whether synthetically- or naturally-derived in a formulation, such an active compound should be present in the amount of from about 0.0001% to about 15% by weight/volume of the composition. More preferably, it should be present in an amount from about 0.0005% to about 5% of the composition; most preferably, it should be present in an amount of from about 0.001 to about 1% of the composition. Of course, these ranges are suggested for the foregoing components. The lower set of ranges is intended to be efficacious for PAR-2 pathway agonists/antagonists and/or inhibitors having high therapeutic indices and which do not require significantly larger concentrations or doses to be effective in the methods of this invention. Such compounds may be synthetically- or naturally-derived.

Liquid derivatives and natural extracts made directly from plants or botanical sources may be employed in the compositions of this invention in a concentration (w/v) from about 1 to about 99%. Fractions of natural extracts and naturally-derived protease inhibitors such as STI may have a different preferred range, from about 0.01% to about 20% and, more preferably, from about 1% to about 10% of the composition.

Of course, mixtures of the active agents of this invention may be combined and used together in the same formulation, or in serial applications of different formulations.

We have unexpectedly found that when topically active agents, such as PAR-2 agonists and/or inhibitors and trypsin and/or thrombin and/or tryptase and/or their inhibitors, are topically applied to an animal's skin, a significant change in pigmentation was achieved. Preferably, depigmenting agents (as w II as other pigmentation-affecting agents of this invention) are applied to the skin of a mammal at a relatively high concentration and dose (from about 0.005% to about 1% for compounds having high therapeutic indices such as Compound I and related compounds; from about 20% to about 99% for liquid derivatives and extracts of botanical materials; and from about 1% to about 20% for fractions of natural extracts and naturally-derived protease inhibitors such as STI or mixtures thereof) between one and two times daily for a period of time until the skin evidences a change in pigmentation. This may be for from about four to about ten weeks or more. Thereafter, once the change in pigmentation has been achieved, a lower concentration and dose (from about 0.00001% to about 0.005% for compounds having high therapeutic indices such as Compound I and related compounds; from about 10% to about 90% for liquid derivatives and extracts of botanical materials; and from about 0.01% to about 5% for fractions of natural extracts and naturally-derived protease inhibitors such as STI or mixtures thereof), of active ingredient may be applied on a less frequent time schedule, e.g., about once per day to about twice per week. The effects of the active agents of this invention are reversible, therefore, in order to maintain these effects, continuous application or administration should be performed. The invention illustratively disclosed herein suitably may be practiced in the absence of any component, ingredient, or step which is not specifically disclosed herein.

Several examples are set forth below to further illustrate the nature of the invention and the manner of carrying it out, but do not serve to limit the scope of the methods and compositions of this invention.

Example 1

Protease Inhibitors Affect Pigmentation

In order to study the possible roles of the PAR-2 pathway in pigmentation, an in vitro epidermal equivalent system was used. The epidermal equivalent system used contained melanocytes. One epidermal equivalent system which is useful in performing this study is the MelanoDerm system, available commercially from MatTek Co. This system contains human normal melanocytes, together with normal, human-derived epidermal keratinocytes, which have been cultured to form a multi-layered, highly differentiated model of the human epidermis. In the following examples, equivalents were treated with test compounds for three days and samples were harvested on the fourth day after beginning of treatment. The harvested equivalents were stained with DOPA (a substrate for tyrosinase) and H&E (a standard histological stain) or with Fontana-Mason (F&M) staining, another stain known to those of skill in the art. F&M staining is a silver staining technique that clearly and cleanly marks melanins which have high silver nitrate reducing activity. Multilayered human epidermal equivalents containing melanocytes were used as an in vitro model system to study the effect of protease inhibitors on melanogenesis. Epidermal equivalents used were commercially available as MelanoDerm from MatTek of Ashland, Mass. These equivalents are known to respond to ultraviolet B ("UVB") irradiation and known whitening agents such as benzaldehyde and hydroquinone by increasing and reducing pigmentation, respectively. The MelanoDerm epidermal equivalents were exposed to benzaldehyde (available from Sigma of St. Louis, Mo.), hydroquinone (available from Sigma) and UVB irradiation. UV irradiation was performed with a UVB FS light source in an exposure chamber, with plate covers removed and Phosphate-buffered saline (PBS, from Gibco-BRL, Gaithersburg, Md.) present in the lower chamber. UVB intensity was measured with a UVX radiometer (UVP Inc., San Gabriel, Calif.). Equivalents were treated with 0.1-0.12 J/cm$^2$. No loss of viability was observed in equivalents treated with up to 0.3 J/cm$^2$.

On the fourth day of exposure to the test compounds/ultraviolet irradiation, the equivalents were fixed, sectioned and stained, or stained as whole without sectioning. MelanoDerm equivalents were formalin fixed and put in paraffin blocks, and sections from the MelanoDerm equivalents were stained in accordance with the following standard procedures: (1) H&E, (2) DOPA+H&E and (3) Fontana-Mason ("F&M") using standard techniques known to those of skill in the art. Alternatively, whole MelanoDerm equivalents were stained and their images were captured for image analysis. At least three sections per equivalent, thre equivalents per experiment were processed. Each experiment was repeated three time. DOPA is a substrate for tyrosinase. F&M identifies silver nitrate reducing molecules, which identifies primarily melanins. F&M stained sections were used for image analysis using Optomax Image Analysis Systems, from Optomax Inc., Hollis, N.H. Alternatively, Empire Images database 1.1 was used on a Gateway 2000 P5-100 computer (Media Cybernetics, Silver Springs, Md.) for capturing images. Image Pro Plus version 4.0 was used for image analysis. Parameters measured were as follows: (1) level of pigmentation within individual melanocytes and (2) number of pigmented melanocytes per field, for the Optomax system, or (1) the surface area of silver deposits within melanocytes and (2) the number of pigmented melanocytes for the Image Pro system. Using the Optomax system, surface area of silver deposits within individual melanocytes was measured in 60 melanocytes, using multiple sections from triplicate equivalents per treatment. The number of melanocytes per field was calculated in these sections. A "pigmentation factor" was defined as the average surface area of silver deposits within an individual melanocyte, multiplied by the number of pigmented melanocytes per field. A value of one was assigned to untreated controls, and values of treatment groups were normalized to their relevant controls. Using the Image Pro system, surface area of silver nitrate deposits and number of melanocytes were measured for whole equivalents. A value of one was assigned to untreated controls and values of treatment groups were normalized to their relevant controls.

FIG. 1A is a graph depicting the increase or decrease in relative pigmentation, as measured and calculated by the whole equivalent/Image Pro system, as set forth above, when exposed to benzaldehyde (50 μM), hydroquinone (50 μM) and UVB irradiation (0.12 J/cm$^2$).

The human epidermal equivalents were also exposed to mixtures of protease inhibitors, said protease inhibitors are set forth in Table A below. The protease inhibitors were available from Boehringer Mannheim of Indianapolis, Ind. Complete® Protease Inhibitor Cocktail tablets available from Boehringer Mannheim were used, containing inhibitors of chymotrypsin, thermolysin, papain, pronase, pancreatic extract and trypsin. Soybean trypsin inhibitor ("STI") was available from Sigma and was dissolved in a 50 mg/ml liposome vehicle or in 1×PBS. All other protease inhibitors used in this in vitro example were dissolved in 1×PBS. GDL liposomes were prepared as set forth in Niemic, et al., above, with the exception of the following changes: the non-ionic liposomal formulation contained glycerol dilaurate (Emulsynt GDL, ISP Van Dyk)/cholesterol (Croda)/polyoxyethylene-10-stearyl ether (Brij76, ICI)/polyoxyethylene-9-lauryl ether, as at ratio of 37.5:12.5:33.3:16.7. Hepes buffer, 0.05M, pH 7.4 (Gibco-BRL of Gaithersburg, Md.) was used as the aqueous phase in the preparation of the liposomes. These mixtures of protease inhibitors and different combinations of serine protease inhibitors wer tested for their ability to affect melanogenesis. As set forth in FIG. 1B, some of the serine protease inhibitors, particularly STI (soybean trypsin inhibitor), were very effective in inhibiting melanogenesis.

TABLE A

| Test Formulation | Ingredients |
| --- | --- |
| Complete ® | Total protease inhibitor mixture-x25 |
| Mix-1 | Serine Protease inhibitors-90 μg/mL Phenylmethyl-sulfonyl fluoride ("PMSF") and 50 μg/mL L-1-Chloro-3-[4-tosylamido]-4-phenyl-butanone ("TPCK") |
| Mix-2 | Serine protease inhibitors-0.1 μg/mL aprotinin, 50 μg/mL Soybean trypsin inhibitor ("STI"), 0.5 μg/mL leupeptin and 0.25 μg/mL (L-1-Chloro-3-[4-tosylamido]-7-amino-2-heptanone-HCl) ("TLCK") |
| STI | Soybean trypsin inhibitor-1 mg/ml |

Example 2

A Protease-Activated Receptor is Involved in Pigmentation

Figure 2:
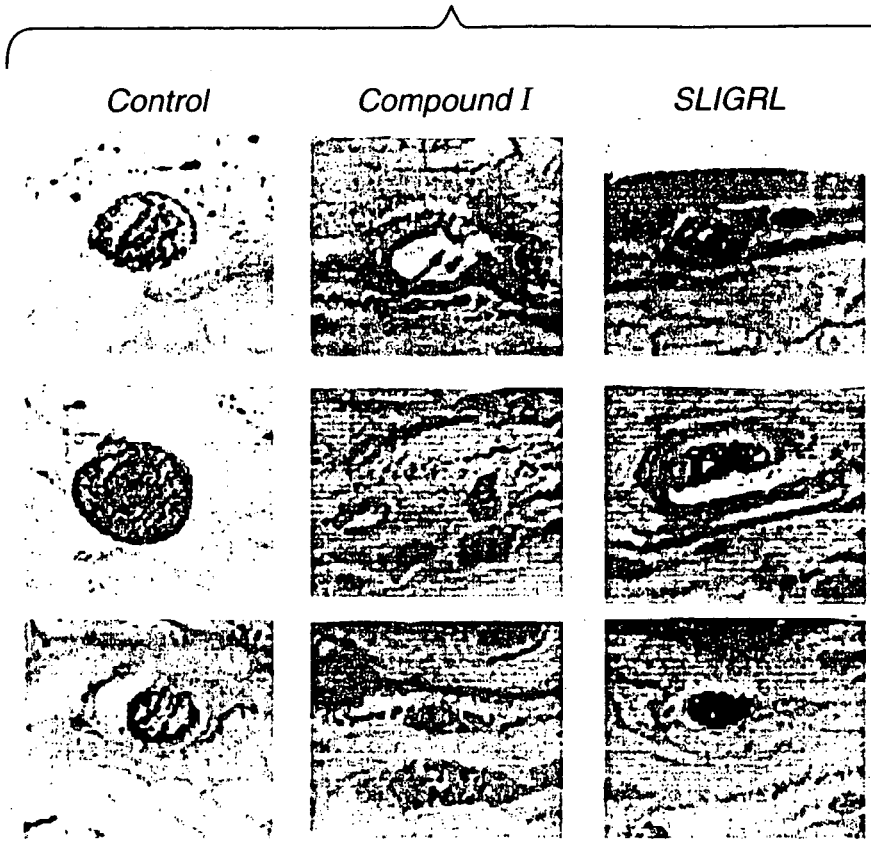
FIG. 2 is a group of images of epidermal equivalents containing melanocytes treated with PAR-2 agonists and Compound I.

Example 1 demonstrates that STI reduces pigmentation. STI inhibits trypsin. Because trypsin is known to activate TR and PAR-2, we tested the possible involvement of TR and PAR-2 in pigmentation. MelanoDerm human epidermal equivalents were treated with the TR and PAR-2 agonists and antagonists set forth in Table B below daily for three days. On the fourth day, the samples were harvested, fixed, and DOPA, H&E or F&M staining was performed. Histological and whole-equivalent examination revealed changes in pigmentation following the treatments. FIG. 2 depicts the results of this example. As shown therein, the PAR-2 peptide agonist SLIGRL induced pigmentation in individual melanocytes. Treatment with Compound I, an inhibitor of thrombin and trypsin, resulted in decreased pigmentation.

Figure 3:
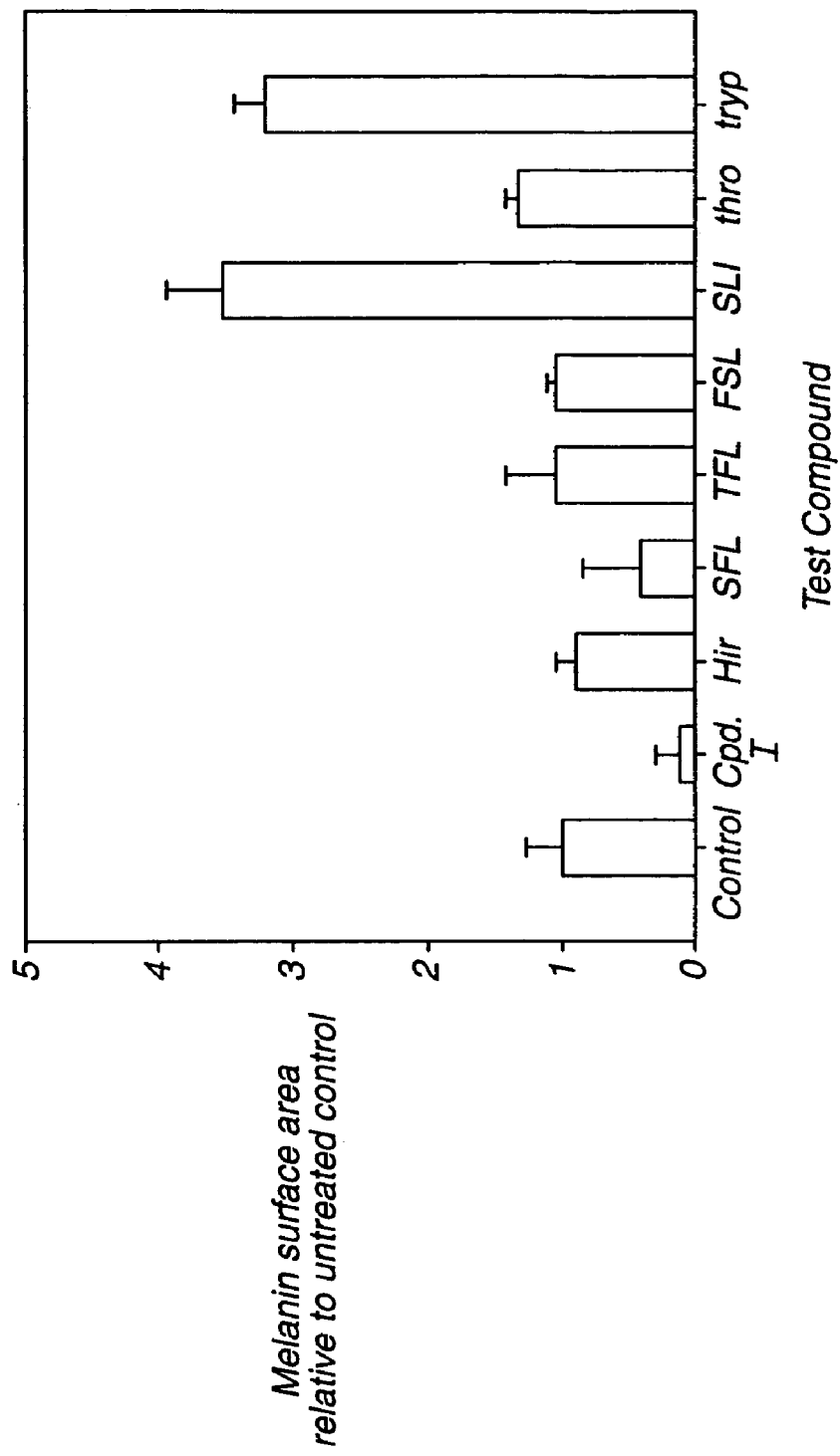
FIG. 3 is a graph depicting the increase or decrease in relative pigmentation in epidermal equivalents containing melanocytes treated in accordance with the methods and compositions of this invention.

FIG. 3 shows the results of the studies set forth in this example, representing the level of pigmentation in MelanoDerm equivalents treated with TR and PAR-2 reagents. SLIGRL, a PAR-2 agonist, dramatically increased pigmentation, indicating that PAR-2 might be involved in pigmentation. Hirudin, a thrombin-specific inhibitor, and TFLLRNPNDK, a TR selective agonist had no effect on pigmentation. However, SFLLRN, a less specific TR agonists, showed a trend of lightening or reducing pigmentation. This indicates that TR is less likely to be involved in pigmentation.

TABLE B

| TR and PAR-2 Reagents | Description |
| --- | --- |
| Thrombin | Activates TR |
| Trypsin | Activates TR and PAR-2 |
| TFLLRNPNDK | TR peptide agonist-activates TR only |

TABLE B-continued

| TR and PAR-2 Reagents | Description |
|---|---|
| SLIGRL | PAR-2 peptide agonist-activates PAR-2 only |
| SFLLRN | TR peptide agonist-activates TR, cross-reacts with PAR-2 |
| FSLLRN | Scrambled peptide-inactive |
| Hirudin | Specific inhibitor of thrombin |
| Compound I | Thrombin and trypsin inhibitor |

Example 3

A Dose-Response Relation Between Protease-Activated Receptors Signaling and Melanogenesis MelanoDerm equivalents were treated with increasing concentrations of SLIGRL, the PAR-2 peptide agonist, at 0, 10 and 50 µM in the same manner as set forth in Example 2. F&M staining was performed in the fourth day. As shown in FIG. 4A, increasing concentrations of SLIGRL, the PAR-2 activator, result in increased pigmentation. Trypsin, a PAR-2 activator, has the same effect. Treatment with increasing concentrations of Compound I, the thrombin and trypsin inhibitor, from 0.1 pM to 1 µM resulted in decreasing pigmentation (see FIG. 4A). Pretreatment of the equivalents with UVB irradiation increased melanogenesis, relative to untreated controls. Compound I was able to reduce this UVB-induced pigmentation as well (FIG. 4B). This example demonstrates a dose-response relation for increasing and decreasing pigmentation with the modulation of PAR-2 signaling. This example also demonstrates that Compound I can inhibit pigmentation and prevent UV-induced pigmentation.

Example 4

PAR-2 is Expressed in Keratin Cytes, but not in Melanocytes

PAR-2 and TR expression have been demonstrated previously in keratinocytes and fibroblasts. This example demonstrates that PAR-2 is expressed in keratinocytes, but not in melanocytes. Furthermore, it demonstrates that TR is expressed in both keratinocytes and melanocytes. In order to demonstrate this, MelanoDerm human epidermal equivalents, human primary melanocyte cultures (neonatal and adult, from Clonetics of San Diego, Calif.) and Cloudman S91 mouse melanoma cells from ATCC of Rockville, Md. were grown in culture and total RNAs were extracted using "RNA Stat-60" reagent available from "Tel-Test B", Incorporated as described in Chomczymski, "Single Step Method of RNA Isolation by Acid Guanidinium Thiocyanate-phenol-chloroform extraction," 162 Anal. Biochem. 156-69 (1987). A sufficient amount of RNase-free DNase available from Promega Corporation under the tradename "RQ1 RNase-free DNase" was then added to the extracted RNA from each sample such that each respective product will yield 200 ng of DNased-RNA using the procedure set forth in "RNase-free DNase", protocol published by Promega Corporation (May, 1995). The resulting 200 ng of DNased-RNA was reverse transcribed ("RT") via the procedure set forth in "Superscript II Reverse Transcriptase" a protocol published by Gibco-BRL (now Life Technologies, Incorporated) (April 1992), using random hexamers such as the random primers which are commercially available from Life Technologies, Incorporated.

The resulting RT products were then amplified via polymerase chain reaction ("PCR") using about a 0.5 unit (per 100 µl reaction) of a thermostable DNA polymerase which is commercially available from Perkin-Elmer-Cetus Corporation under the tradename "Taq polymerase" and about 0.1 µmol/reaction of TR and PAR-2 specific primers as described in Table C and in Marthinuss et al., 1995 which is hereby incorporated herein by reference or of glyceraldehyde-3-phosphate-dehydrogenase (G3PDH) primers, available from Clontech Laboratories, Inc. of Palo Alto, Calif. in accordance with the procedures set forth in Marthinuss et al., 1995 or in the protocol accompanying the primers from Clontech Laboratories.

The PCR products were then analyzed using 2% agarose/ethidium bromide gels according to methods well-known in the art in order to compare the level of expression of certain genes in keratinocytes and melanocytes. When necessary for better visualization, the resulting PCR products were precipitated with ethanol according to well-known procedures. When primers for G3PDH were used, only 10% of the PCR reaction products were used. An RNA sample from epidermal equivalents that was not reverse-transcribed was used as a negative control for each PCR amplification. The lack of genomic DNA contaminants was indicated by the lack of a band on the relevant lanes in the gels. A human skin RNA sample which was reverse-transcribed was used as a positive control when commercial positive controls were not available. The migration of the RT-PCR products on the gels was always identical to that of the positive controls, and to that of the reported amplimer sizes.

The relative quality of each respective RT-PCR reaction product was then compared by analyzing the mRNA level of G3PDH, a "housekeeping" gene, in each respective product. As illustrated in FIGS. 5 and 6, G3PDH gene expression was found to be similar at all the time points examined, which thereby enabled the comparison of the relative levels of gene expression for the desired genes.

Figure 5A:
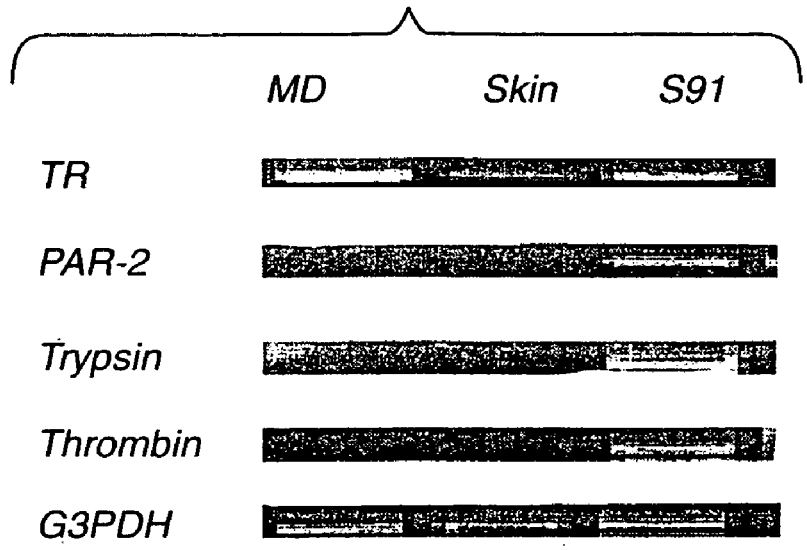
FIG. 5A is a photograph depicting gels showing the expression of TR and PAR-2 in skin, melanoma cells and epidermal equivalents containing melanocytes.

FIG. 5A shows that, as expected, TR and PAR-2 are expressed in total skin and in the MelanoDerm equivalents ("MD"). However, S91 melanoma cells ("S91") did not express PAR-2 or TR. To investigate this further, we tested primary newborn ("mel-NB") and adult ("mel-A") melanocytes for TR and PAR-2 expression. As shown in FIG. 5B, primary human melanocytes express TR but not PAR-2. Therefore, we suggest that PAR-2 agonists and antagonists can interact with keratinocytes, but not with melanocytes, in the MelanoDerm equivalents, and that TR agonists and antagonists could interact with both keratinocytes and melanocytes. A keratinocyte-melanocyte interaction is, therefore, suggested, during which the keratinocyte-PAR-2 signal is converted into a pigmentation end-point.

Table C illustrates some of the DNA primers used, the amount of $MgCl_2$ required for the PCR reaction, and the length of the PCR cycle.

TABLE C

DNA Primers Utilized in RT-PCR Assay

| Primer (See attached Sequence Listing) | Amt. of $MgCl_2$ (mM) | Cycle (min) @ ° C. | No. of. cycles | DNA Seq. ID No. |
|---|---|---|---|---|
| Tyrosinase sense TCAGCCCAGC ATCCTTCTTC | 1.25 | 1 @ 94<br>2 @ 55<br>3 @ 72 | 35 | 1 |
| Tyrosinase antisense | 1.25 | 1 @ 94 | 35 | 2 |

TABLE C-continued

DNA Primers Utilized in RT-PCR Assay

| Primer (See attached Sequence Listing) | Amt. of MgCl₂ (mM) | Cycle (min) @ ° C. | No. of. cycles | DNA Seq. ID No. |
|---|---|---|---|---|
| CAGCCATTGT TCAAAAATAC-TGTCC | | 2 @ 55<br>3 @ 72 | | |
| TRP-1 sense<br>5'CCACTCTAATAAGCCCAAAC | 2.5 | 1 @ 94<br>2 @ 55<br>3 @ 72 | 35 | 3 |
| TRP-1 antisense<br>5'CTCAGCCATTCATCAAAGAC | 2.5 | 1 @ 94<br>2 @ 55<br>3 @ 72 | 35 | 4 |
| TRP-2 sense<br>5'AAAAGACATACGAGATTGCC | 2.5 | 1 @ 94<br>2 @ 55<br>3 @ 72 | 35 | 5 |
| TRP-2 antisense<br>5'CACAAAAAGACCAACCAAAG | 2.5 | 1 @ 94<br>2 @ 55<br>3 @ 72 | 35 | 6 |
| Trypsin sense<br>5'ATCC/TACTCCTGATCCTTA-CC | 2.5 | 1 @ 94<br>2 @ 45<br>3 @ 72 | 35 | 7 |
| Trypsin antisense<br>5'TGTCATTGTT/CCAGAGTC-T/CT/GC/GC | 2.5 | 1 @ 94<br>2 @ 45<br>3 @ 72 | 35 | 8 |
| PAR-2 sense -<br>GGGAAAGGGGTTGGGGTAGAA CCAGGCTTTTCC (5') | 2.5 | .5 @ 94<br>1 @ 55<br>3 @ 72 | 30 | 9 |
| PAR-2 antisense -<br>GGCCAACGGCGATGTTTGCCTT CTTCCTGGGG(3') | 2.5 | .5 @ 94<br>1 @ 55<br>3 @ 72 | 30 | 10 |
| TR-sense -<br>CCTCTGAGTGCCAGAGGTACG-TCTACAG (5') | 2.5 | .5 @ 94<br>1 @ 55<br>3 @ 72 | 30 | 11 |
| TR-antisense -<br>CCTAAGTTAACAGCTTTTTGTAT ATGCTGTTATTCAGG (3') | 2.5 | .5 @ 94<br>1 @ 55<br>3 @ 72 | 30 | 12 |
| Thrombin-sense -<br>AACCTGAAGGAGACGTGGAC (3' | 2.5 | .5 @ 94<br>1 @ 55<br>3 @ 72 | 35 | 13 |
| Thrombin-antisense -<br>CAGGAGCCCAGAATATGAGTG ( | 2.5 | .5 @ 94<br>1 @ 55<br>3 @ 72 | 35 | 14 |

Example 5

Keratinocyte-Melanocyte Contact is Required for Compound I Depigmenting Effect

The results of Example 4 suggest that melanocytes alone might not respond to the depigmenting effect of PAR-2 antagonists. Indeed, the level of pigmentation of human primary melanocytes or choleratoxin-induced S91 cells, which is reduced by hydroquinone and benzaldehyde, was not affected by Compound I.

Since PAR-2 is not expressed in melanocytes, we tested the possible requirement of keratinocyte-melanocyte interactions for the depigmenting effect of Compound I. Primary melanocyte cultures were compared to identical cultures plated under epidermal equivalents (EpiDerm, lacking melanocytes) to create a co-cultur with no contact between keratinocytes and melanocytes. These were also compared to MelanoDerm equivalents, where melanocytes are present in the basal layer of the equivalent. Cultures were treated for three days with Compound I, with the PAR-2 agonist SLIGRL, and with the TR agonist TFLLRNPNDK, as set forth in Table D, and DOPA stained on the fourth day. In Table D, keratinocytes are indicated by "K", melanocytes are indicated by "M" and lack of keratinocyte-melanocyte contact is indicated as "no K-M contact". As shown in Table D, no effect on pigmentation was observed in primary melanocytes and in co-cultures treated with these agents. In MelanoDerm equivalents, compound I reduced and SLIGRL induced pigmentation, while TFLLRNPNDK had no effect. These results demonstrate that keratinocyte-melanocyte contact is required for the PAR-2 effect on pigmentation.

TABLE D

| Treatment | Melanocytes (no K) | Co-cultures (no K-M contact) | MelanoDerm (K-M contact) |
|---|---|---|---|
| Compound I | no effect | no effect | lightening |
| SLIGRL | no effect | no effect | darkening |
| TFLLRNPNDK | no effect | no effect | no effect |

Example 6

Compound I Affects Melanocyte Gene Expression

MelanoDerm equivalents were treated with increasing concentrations of the thrombin and trypsin inhibitor, Compound I, or with increasing concentrations of the PAR-2 agonist SLIGRL. RNAs extracted from untreated and Compound I-treated equivalents were analyzed for gene expression by RT-PCR in the manner set forth above in Example 4. Gene-specific primers were designed as set forth in Table C above, and Clontech primers for human G3PDH were used as in Example 4. Melanogenic genes tested for expression level were tyrosinase, TRP-1, and TRP-2.

Figure 6A:

A dose-dependent decrease in TRP-1 and a dose-dependent increase in TRP-2 mRNA levels were observed in Compound I-treated samples, as shown in FIG. 6A. Tyrosinase expression, however, was not affected. These changes correlated with the dose-dependent whitening effect of this inhibitor. Both patterns of gene expression result in a lightening effect. TRP-2 enzyme processes dopaquinone to 5,6-dihydroxyindole carboxylic acid (DHICA), rather than to 5,6-dihydroxyindole (DHI). This process results in brown, finely dispersed eumelanin, as opposed to insoluble black eumelanin, and results in a lighter skin tone. TRP-1 stabilizes the melanogenic complex, enabling pigment production. Reduced levels of TRP-1 result in reduced tyrosinase activity and reduced pigmentation. Lack of this protein results in albinism. Increasing concentrations of SLIGRL, however, did not affect melanogenic gene expression (FIG. 6B).

TRP-1 and TRP-2 are melanocyte-specific. Compound I inhibits trypsin and thrombin. Hirudin, a specific thrombin inhibitor, had no effect on pigmentation, as seen above in Example 2. Thus, we decided to test whether trypsin and thrombin are expressed in skin. A probe designed to detect both brain and gastric trypsins, as described in Table C, detected the expression of both mRNAs in a total skin mRNA sample available from Invitrogen of Carlsbad, Calif., as well as in MelanoDerm equivalents. The same expression pattern was detected for thrombin. Both trypsin and thrombin were not expressed in normal melanocytes (FIGS. 5A, B). These data suggest that if trypsin activates PAR-2, it could be produced by the keratinocytes only. As shown in FIG. 6A, treatment with Compound I resulted in increased expression of trypsin. SLIGRL, which did not affect melanogenesis gene expression (FIG. 6B) also increased trypsin expression in the equivalents. We conclude that while trypsin is a possible natural activator of PAR-2 in skin and possibly affects pigmentation, its mRNA levels do not correlate with pigmentation. This suggests that another, yet unidentified serine protease, which is inhibited by compound I, STI and the like, is the natural activator of PAR-2 in the epidermis. Compounds that induce or inhibit this protease would serve as darkening and lightening agents, respectively.

Example 7

Thrombin and Trypsin Inhibitors and PAR-2 Agonists Affect Pigmentation In Vivo

Two guinea pigs wer treated twice daily, five days/week for seven weeks with Compound I at 1 and 10 µM in 70:30 ethanol:propylene glycol vehicle on one pigmented nipple. The other nipple of each animal was treated with vehicle only and served as a control. Chromameter measurement after seven weeks of treatment revealed a dose-dependent lightening effect of +9.6 L* and nearly 18 L* units respectively. No visible signs of irritation were observed at that time.

Figure 7:
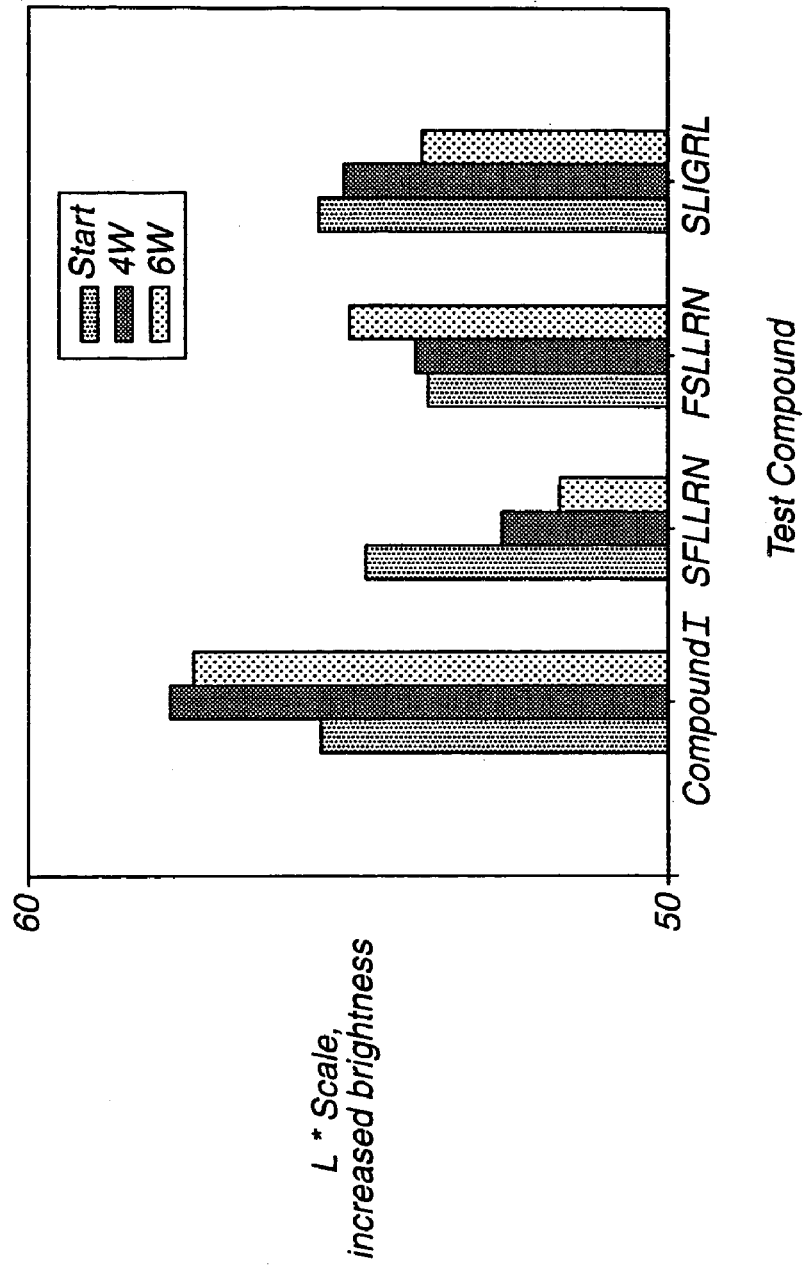
FIG. 7 is a graph showing the effects of different compositions of this invention on the brightness of guinea pig nipple pigmentation.

Four groups of three guinea pigs each were treated respectively with Compound I, SFLLRN, FSLLRN and SLIGRL at 10 µM, twice daily five days per week for eight weeks. Chromameter measurement after six weeks demonstrates a lightening effect by Compound I and a darkening effect by SLIGRL, the PAR-2 agonist. The results of this example are set forth in FIG. 7.

Example 8

Thrombin and Trypsin Inhibitors and PAR-2 Agonists Affect Pigmentation In vivo

A Yucatan microswine was treated with Compound I, SFLLRN, FSLLRN and SLIGRL at 10 µM. Each compound was applied to two sites on the pig twice daily, five days per week for eight weeks. After eight weeks of treatment, chromameter measurements were taken. The application of Compound I resulted in a visible lightening effect. The PAR-2 agonist SLIGRL resulted in a darkening effect as measured by chromameter. SFLLRN and FSLLRN had no significant effects.

Figure 8:
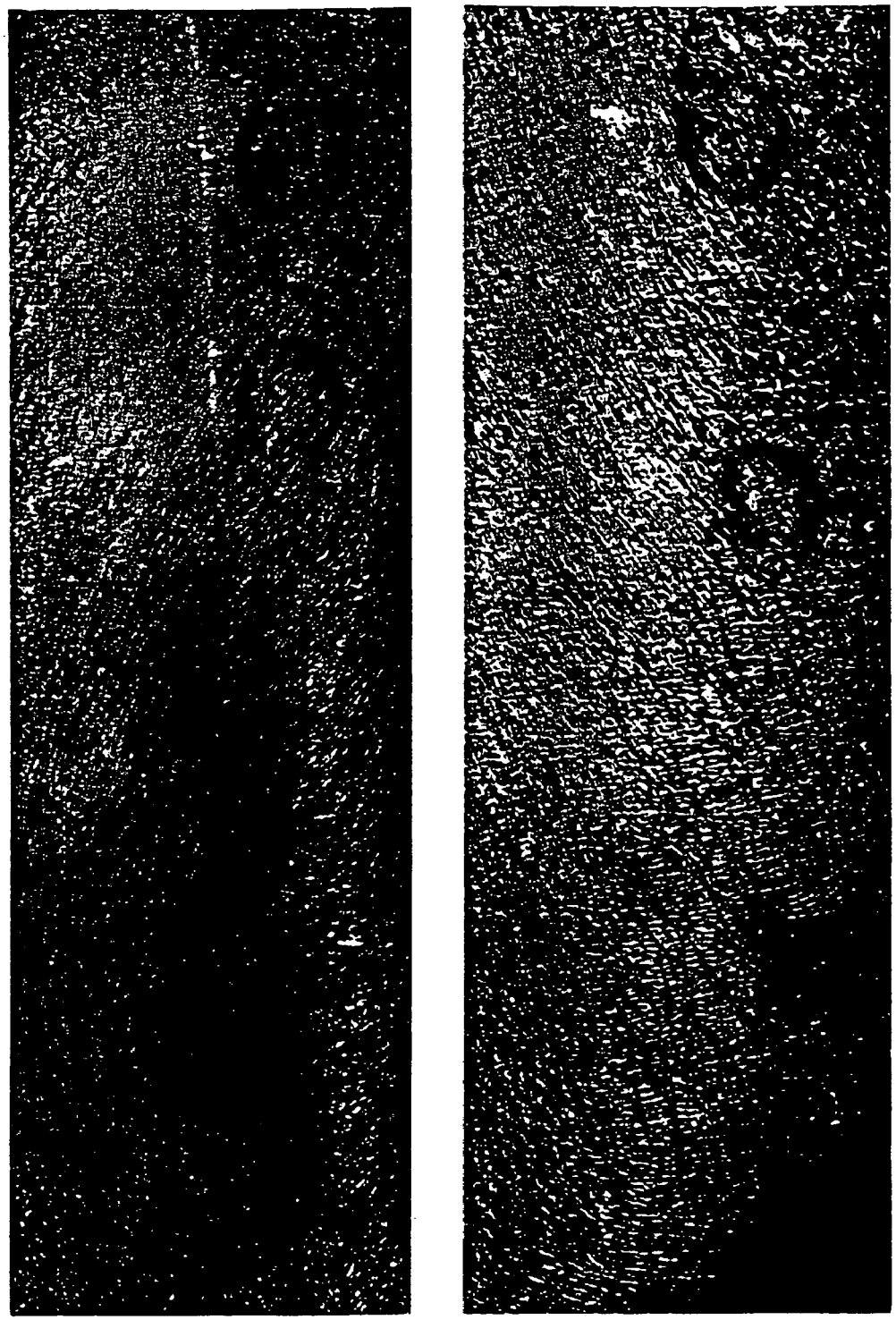
FIG. 8 is a photograph of Yucatan Swine skin which has been treated with compositions of this invention for depigmentation of skin.

Two Yucatan swine were treated for seven and a half weeks, or for ten weeks, twice daily, five days per week, with increasing concentrations of Compound I. Four concentrations of active compound were used, as follows: 0, 10, 50 and 250 µM. Two sites per concentration were placed on opposite sides of the swine dorsum. Chromameter measurements were taken before treatment started and every two weeks thereafter. Pictures were taken periodically and at the end of the experiment. A visible lightening effect was observed during the 4th, 5th and 6th weeks of treatment, for the 250, 50 and 10 µM treatments, respectively. By the eighth week, the whitening effect of the two highest doses was similar. These results are illustrated in FIG. 8. The chromameter readings (L*, measuring brightness) during the treatment course of one swine are shown in FIG. 9. A saturation effect is observed, which is a time and concentration dependent. This example demonstrates a visual depigmenting effect by Compound I, in the animal model system most resemble pigmented human skin.

At the end of these experiments, biopsies were taken for histological and electron microscopy (EM) analyses. Histological samples were stained with H&E and F&M. H&E staining showed that there was no irritation, inflammatory response or changes in skin architecture, demonstrating the safety of using Compound I over long periods of time. F&M staining demonstrated that there was reduced pigmentation in the treated samples, both in the basal layer and throughout the epidermis. These results are illustrated in FIG. 10. Untreated and vehicle-treated samples (FIG. 10A) were identical and darkest. The 10 µM treatment (FIG. 10B) showed reduced pigmentation and the 50 and 250 µM treatments (FIG. 10C, 10D, respectively) were the lightest.

The results of this example suggest that the maximal whitening effect of Compound I could be achieved with higher concentration over a shorter period of time or with lower concentration over a longer period of time. Thus, at least two difference regimens may be used to achieve the desired skin whitening results.

Example 9

Figure 11B:
FIGS. 11A, 11B and 11C are photographs of electron micrographic views of epidermal equivalents containing melanocytes treated with compositions of this invention.
Figure 11A:
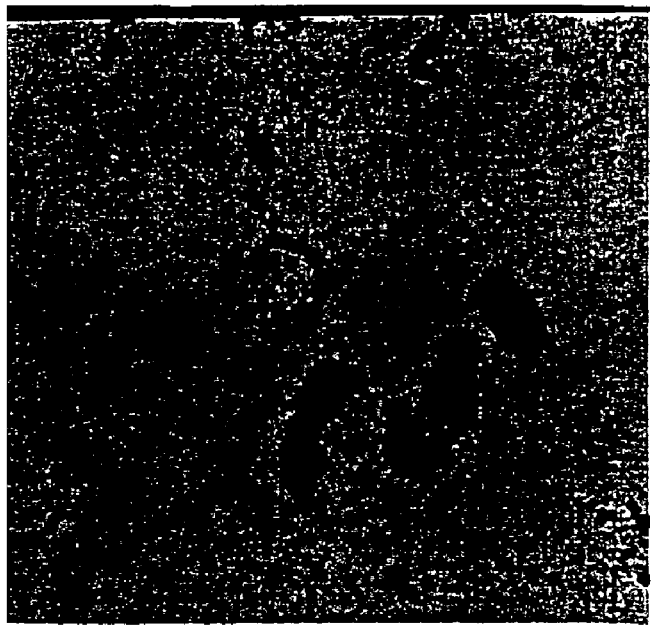
Figure 11C:

Ultrastructural Studies Demonstrate the Effect of Compound I On the Skin In Vitro and In Vivo Ultrastructural analysis was performed on MelanoDerm equivalents and swine skin sites treated with Compound I. MelanoDerm equivalents treated with Compound I were analyzed for melanosome formation and distribution using electron microscopy. Treated samples contained more melanosomes, but less mature melanosomes, i.e., melanosomes which evidence reduced melanin production, within the melanocytes, relative to untreated controls (FIG. 11A, 11B). Dendrites containing melanosomes were easily identified within treated keratinocytes (FIG. 11C), but were difficult to find within control keratinocytes. This suggests abnormal melanosome formation and slow or impaired melanosome transfer into keratinocytes in the treated samples.

Figure 11D:
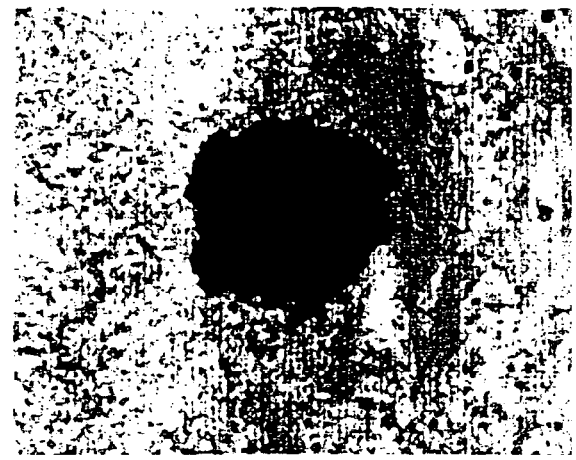
FIGS. 11D and 11G are photographs of electron micrographic views of untreated sites of Yucatan Swine skin.
Figure 11E:
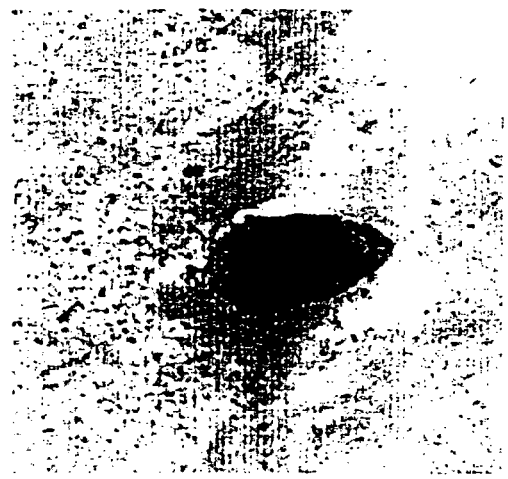
FIGS. 11E, 11F and 11H are photographs of electron micrographic views of Yucatan Swine skin treated with compositions of this invention.
Figure 11F:
Figure 11H:
Figure 11G:
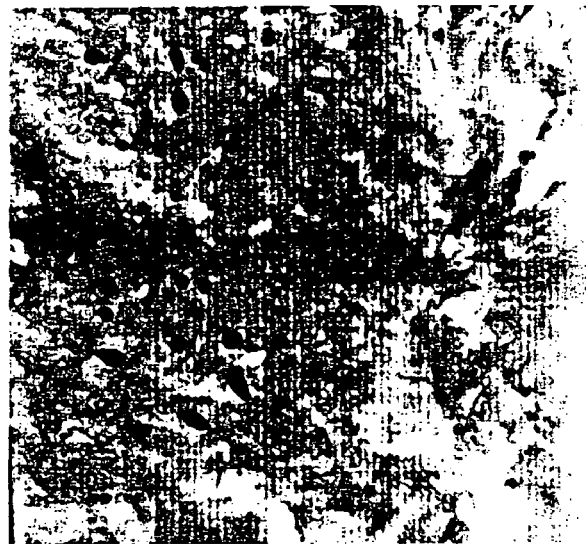

Skin samples from Yucatan swine treated with compound I for eight weeks, as described in example 8, were also analyzed by electron microscopy. Melanosomes within keratinocytes of treated sites were smaller and less pigmented, compared to controls (FIGS. 11D, 11E and 11F). Moreover, the distribution of melanosomes within the treated skins was abnormal. Melanosomes were detected mainly at the epidermal-dermal border, compared to a random distribution in untreated controls (FIGS. 11G, 11H). While we cannot rule out other mechanisms, we suggest that Compound I treated keratinocytes were unable to actively take or receive melanosomes from the presenting dendrites.

Example 10

The In Vivo Depigmenting Effect of Compound I is Reversible

Figure 12A:
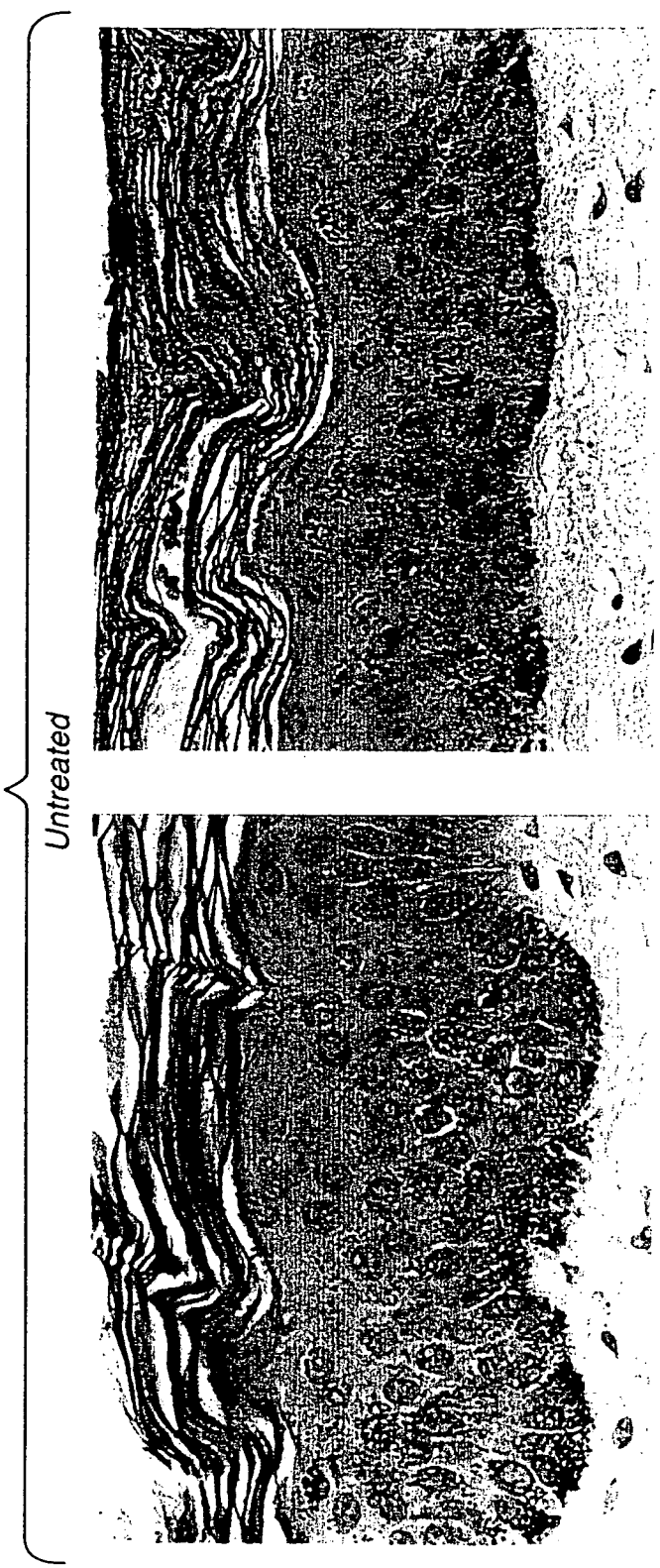
Figure 12D:
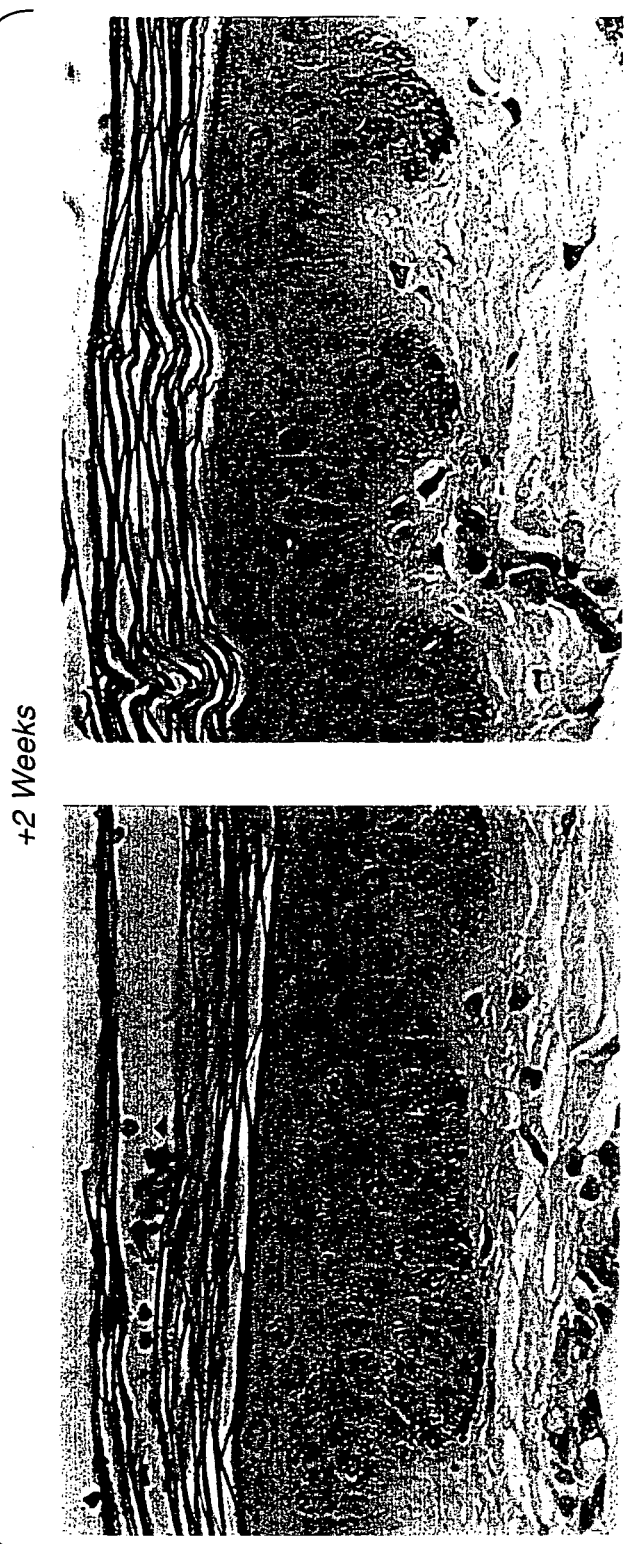

A Yucatan swine was treated with Compound 1,250 µM, for eight weeks, twice daily, five days a week, on eight sites. All sites showed visible depigmentation by the end of the treatment period, as set forth in FIG. 12B. For the following four weeks (starting at week nine of the experiment), the color of the treated sites was monitored, and two biopsies were taken each week from two treated sites. Untreated sites were biopsied as well. The depigmenting effect could be visualized at one and two weeks post treatment, and a complete reversal was observed by the forth week. Histological examination of F&M stained skin sections confirmed the repigmentation observed visually (as indicated in FIG. 12). As any as one week post treatment, repigmentation was demonstrated histologically. The visual observations correlate with the histological demonstration of stratum corneum pigmentation. This example demonstrates that Compound I does not induce a permanent damage to the pigmentation machinery, and its effect is reversible in vivo. FIG. 12A shows two histological F&M stained sections of sites which were not treated with Compound I. FIG. 12B shows two histological F&M stained sections of sites which were treated with Compound I for eight weeks. FIG. 12C shows sections of sites which were treated for eight weeks with Compound I, one week after treatment was stopped. FIG. 12D shows sections of sites which were treated for eight weeks with Compound I, two weeks after treatment was stopped. FIG. 12E shows sections of sites which were treated for eight weeks with Compound I, four weeks after treatment was stopped. As indicated in FIG. 12E, the sections were fully repigmented four weeks after the end of treatment.

Example 11

Preparation of Naturally-Derived Products Containing STI

Example 1 demonstrates that the presence of soybean trypsin inhibitor in any lightening formulation is desirable for its depigmenting activity. Based on analytical testing, it has been determined that soybean milk and soybean paste are rich sources of soybean trypsin inhibitor.

To make soybean paste, soybeans were first soaked in deionized or purified water for several hours. The soybeans were ground after they were fully hydrated, with the addition of small quantities of water, if needed, to smoothen the paste. To make soybean milk, the same procedure was performed with th addition of more water. (The grinding process allows the soybean milk to be extracted). After collection, the soybean milk was filtered to remove any residual parts of the bean husk.

Soybean milk, soybean paste and miso were prepared to be used as naturally-derived materials that contain STI and are able to lighten skin color.

Example 12

Figure 13:
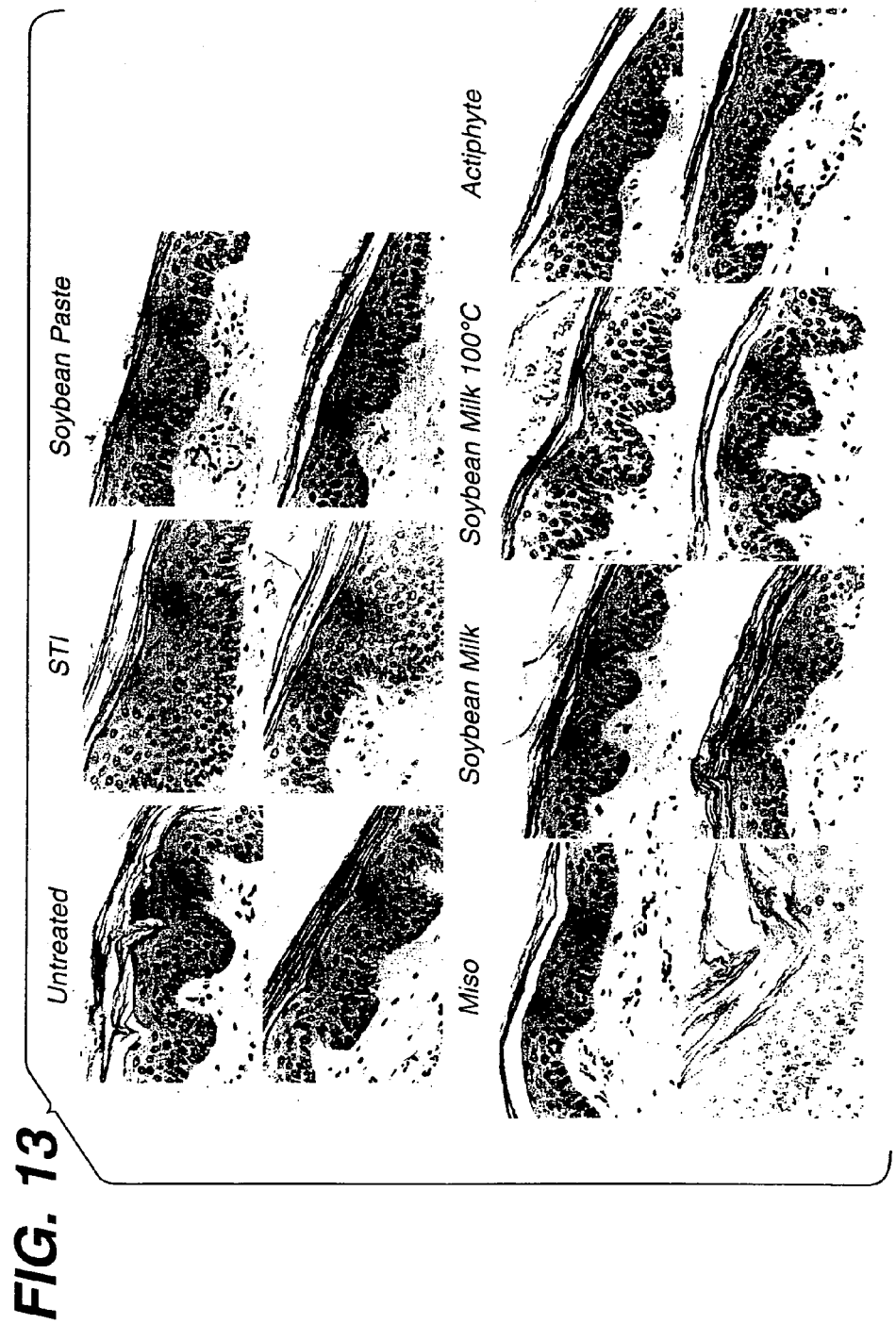
FIG. 13 is a photograph of F&M stained histological sections taken from Yucatan Swine skin treated with compositions of this invention.

Treatment with Naturally-Derived Materials that Affect the PAR-2 Pathway Induces Depigmentation Two Yucatan swine were treated for eight and ten weeks, twice a day, five days a week, with different soybean- and lima-bean-derived products. These natural products include soybean paste, soybean protein acid hydrolysate, miso, native and boiled soybean milk, and a commercially available extract of soybean (Actiphyte™ of Active Organics, Dallas Tex.), as well as purified STI, and different preparations of trypsin inhibitors from soybeans and limabeans. At seven weeks of treatment, all sites were visually lighter than the surrounding skin, except for the boiled soybean milk and the soybean protein acid hydrolysate treated sites. Histological analysis of biopsies from the treated sites following F&M staining confirmed the depigmenting effect of the soybean and limabean products. An example of such histological data is given in FIG. 13. The lack of depigmenting activity in the boiled soybean milk and in the soy protein acid hydrolysate is explained by the denaturation or the degradation of the soy proteins in these preparations, respectively. We theorize that the active depigmenting agents in the soybean and limabean products are soybean trypsin inhibitor (STI) and limabean trypsin inhibitor, respectively. (Example 1 shows the depigmenting effect of STI in vitro). This example demonstrate that natural extracts containing trypsin inhibitory activity could be used as whitening agents which affect the PAR-2 pathway.

Example 13

An STI in Liposome Formulation can Lighten Human Age Spots

An individual with three age spots on the dorsum of their hand was treated for eight weeks, twice a day, with the following: The age spot located closest to the arm was treated with placebo, containing 20 mg/ml of liposomes. The middle age spot was not treated. The third age spot was treated with STI, 1%, in liposomes (20 mg/ml). GDL liposomes were prepared as set forth in Niemiec, et al., above, with the exception of the following changes: the non-ionic liposomal formulation contained glycerol dilaurate (Emulsynt GDL, ISP Van Dyk)/cholesterol (Croda)/polyoxyethylene-10-stearyl ether (Brij76, ICI)/polyoxyethylene-9-lauryl ether, as at ratio of 37.5:12.5:33.3:16.7. Hepes buffer, 0.05M, pH 7.4 (Gibco-BRL of Gaithersburg, Md.) was used as the aqueous phase in the preparation of the liposomes. UV and visible light digital pictures were taken at time 0, 4 and 8 weeks of treatment. L* (brightness) values were calculated from the images using Adobe Photoshop.

Figure 14:
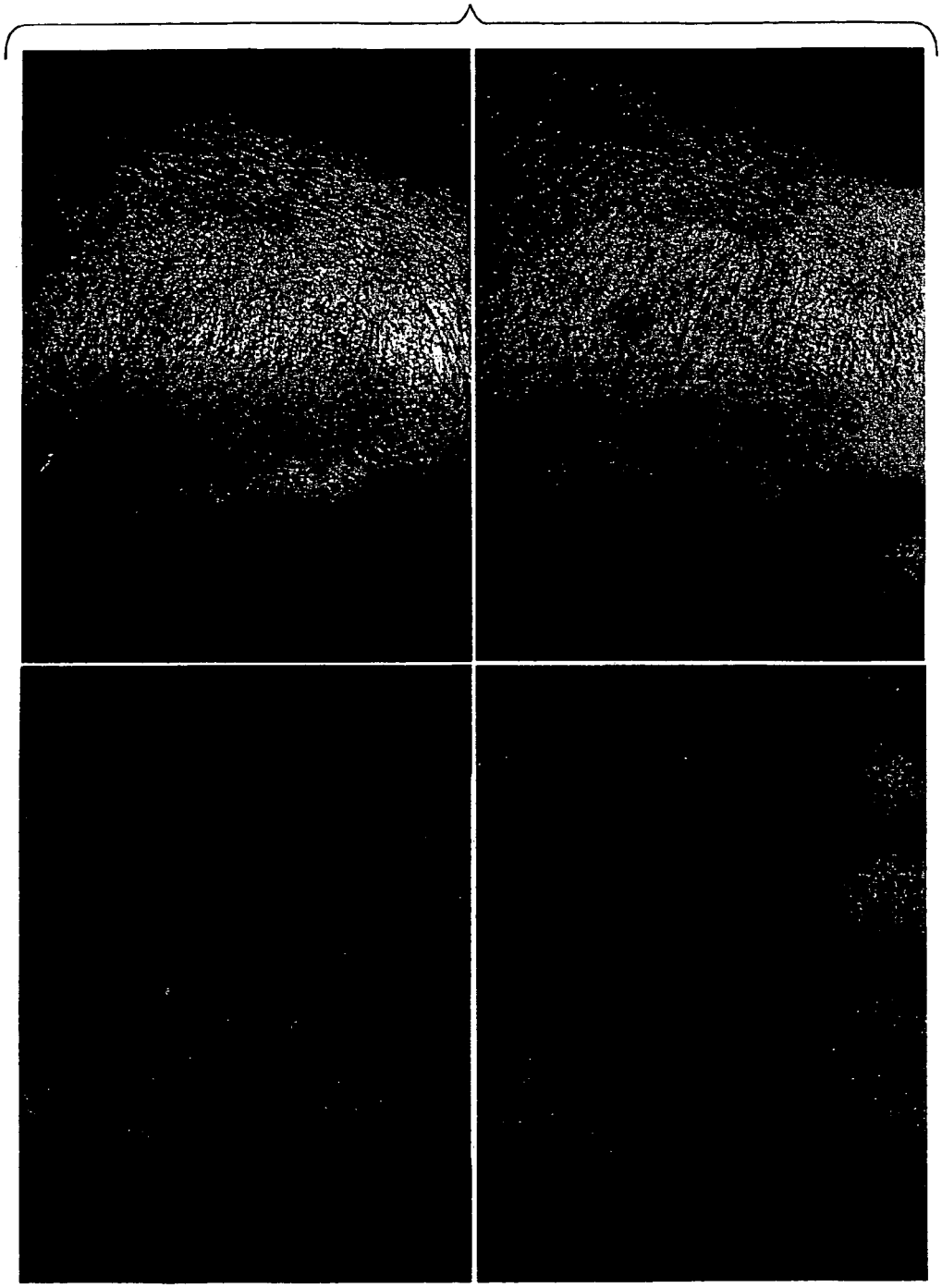
FIG. 14 contains ultraviolet and visible light digital photographs of human skin prior to treatment and subsequent to treatment with compositions of this invention.

As shown in FIG. 14, the age spot treated with STI became lighter following 8 weeks of treatment. FIG. 14 is a composite of four pictures. The left panel is the visible light pictures of the hand, before (upper) and after (lower) 8 weeks of treatment. At this orientation the top age spot is the placebo-treated, the middle age spot is untreated, and the lower age spot is the STI-treated. The right panel shows the same hand at the same time points, using UV-photography. UV light enables the visualization of pigment deeper in the skin, demonstrating that the STI whitening effect was not superficial. FIG. 14 clearly demonstrates that the STI formulation was able to lighten the lower age-spot. An increase of 15 L* units was calculated for this STI-treated sit, further demonstrating the ability of this treatment to lighten age spots.

Example 14

Depigmenting Formulations with Soybean Milk

In making the soybean milk, it was discovered that the rich emolliency of the milk would be desirable in a skin care formulation. Because water is used as the predominant ingredient of any oil-in-water emulsion, and in many other skin-care formulations we hypothesized that the soymilk could be used to substitute for the deionized water in such formulations. However, we expected that this type of formulation would not be physically stable due to the immiscibility of the oil and water components of the soybean milk. Surprisingly, we found that this substitution of soybean milk for water was physically stable. Formulations utilizing soybean milk should contain between about 1% and about 99% of soybean milk, more preferably from about 80% to about 95% soybean milk. Preferably, this and similar formulations should include a viscosity builder in an amount from about 0% to about 5% (more preferably, from about 0.1 to about 2%), one or more emollients in an amount up to about 20% and/or emulsifiers in an amount from about 0.1% to about 10% (more preferably from about 3 to about 5%), and, optionally, a spreading agent in an amount from about 0 to about 5% (more preferably from about 1 to about 2%), a preservative, a chelating agent or a humectant. The preservative should be present in an effective amount in order to preserve integrity of the milk and maintain the composition's activity. Sufficient thickener should be present to impart body to the formulation without causing it to become so viscous that it would hinder spreadability, e.g., from about 0 to about 10%, more preferably from about 3 to about 5%. Sunscreen, antioxidants, vitamins other depigmenting agents and other skin care topical ingredients may also be incorporated into the compositions of this invention.

A particularly preferred example of a depigmenting formulation substituting soymilk for water is shown in table E below.

TABLE E

| Ingredient | Function | % Wgt/Wgt |
|---|---|---|
| soybean milk | Vehicle, depigmenting | 84.9% |
| aluminum starch octenyl succinate | viscosity builder | 0.75% |
| cyclomethicone | spreading agent | 2% |
| PEG 6-capric/caprylic triglycerides | emollient/emulsifier | 3% |
| phenoxyethanol | preservative | 0.75% |
| sucrose cocoate | emollient/emulsifier | 1% |
| Na₂EDTA | chelating agent | 0.1% |
| glycerin | humectant | 2.5% |
| polyacrylamide; isoparaffin; laureth-7 | thickener | 5% |

STI, soybean paste and other trypsin inhibitor-containing natural extracts can be incorporated into such formulations to provide increasing concentrations of the serine protease inhibitor. Use levels of the added active ingredient can range between 0.01% to 15% in a formulation. Other depigmenting agents, including PAR-2 inhibitors, tyrosinase inhibitors, hydroquinones, soy products, ascorbic acid and its derivatives, as well as other ingredients with skin care benefits could also be incorporated into this formulation.

Example 15

An Oil-in-Water Emulsion Depigmenting Formulation

Two examples of a depigmenting formulation with oil-in-water emulsion are presented in Table F. A formulation with STI, where STI could be replaced with any naturally-derived serine protease inhibitor, or with any naturally-derived extract or fraction thereof containing serine protease inhibitors, is described in column 4 of Table F. A similar formulation with Compound I is presented in column 5 of Table F. Compound I in this composition could be replaced with similar compounds, or with serine protease inhibitors or with any PAR-2 inhibitor materials having high therapeutic indices, whether derived synthetically or naturally, as the active ingredient. Suggest d ranges for the ingredients in such formulations are also listed in Table F. The deionized water content of these formulations could be replaced with soybean milk.

TABLE F

| Phase | CTFA Name | Function | % W/W | % W/W | Ranges |
|---|---|---|---|---|---|
| OIL | Cetearyl Glucoside | Surfactant | 1.4 | 1.4 | 0.1-2.8 |
| | C12-15 Alkyl Benzoate | Surfactant | 4.0 | 4.0 | 1-6 |
| | Octyl Hydroxystearate | Emollient | 1.0 | 1.0 | 0-5 |
| | Dimethicone | Spreading Agent | 1.0 | 1.0 | 0-5 |
| | Cyclomethicone | Spreading Agent | 1.0 | 1.0 | 0-5 |
| | Cetyl Alcohol | Emollient | 2.5 | 2.5 | 0-4 |
| | Butylated Hydroxytoluene | Anti-oxidant | 0.1 | 0.1 | 0-0.5 |
| | Octyl Methoxycinnamate | Sunscreen | 6.0 | 6.0 | 0-10 |
| | Propylparaben | Preservative | 0.5 | 0.1 | 0-0.5 |
| | Vitamin E acetate | Anti-oxidant | 0.5 | 0.5 | 0-0.5 |
| | Tocopherol Acetate | Anti-oxidant | 0.5 | 0.5 | 0-0.5 |
| AQUE-OUS | Glycerine | Humectant | 3.0 | 3.0 | 0-20 |
| | D-Pathenol | Pro-Vitamin | 0.5 | 0.5 | 0-5 |
| | Disodium EDTA | Chelator, whitening agent | 0.1 | 0.1 | 0.01-1 |
| | Methyl Paraben | Preservative | 0.2 | 0.2 | 0-0.3 |
| | Carbomer | Thickener | 0.35 | 0.35 | 0-3 |
| | Deionized Water or Soybean Milk | Carrier/ Whitening Agent | 76.35 1.0 | 77.5 | 50-80 |
| | STI or natural extract | Whitening Agent | | 0 | 0-15 |
| | Compound I | Whitening Agent | 0 | 0.25 | 0-1 |

To prepare this formulation, the ingredients of the lipid phase were combined and mixed at 85° C., and then cooled to 60° C. In a separate vessel, the carbopol was slowly added to the water or to the soybean milk. After mixing for ten minutes the rest of the aqueous phase ingredients were added and the mix was heated to 60° C. The two phases were then combined, mixed for ten minutes, and cooled to room temperature. Of course, one or more depigmentation agents may be combined within the same formulation, in this Example and in the following examples and other embodiments of the methods and compositions of this invention.

Example 16

Depigmenting Composition (Oil-in-Water Emulsion)

Two additional examples of an oil-in-water emulsion depigmenting formulation are presented in Table G. A formulation with STI, where STI could be replaced with any naturally-derived serine protease inhibitor, or with any naturally-derived extract or fraction thereof containing serine protease inhibitors, is described in column 3 of Table G. A similar formulation with Compound I is presented in column 4 of Table G. Compound I in this composition could be replaced with similar compounds or with serine protease inhibitor or with any PAR-2 inhibitor materials having high therapeutic indices, whether derived synthetically or naturally, as the active ingredient. Suggested ranges for the ingredients in such formulations are also listed in Table G. The deionized water content of these formulations could be replaced with soybean milk.

TABLE G

| CTFA Name | Function | % W/W | % W/W | Pref'd. Ranges |
|---|---|---|---|---|
| Ethanol | Solvent | 12.0 | 12.0 | 5-20 |
| Propylene Glycol | Solvent | 3.0 | 3.0 | 1-10 |
| Hydroxyethylcellulose | Thickener/Polymer | 0.2 | 0.2 | 0-3 |
| Acrylates/C10-30 Alkyl Acrylate Crosspolymer | Thickener/Polymer | 1.0 | 1.0 | 0-3 |
| Panthenol (98%) | Pro-Vitamin/Humectant | 1.5 | 1.5 | 0.1-3 |
| Fragrance | Fragrance | 0.5 | 0.5 | 0-0.5 |
| Isohexadecane | Spreading Agent | 4.0 | 4.0 | 0-5 |
| Vitamin E acetate | Anti-oxidant | 1.0 | 1.0 | 0-2 |
| Sodium Hydroxide | Neutralizer | 0.35 | 0.35 | 0.1-0.5 |
| Glycerine | Humectant | 3.0 | 3.0 | 0-20 |
| Deionized Water or Soybean Milk | Carrier/Whitening Agent | 72.2 | 71.95 | 60-80 |
| Compound I | Whitening Agent | 0 | 0.25 | 0-1 |
| STI or natural extract | Whitening/Agent | 1.0 | 0 | 0-15 |

To prepare this formulation, the hydroxyethylcellulose was slowly added to the water or to the soybean milk and stir until completely dissolved. In a separate container the Acrylates/C10-30 Alkyl Acrylate Crosspolymer was added and stir until completely dissolved. The content of the two containers was combined and mixed for 20 minutes. Vitamin E acetate was then added and mixed, following by the addition of Isohexadecane and Panthenol (98%). After mixing for five minutes the STI, or the natural extract, or Compound I were added together with Propylene Glycol, and stirred for 5 minutes. Next, glycerine was added and the formulation was stirred for 20 minutes. Finally, the pH was adjusted with sodium hydroxide to 8 for STI (range is 6-8.5) or to 7 for Compound I (range is 5.5-8.5).

Example 17

Depigmenting Composition (Water-In-Oil Emulsion)

An example of a depigmenting formulation with water-in-oil emulsion is presented in Table H. A formulation with STI, where STI could be replaced with any naturally-derived serine protease inhibitor, or with any naturally-derived extract or fraction thereof containing serine protease inhibitors, is described in column 4 of Table H. A similar formulation with Compound I is presented in column 5 of Table H. Compound I in this composition could be replaced with similar compounds or with serine protease inhibitor or with any PAR-2 inhibitor materials having high therapeutic indices, whether derived synthetically or naturally, as the active ingredient. Suggested ranges for the ingredients in such formulations are also listed in Table H. The deionized water content of these formulations could be replaced with soybean milk.

TABLE H

| Phase | CTFA Name | Function | % W/W | % W/W | Pref'd Ranges |
|---|---|---|---|---|---|
| OIL | Mineral Oil | Emollient | 25.0 | 25.0 | 40-80 |
| | Sorbitan Monooleate | Surfactant | 5.0 | 5.0 | 1-6 |
| | Stearyl Alcohol | Emollient | 25.0 | 25.0 | 20-60 |
| | Dimethicone | Spreading Agent | 1.0 | 1.0 | 1-5 |
| | Cetyl Alcohol | Emollient | 2.0 | 2.0 | 0.1-10 |
| | Hydrogenated Lecithin | Anti-oxidant | 3.0 | 3.0 | 0-10 |
| | Parsol MCX | Sunscreen | 3.0 | 3.0 | 0-10 |
| | Propylparaben | Preservative | 0.5 | 0.5 | 0.01-0.5 |
| | Vitamin E acetate | Anti-oxidant | 0.5 | 0.5 | 0.01-0.5 |
| AQUEOUS | Glycerine | Humectant | 3.0 | 3.0 | 0-20 |
| | Methyl Paraben | Preservative | 0.2 | 0.2 | 0.01-0.3 |
| | Water or Soy Milk | Carrier/Whitening Agent | 30.8 | 31.55 | 20-45 |
| | STI | Whitening Agent | 1.0 | 0 | 0-10 |
| | Cpd I | Whitening Agent | 0 | 0.25 | 0-1 |

To prepare this formulation the stearyl alcohol and mineral oil were melted at 70° C. The other oil phase ingredients were added and the mixture heated to 75° C. The aqueous phase ingredients, which have been previously dissolved in the bulk phase water or Soy Milk and warmed to 70° C., were then added and the mixture was stirred until it congealed.

Example 18

Depigmentation Composition (Aqueous Gel)

Two examples of a depigmenting formulation with aqueous gel are presented in Table J. A formulation with STI, where STI could be replaced with any naturally-derived serine protease inhibitor, or with any naturally-derived extract or fraction thereof containing serine protease inhibitors, is described in column 3 of Table J. A similar formulation with Compound I is presented in column 4 of Table J. Compound I in this composition could be replaced with similar compounds or with serine protease inhibitor or with any PAR-2 inhibitor materials having high therapeutic indices, whether derived synthetically or naturally, as the active ingredient. Suggested ranges for the ingredients in such formulations are also listed in Table J. The deionized water content of these formulations could be replaced with soybean milk.

TABLE J

| CTFA Name | Function | % W/W | % W/W | |
|---|---|---|---|---|
| Octoxynol-13 | Surfactant | 0.2 | 0.2 | 0.05-0.5 |
| 2,4-Hexadienoic Acid | Preservative | 0.1 | 0.1 | 0-0.3 |
| Benzenemethanol | Preservative | 1.0 | 1.0 | 0-2 |
| Disodium EDTA | Chelator/Preservative | 0.05 | 0.05 | 0.01-0.2 |
| Ascorbic Acid | Anti-oxidant | 0.1 | 0.1 | 0-0.2 |
| Sodium Metabisulfite | Anti-oxidant | 0.2 | 0.2 | 0-0.3 |
| Carbomer | Thickener | 1.5 | 1.5 | 0-3.0 |
| NaOH %20 Soln. | Neutralizer | 2.45 | 2.45 | 0.1-5 |
| DEIONIZED Water or Soybean Milk | Carrier/Whitening Agent | 93.4 | 94.15 | 85-98 |
| STI or natural extract | Whitening Agent | 1.0 | 0 | 0-15 |
| Compound I | Whitening Agent | 0 | 0.25 | 0-1 |

To prepare this formulation, the Disodium EDTA, sodium metabisulfite and ascorbic acid were slowly added to the water or to the soybean milk and stir until completely dissolved. STI, natural extracts or Compound I were then added and mixed slowly for five minutes. The speed of agitation was then increased and carbopol was added. The composition was mixed for 30 minutes or until the dispersion was free of "fish eyes", which are non-dispersed clear lumps, and heated to 50° C. In a separate container, the slurry phase was prepared by combining Octoxynol-13, 2,4-Hexadienoic acid, and Benzenemethanol and stirring ten minutes at 40-50° C. The slurry was then added slowly to the aqueous phase, mixed, and cooled to 45° C. 20% sodium hydroxide solution was used to pH the composition to pH of 7.0 (range is 5.5-8.5). This was mixed to homogeneity using agitation or sweep vessel.

Example 19

Solvent-Based Depigmenting Composition

An example of a depigmenting formulation containing solvent is presented in Table K. A formulation with STI, where STI could be replaced with any naturally-derived serine protease inhibitor, or with any naturally-derived extract or fraction thereof containing serine protease inhibitors, is described in column 3 of Table K. A similar formulation with Compound I is presented in column 4 of Table K. Compound I in this composition could be replaced with similar compounds or with serine protease inhibitor or with any PAR-2 inhibitor materials having high therapeutic indices, whether derived synthetically or naturally, as the active ingredient. Suggested ranges for the ingredients in such formulations are also listed in Table K. The deionized water content of these formulations could be replaced with soybean milk

TABLE K

| CTFA Name | Function | % W/W | Range |
|---|---|---|---|
| Ethanol | Solvent (1) | 70 | 40-90 |
| Propylene Glycol | Solvent (2) | 29 | 1-40 |
| Deionized Water | Carrier | q.s. | 1-40 |
| STI | Whitening Agent | 0 | |
| Compound I | Whitening Agent | 1 µM | .00001-1 |

To prepare this formulation Compound I was dissolved in water. The ethanol and propylene glycol were mixed and combined with the aqueous solution containing Compound I.

In summary, we have demonstrated that activation of the keratinocyte receptor PAR-2 results in increased pigmentation. Preferably, such activation may be accomplished by the use of trypsin or SLIGRL or SLIGKVD or other SLIGRL or SLIGKVD derivatives. We have also demonstrated that whitening may be accomplished by the use of serine protease inhibitors or PAR-2 antagonists, as well as by melanosome-transfer blockers. Other compounds known to those of skill in the art that inhibit melanosome transfer into keratinocytes could also be used as depigmenting agents.

Compound I, a trypsin and thrombin inhibitor, for example, inhibits melanosome transfer to keratinocytes. STI works by the same mechanism. The accumulation of undelivered melanosomes in the melanocytes could induce a negative feed back mechanism, that slows new melanosome formation. The production of TRP-1, the major glycoprotein in melanocytes, is down-regulated, which leads to destabilization of tyrosinase. This results in reduced melanin formation, and in a color switch to a lighter brown, as the ratio of TRP-1:TRP-2 is reduced. The melanosomes accumulation in the melanocyte after Compound I treatment, or after STI treatment, therefore, have reduced and altered melanin content, which adds to the whitening effect of compound I or STI.

What is claimed is:

1. A method of effecting changes in mammalian skin pigmentation comprising administering to a mammal a pigmentation-changing effective amount of a composition which affects the PAR-2-pathway wherein said composition comprises soybean extracts in which proteins have not been denatured and which comprise soy trypsin inhibitory activity.

2. A method according to claim 1 wherein said soybean extracts in which proteins have not been denatured comprise soybean milk.

3. A method according to claim 1 wherein said soybean extracts in which proteins have not been denatured comprise soybean paste.

4. A method according to claim 1 wherein said soybean extracts in which proteins have not been denatured comprise a fraction selected from the group consisting of soybean milk, soybean paste and mixtures thereof.

5. A method according to claim 1 wherein said soybean extract is present in an amount from about 0.001 to about 5% by weight of said composition.

6. A method according to claim 1 wherein said soybean extract is present in an amount from about 0.006 to about 1% by weight of said composition.

7. A method according to claim 2 wherein said soybean milk is present in an amount of from about 1 to about 99% by weight of the composition.

8. A method according to claim 1 wherein said composition comprises said soybean extracts in an amount of from about 0.01 to about 20% by weight of the composition.

9. A method according to claim 1 wherein said composition is applied twice daily for at least eight weeks.

10. A method according to claim 1 wherein said composition further comprises a cosmetically-acceptable vehicle.

11. A method according to claim 1 wherein said composition further comprises from about 0.1 to about 20% emulsifier and a preservative in an effective amount.

12. A method of effecting changes in mammalian skin pigmentation comprising administering to a mammal a pigmentation-changing effective amount of a composition which affects the PAR-2-pathway wherein said composition consists essentially of non-denatured soybean extracts containing trypsin inhibitory activity.

13. A method of lightening age spots comprising administering to an age spot on the skin of a mammal a pigmentation-changing effective amount of a composition which affects the PAR-2-pathway wherein said composition comprises soybean extracts in which proteins have not been denatured and which comprise soy trypsin inhibitory activity.

* * * * *